United States Patent
Aydt et al.

(10) Patent No.: US 9,492,681 B2
(45) Date of Patent: Nov. 15, 2016

(54) DEVICE AND METHOD FOR TREATMENT OF CELLS AND CELL TISSUE

(75) Inventors: Ewald Aydt, Rossdorf (DE); Herwig Buchholz, Frankfurt am Main (DE); Junyou Pan, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 432 days.

(21) Appl. No.: 13/985,209

(22) PCT Filed: Jan. 16, 2012

(86) PCT No.: PCT/EP2012/000156
§ 371 (c)(1),
(2), (4) Date: Aug. 13, 2013

(87) PCT Pub. No.: WO2012/110178
PCT Pub. Date: Aug. 23, 2012

(65) Prior Publication Data
US 2013/0324909 A1     Dec. 5, 2013

(30) Foreign Application Priority Data

Feb. 14, 2011    (EP) .................................... 11001174

(51) Int. Cl.
| | |
|---|---|
| A61N 1/00 | (2006.01) |
| A61N 5/06 | (2006.01) |
| A61F 9/008 | (2006.01) |
| H01L 51/50 | (2006.01) |

(52) U.S. Cl.
CPC ............. *A61N 5/06* (2013.01); *A61F 9/00834* (2013.01); *A61N 5/062* (2013.01); *A61N 5/0616* (2013.01); *H01L 51/50* (2013.01); *A61N 2005/0653* (2013.01); *A61N 2005/0654* (2013.01); *A61N 2005/0656* (2013.01); *A61N 2005/0659* (2013.01); *A61N 2005/0661* (2013.01); *A61N 2005/0662* (2013.01); *H01L 51/502* (2013.01); *H01L 51/5032* (2013.01)

(58) Field of Classification Search
CPC ................... A61N 2005/0652; A61N 5/0616; A61N 5/062
USPC ........................................ 607/88, 89; 604/20
See application file for complete search history.

(56) References Cited

U.S. PATENT DOCUMENTS

2005/0149150 A1* 7/2005 McDaniel ............ A61N 5/0616
                                                                        607/88
2010/0137950 A1    6/2010 McDaniel
(Continued)

FOREIGN PATENT DOCUMENTS

JP        2007-518452 A      7/2007
WO    WO-2010/078581 A1    7/2010
(Continued)

OTHER PUBLICATIONS

International Preliminary Report on Patentability for PCT/EP2012/000156, Aug. 21, 2013.
International Search Report for PCT/EP2012/000156 mailed Mar. 22, 2012.

*Primary Examiner* — William Thomson
*Assistant Examiner* — Jeffrey Lipitz
(74) *Attorney, Agent, or Firm* — Drinker Biddle & Reath LLP

(57) ABSTRACT

The present invention relates to a cells and cell tissue treatment device and use thereof.

18 Claims, 5 Drawing Sheets

(56) References Cited

U.S. PATENT DOCUMENTS

2010/0179469 A1\* 7/2010 Hammond ........... A61N 5/0603
 604/20
2010/0234792 A1 9/2010 Dacey, Jr. et al.

FOREIGN PATENT DOCUMENTS

| WO | WO-2011/069590 A1 | 6/2011 |
| WO | WO-2011110275 A2 | 9/2011 |

\* cited by examiner

DEVICE AND METHOD FOR TREATMENT OF CELLS AND CELL TISSUE

CROSS-REFERENCE TO RELATED APPLICATIONS

This application is a national stage application (under 35 U.S.C. §371) of PCT/EP2012/000156, filed Jan. 16, 2012, which claims benefit of European application 11001174.9, filed Feb. 14, 2011.

The present invention relates to a cells and/or cell tissue treatment device, to a kit of parts for treatment of cells and/or cell tissue, to use of such a device or kit of parts and to a method for treatment of cells and cell tissue.

Phototherapy (also called light therapy) can be employed in a wide range of therapeutic diseases and/or cosmetic (also called aesthetic) conditions. Phototherapy by either employing LED or laser as light source has already been used to treat wounds, injuries, neck pain, osteoarthritis, the side effects of chemotherapy and radiotherapy, for instance.

The treatment or prophylaxis of acne may have both therapeutic and cosmetic components, depending on the degree of the condition. The same accounts for psoriasis, atopic dermatitis and other diseases and/or conditions. Many diseases and conditions are associated with apparent implications which are often represented by a change in the visibility of a subject's skin, for instance. These cosmetic or aesthetic changes can often lead to psychological modifications resulting, at least in part, in serious diseases.

Some conditions or diseases may have an emphasis on cosmetic components. Some of these are selected from anti-ageing, anti-wrinkle, the prevention and/or therapy of acne and vitiligo. Sometimes, therapeutic elements may also play a role.

In both cosmetics and medicine the skin is the main target to be irradiated, but other targets of the human or animal body can also be accessed by phototherapy. These targets include, but are not limited to, the eye, wounds, nails, and internal parts of the body. Light can also be used in order to facilitate or support disinfection of wounds, beverages, nutrition, for example.

One effect of phototherapy is the stimulation of metabolism in the mitochondria. Certain wavelengths of light stimulate cytochrome c oxidase, an enzyme which is responsible for the production of the essential cellular energy in the form of adenosine triphosphate (ATP). ATP is required for cellular energy transfer in order to drive thermodynamically unfavoured biochemical reactions and as cellular energy storage. ATP can also act as signal molecule in order to modulate other biochemical molecules (e.g. reactive oxygen species and nitric oxide) that lead to ageing and cell death (oxidative stress). After phototherapy, the cells show an increased metabolism, they communicate better and they survive stressful conditions in a better way.

Such principle can be applied for medicinal therapeutic and cosmetic applications, such as wound healing, connective tissue repair, tissue repair, prevention of tissue death, relief of inflammation, pain, acute injuries, chronic diseases, metabolic disorders, neurogenic pain and seasonal effect disorders.

Another area of the application of light is the treatment of various cancers. In cancer therapy photodynamic therapy (PDT) plays an important role. In PDT light may be used in conjunction with a pharmaceutical. These therapies can be used to treat a variety of skin and internal diseases. In PDT, a light-sensitive therapeutic agent known as a photopharmaceutical is supplied externally or internally to an area of the body which is to be treated. That area is then exposed to light of a suitable frequency and intensity to activate the photopharmaceutical. A variety of photopharmaceutical agents are currently available. For example there are topical agents such as 5-aminolevulinic acid hydrochloride (Crawford Pharmaceuticals), methylaminolevulinic acid (Metfix®, Photocure). There are also injectable drugs used primarily for internal malignancies, including Photofin® (from Axcan) and Foscan® (from Biolitech Ltd). Often, the drug is applied in a non-active form that is metabolized to a light-sensitive photopharmaceutical.

In photodynamic therapy, the primary technique for supplying light to the photopharmaceutical is to project light of a suitable wavelength from standalone light sources such as lasers or filtered arc lamps. These sources are cumbersome and expensive, and are therefore only suitable for use in hospitals. This leads to inconvenience for the patient, and high cost for the treatment. High light irradiances are needed in order to treat an acceptable number of patients per day (for the treatment to be cost effective) and to avoid unduly inconveniencing the patient.

To date, phototherapy and PDT is dominated by the application of large light sources being uncomfortable for patients leading to low compliance. Many of the devices which are currently in use are only applicable stationary and require the control of medical professionals, e.g. in hospital or in doctor's surgery. Furthermore, many of the light sources currently used irradiate large areas of the subject to be treated, even if only a fraction of it should have been irradiated which may lead to unwanted side effects.

WO 98/46130 and U.S. Pat. No. 6,096,066 disclose arrays of LEDs for use in photodynamic therapy. The small LED sources taught therein result in uneven light incident on the patient. Fabrication of arrays is complicated because of the large number of connections required. The devices shown therein are designed for hospital treatment.

GB 2360461 discloses a flexible garment which uses a conventional photodynamic therapy light source to produce light which is then transmitted through optical fibres. As such light sources are heavy, the device is not ambulatory and is limited to hospital use.

U.S. Pat. No. 5,698,866 discloses a light source using over-driven inorganic LEDs. The resulting light output is not even. A heat-sinking mechanism is required, and the device is suitable only for hospital treatment.

WO 93/21842 discloses light sources using inorganic LEDs. Although transportable, the device is not suitable for ambulatory use by a patient at home and clinical treatment is envisaged.

According to U.S. Pat. No. 6,283,956 LEDs are used for reduction, elimination or stimulation of hair growth.

An essential prerequisite for the application of light in the fields mentioned above is the device. The commercial available systems nowadays are mostly based on lasers. However, theses systems are hospital based, i.e. stationary devices. In order to reduce costs and to increase convenience as well as compliance a portable home-use technology is required. In fact, some research has been devoted in this direction.

Rochester et al. disclosed in GB 24082092a flexible medical light source including flexible light emitting diodes form on flexible substrate and resulting diagnostic devices directed to monitoring blood characteristics (e.g. levels of CO, oxygen, or bilirubin) and photo-therapeutic devices for treatment of ailments.

Vogler Klaus and Kallert Heiko disclosed in EP 01818077a device for the treatment of skin. The device includes an potentially flexible organic light emitting diode (OLED) as light source. The device can be integrated in clothes or plaster.

Attili et al. (Br. J. Dermatol. 161(1), 170-173. 2009) published a clinical open pilot study of ambulatory photodynamic therapy (PDT) using a wearable low-irradiance OLEDs in the treatment of nonmelanoma skin cancer, suggesting that OLED-PDT is less painful than conventional PDT with the added advantage of being lightweight, and therefore has the potential for more convenient PDT at home.

Samuel et al. disclosed in EP 1444008B1 an ambulatory device for the use in a therapeutic and/or cosmetic treatment, the device includes an OLED and poly(p-phenylene vinylene) (PPV) used as an example.

EP 1444008 discloses the Devices for the treatment of photodynamic therapy including OLEDs.

Organic light emitting diodes have many advantages over their inorganic counterpart (light emitting diodes—LEDs) in that they are intrinsically flexible, and can be coated on large area by, for example, printing technologies, such as ink jet printing and screen printing.

However, in OLEDs active metals, such as Ba and Ca, are used as cathode. Therefore, OLEDs require excellent encapsulation to ensure long lifetime both in storage and in operation. Overall the production of OLEDs, a multilayer structure with each of several tons of nanometers, is still an elaborate and cost intensive task.

However, one drawback of OLEDs is the broad emission due to the nature of organic emitters, which may lead to energy loss or to unwanted side effects. The broad emission spectrum of OLEDs is not only unwanted in phototherapeutical applications but also in other technical fields such as display and lighting applications. For example, for display application, organic emitters usually have a low color purity.

Another drawback of organic emitters in OLED is the limited quantum efficiency. According to quantum statistics, three triplets per singlets are formed in the OLED if the probability of exciton formation is not spin-dependent. The probability of singlet exciton formation for devices based on fluorescent materials is only 25%. Hence, a fundamental limit of an internal quantum efficiency of 25% is put on OLED which are solely based on singlet emitters. This limit can be overcome by incorporating phosphorescent dopants, also called triplet emitters, usually complexes containing a heavy metal, which can increase spin-orbital coupling and harvest both singlet and triplet excitons. However, the metal complex is difficult to synthesize and it has stability problems. So far, a stable (deep) blue triplet emitter is still elusive. Moreover, because the triplet level of the organic materials is typically at least 0.5 eV higher than singlet level, a blue triplet emitter having itself a big band-gap (or HOMO-LUMO gap) will put extremely hard requirements on host materials and the charge transport materials in the adjacent layers.

On the other hand, another class of emissive material, so-called quantum dot or mono-dispersive nanocrystal as described below, has also drawn considerable attention in the last years. The advantages of quantum dot are: 1) theoretical internal quantum efficiency as high as 100%, compared to 25% of the singlet organic emitter; 2) soluble in common organic solvents; 3) emission wavelength can be easily tuned by the core size; 4) narrow emission spectrum; 5) intrinsic stability in inorganic materials.

The first mono-dispersive nanocrystals including a semiconducting material, also referred to herein as quantum dots or QDs, were based on CdE (E=S, Se, Te) and were produced using the so called TOPO (trioctyl phosphine oxide) method by Bawendi and later modified by Katari et al. A review on synthesis of QDs is given by Murray, Norris and Bawendi, "Synthesis and characterization of nearly monodisperse CdE (E=sulfur, selen, tellurium) semiconductor nanocrystallites", J. Am. Chem. Soc. 115 [19], 8706-8715, 1993. The mostly-reported caps of quantum dots are based on trioctylphosphine oxide (TOPO) or trioctylphosphine (TOP), which are supposed to have electron transporting properties.

The first light-emitting diode based on CdSe QDs was reported by Alivisatos et al., "Light emitting diodes made from cadmium selenide nanocrystals and a semiconducting polymer", Nature (London) 370[6488], 354-357, 1994, where a multilayer consisting of QDs was sandwiched between PPV (poly(p-phenylene-vinylene)) and an electrode, giving emission in red upon applying voltage. Bulovic et al., "Electroluminescence from single monolayers of nanocrystals in molecular organic devices", Nature (London) 420[6917], 800-803, 2002 describe use of a single monolayer of CdSe QDs sandwiched between two organic layers.

Leger et al, (Abstract of the 64$^{th}$ Northwest Regional Meeting of the American Chemical Society, Tacoma, Wash., United States, Jun. 28 to Jul. 1, 2009) disclosed a light emitting electrochemical cell including conjugated polymer and quantum dots with promising results. However, though conjugated polymers can easily be coated from solution, the performance of polymer OLEDs/OLECs is far behind that of OLEDs based on evaporated small molecule (SM) OLEDs. Furthermore, conjugated polymers have, due to the extended conjugation, in general a quite low triplet level. No conjugated polymer matrix for green triplet OLEDs has been reported or disclosed so far.

Therefore, the object of the present invention is to provide an improved electronic device and method for treatment of cells and cell tissue.

In one embodiment, a cells and/or cell tissue treatment device is provided, including at least one light source chosen from a light emitting electrochemical cell (OLEC), a light emitting electrochemical cell including at least one quantum dot (QD-LEC), and a organic light emitting device including at least one quantum dot (QD-OLED).

According to another embodiment, a kit of parts for treatment of cells and/or cell tissue includes a device of any of the preceding claims and a topical composition or a topical chromophore composition.

A further embodiment provides use of a device or of a kit of parts of any of the preceding claims for cosmetic treatment; prophylactic treatment; therapeutic treatment; non-invasive treatment; activation, stimulation, deactivation, disinfection, depilation, phototherapy, photodynamic therapy, extracorporeal treatment, intracorporeal treatment of cells and/or cell tissue; peeling and/or lifting of cell tissue; and/or activation or inhibition of the differentiation of stem cells.

In a further embodiment, a method for treatment of cells and/or cell tissue is provided, including exposing cells or cell tissue to light emitted from a cells and/or cell tissue treatment device including at least one light source chosen from an organic light emitting electrochemical cell (OLEC), a light emitting electrochemical cell including at least one quantum dot (QD-LEC), and a organic light emitting device including at least one quantum dot (QD-OLED).

The invention provides a cells and/or cell tissue treatment device whose emission wavelengths can precisely be tailored. Thus, color purity of the emission is improved. Further, the cells and/or cell tissue treatment device has high efficiency and small energy loss in the ultraviolet (UV) and/or infrared (IR) region of the spectrum. Further, the cells and/or cell tissue treatment device can be used in different technical fields of treatment of cells and cell tissue, such as phototherapy and/or PDT. The cells and/or cell tissue treatment device can easily be produced. The cells and/or cell tissue treatment device is user friendly particularly with regard to phototherapeutical applications, which is mainly due to its size, potential device flexibility, and adaptable size, shape, irradiation wavelength and intensity of the irradiation. Surprisingly, using the cells and/or cell tissue treatment device of embodiments allows effective and target-oriented treatment of cells and/or cell tissue.

An OLEC typically includes two electrodes, and a mixture or blend of electrolyte and fluorescent species in between, as firstly reported by Pei & Heeger in Science (1995), 269, 1086-1088. The underlying technology of OLECs differs from the ones of OLEDs or LEDs. Both OLEDs and LEDs are diodes with forward bias and reverse bias. In contrast to OLECs the I-V (current-voltage) curves of both OLEDs and LEDs are asymmetric. They represent semiconductor technologies whereas an OLEC is basically an electrochemical or more precisely an electrolytic cell. Charge transport in OLEDs occurs via the movement of holes and electrons from molecule to molecule until holes and electrons form so called excitons, i.e. electron-hole-pairs. Light is emitted when electrons and holes recombine. In OLECs, upon applying a voltage, the electrolyte is oxidized at the anode and reduced at the cathode.

Surprisingly, organic light emitting electrochemical cells (OLECs) can be used as light sources for the treatment of cells and cell tissue. OLECs are very simple in their structure and therefore easily prepared. The preparation of devices with curved or three dimensional surfaces is in the case of OLECs less complex as compared to the preparation of such surfaces in OLEDs. This is due to the fact that the requirements relating to homogeneity of the layer is less stringent. Thus, the production costs in particular for mass production are much lower as compared to the ones of OLEDs. Furthermore, OLECs do not rely on air-sensitive charge-injection layers or metals such as Ba or Cs for electron injection, which further simplifies their preparation and makes them more cost efficient, as compared to OLEDs. This is due to the less stringent requirements for encapsulation of OLECs.

The molecular cations and anions diffuse under the electrical field and in the meanwhile doping the organic emissive materials until they meet together to form a so called p-n junction. Further an exciton is formed on the organic emissive compounds in the p-n junction. The radiative decay of the exciton leads to the emission of light. The original work and the principle of OLECs can be referred to the paper by Qibing Pei et al., Science, 1995, 269, 1086-1088. The OLECs shows symmetric I-V curves, have low driving voltages, and there is no need for active metals as cathode.

According to embodiments, the OLEC can include between the two electrodes a composition for the treatment and/or prophylaxis of therapeutic diseases and/or cosmetic conditions, characterized in that the composition includes at least one ionic species and at least one organic electroluminescent compound. The composition can include at least one organic electroluminescent compound selected from fluorescent emitter materials, phosphorescent emitter materials, and emissive organo metallic complexes. Further, the ionic species may be cationic or anionic.

A QD-OLEC according to embodiments includes between the two electrodes a mixture or blend of electrolyte and fluorescent species, such as above composition for the treatment and/or prophylaxis of therapeutic diseases and/or cosmetic conditions, which contains at least one quantum dot.

The OLEC or QD-OLEc of embodiments may have the form of a fiber (OLEFC, QD-OLEFCS). For example, the OLEFC or QD-OLEFCS includes a fiber core which is flexible or rigid. The fiber core may have an outer first electrode; an emissive layer (EML) including at least one organic electroluminescent compound and at least one ionic species and positioned over the outer surface of the said first electrode; and a radiation transmissive second electrode positioned over the organic light emitting layer. Further, the fiber may have a circular, oval, or polygonal cross section or a combination thereof. The OLEFC or QD-OLEFCS may contain at least one organic electroluminescent compound selected from fluorescent emitter materials, phosphorescent emitter materials, and emissive organo metallic complexes. The organic electroluminescent compound may include at least one host material and at least one emitter material, wherein the host material is preferably selected from anthracenes, benzanthracenes, ketones, carbazoles, triarylamines, indenofluorenes, fluorenes, spirobifluorenes, phenanthrenes, dihydrophenanthrenes, thiophenes, triazines, imidazoles, isomers and derivatives thereof. Further, the OLEFC or QD-OLEFC may contain at least one further functional material selected from hole transport materials (HTM), hole injection materials (HIM), electron transport materials (ETM), and electron injection materials (EIM) and/or at least one ionic transition-metal complex (iTMC).

Quantum dots can be used in OLECs and OLEDs in connection with organic functional materials such as emitters, host materials, hole transport materials, hole injection materials, electron transport materials, and electron injection materials. Quantum dots can easily be produced and have a narrow emission spectrum in contrast to organic fluorescent or phosphorescent compounds. They can be tailored in terms of size which determines the quantum dot's emission maximum. High photoluminescent efficiency can also be obtained with quantum dots. Furthermore their emission intensity can be tailored by their concentration employed. Moreover, quantum dots are soluble in many solvents or can easily be made soluble in common organic solvents, allowing versatile processing methods, particularly printing methods such as screen printing, offset printing, and ink jet printing.

Surprisingly, LECs and/or OLEDs, each containing at least one quantum dot, can be used as light sources for the treatment of cells and cell tissue. The cells and cell tissue treatment device of embodiments may include a light emitting electrochemical cell including at least one quantum dot (QD-LEC). In other embodiments, the cells and cell tissue treatment device of embodiments may include an organic light emitting device including at least one quantum dot (QD-OLED). The OLEC, QD-LEC and/or QD-OLED of embodiments may further include at least one ionic compound and/or at least one small organic functional materials selected from host materials, fluorescent emitters, phosphorescent emitters, hole transport materials (HTMs), hole injection materials (HIMs), electron transport materials (ETMs), and electron injection materials (EIMs).

In general, a quantum dot is a semiconductor whose excitons are confined in all three spatial dimensions. As a result, they have properties that are between those of bulk semiconductors and those of discrete molecules. There are several ways to prepare quantum dot structures, for example by chemical methods or by ion implantation, or in nanodevices made by state-of-the-art lithographic techniques. The quantum dots of the present invention refer to colloidal semiconductor nanocrystals, also known as colloidal quantum dots, or nanodots or nanocrystals, which are produced by chemical methods.

The first mono-dispersive colloidal quantum dots including a semiconducting material were based on CdE (E=S, Se, Te) and were produced using the so called TOPO (trioctyl phosphine oxide) method by Bawendi and later modified by Katari et al. A review on synthesis of QDs is given by Murray, Norris and Bawendi, "Synthesis and characterization of nearly monodisperse CdE (E=sulfur, selen, tellurium) semiconductor nanocrystallites", J. Am. Chem. Soc. 115 [19], 8706-8715, 1993. While any method known to the skilled person can be used to create QDs, preferably a solution-phase colloidal method for controlled growth of inorganic QDs is used. The said colloidal methods are disclosed, e.g., by Alivisatos, A. P., "Semiconductor clusters, nanocrystals, and quantum dots," Science 271:933 (1996); X. Peng, M. Schlamp, A. Kadavanich, A. P. Alivisatos, "Epitaxial growth of highly luminescent CdSe/CdS Core/Shell nanocrystals with photostability and electronic accessibility," J. Am. Chem. Soc. 30:7019-7029 (1997); and C. B. Murray, D. J. Norris, M. G. Bawendi, "Synthesis and characterization of nearly monodisperse CdE (E=sulfur, selenium, tellurium) semiconductor nanocrystallites," J. Am. Chem. Soc. 115:8706 (1993). These methods allow low cost processability without the need for clean rooms and expensive manufacturing equipment. In these methods, metal precursors that undergo pyrolysis at high temperature are rapidly injected into a hot solution of organic surfactant molecules. These precursors break apart at high temperatures and react to nucleate nanocrystals. After this initial nucleation phase, a growth phase begins by the addition of monomers to the growing crystal. Thus, crystalline nanoparticles are obtained in solution that has an organic surfactant molecule coating their surface.

In these methods, synthesis occurs as an initial nucleation event that takes place over seconds, followed by crystal growth at elevated temperature for several minutes. Parameters such as the temperature, types of surfactants present, precursor materials, and ratios of surfactants to monomers can be modified so as to change the nature and progress of the reaction. The temperature controls the structural phase of the nucleation event, rate of decomposition of precursors, and rate of growth. The organic surfactant molecules mediate both solubility and control of the nanocrystal shape. The ratio of surfactants to monomer, surfactants to each other, monomers to each other, and the individual concentrations of monomers strongly influence the kinetics of growth.

A typical sequence of layers as found in an OLED is for example:
optionally a first substrate,
an anode layer,
optionally a hole injection layer (HIL),
optionally a hole transport layer (HTL) and/or an electron blocking layer (EBL),
an emissive or active layer, which upon electrical or optical exciation, produces excitons,
optionally an electron transport layer (ETL) and/or a hole blocking layer (HBL),
optionally an electron injection layer (EIL),
a cathode layer,
optionally a second substrate.

The sequence of the above given layer structure is an example. Other sequences are possible.

A QD-OLED according to embodiments may be an electronic device including a cathode, an anode, an emissive layer, wherein the emissive layer includes at least one quantum dot and at least one organic host material.

In a QD-OLED, in order to make high internal quantum efficiency (theoretical maximum of 100%) of quantum dot possible, it is highly desired that the exciton is formed directly on the quantum dot instead of on the organic host. According to embodiments of a QD-OLED, this can be realised by using an active layer or emissive layer wherein either the ionisation potential (valence band or VB) of the said quantum dot is at least 0.3 eV higher than the HOMO of the organic host, or the electron affinity (conduction band or CB) of the quantum dot is at least 0.3 eV lower than the LUMO of the organic host. The organic host has preferably a bigger band gap than the quantum dot.

The concentration of the QD in the QD-OLED of embodiments may be from 0.5 to 20 vol %, preferably from 1 to 15 vol %, very preferably from 2 to 10 vol %, and mostly preferably 2 to 5 vol %. In the most preferred embodiment, the concentration of the quantum dot is so adjusted that it works as hole trap or electron trap in the organic host. In one preferred embodiment, the quantum dot has an electron affinity at least 0.3 eV, more preferably 0.4 eV, very preferably 0.5 eV lower that the LUMO of the organic host. In this embodiment, the quantum dot works as electron trap or deep electron trap.

For embodiments of QD-OLEDs, it is desired to use the available standard quantum dots, which have usually deep HOMO and deep LUMO as mentioned before. The suitable organic host should also have either deep HOMO or deep LUMO or both. In one preferred embodiment, the organic host has a LUMO lower than −3.0 eV, more preferably lower than −3.5 eV, and particularly preferably lower than −4.0 eV. In another preferred embodiment, the organic host has a HOMO lower than −5.7 eV, more preferably lower than −6.0 eV, and particularly preferably lower than −6.2 eV.

The deep HOMO or deep LUMO organic host can be selected from compounds including strong electron-withdrawing group(s), which can be preferably selected from halogen, nitrile, carbonyl and nitro groups, for example —F, —CN, —CO, and —NO$_2$. The deep HOMO or deep LUMO organic host can be selected from a small molecule, an oligomer, a polymer and dendrimer, or a combination thereof.

Preferably, the hole injection layer or charge generation layer is transparent, e.g. transparent for outcoupling light or incident light.

A hole injection layer or charge generation layer suitable for embodiments can be selected from a charge generation layer or an intermediate connector layer for tandem OLEDs, as disclosed for example in U.S. Pat. No. 7,564,182 and US 2006/0240277A1.

According to one embodiment, in the QD-OLED the hole injection layer or charge generation layer is selected from or includes one or more transition metal oxides. In a further embodiment, the hole injection layer is preferably selected from or include vanadium oxide (VO$_x$), molybdenum oxide (MoO$_x$), ruthenium oxide (RuO$_x$) and tungsten oxide (WO$_x$).

In embodiments, the charge generation layer is a single layer, including organic or inorganic compound. Preferably the charge generation layer is an inorganic layer, which may enable emissive layer being coated from solution on top of that. The suitable inorganic charge generation material can be selected from transition metal oxides (TMOs). Particularly preferred TMOs are those having a work function higher than 5.6 eV or more, such as vanadium oxide (VO$_x$), molybdenum oxide ($MoO_x$), ruthenium oxide ($RuO_x$) and tungsten oxide ($WO_x$). The use of $VO_x$, $MoO_x$, $RuO_x$ as hole injection layer in OLEDs can be referred to the reported by Tokito et al., in J. Phys. D: Appl. Phys. 29 (1996) 2750. And tungsten oxide ($WO_x$) as hole injection layer was reported for example by Hoping et al., in Appl. Phys. Lett. 92, 213306 (2008). The work function of the transition metal oxides can be measured by Kelvin-probe measurements, for example $WO_3$ has a work function 6.4 eV as reported in Appl. Phys. Lett. 91, 113506 (2007)) and, $MoO_3$ 6.7 eV as reported in (Appl. Phys. Lett. 95, 123301 (2009)).

A preferred QD-OLED structure including an inorganic charge generation layer has the following layer structure: substrate/anode/hole injection layer (HIL) or charge generation layer (CGL)/emissive layer (EML)/cathode. Optionally and also preferably, the device can further include an electron transport layer and/or buffer layer between EML and cathode, which may reduce the quenching from the cathode.

A further suitable charge generation material can be selected from organic compounds having an electron affinity higher than higher than 5.6 eV or more. The suitable organic charge generation material can be selected from organic p-dopants, which are used for p-doping in OLEDs. For a general principle of n- and p-doping, and the related materials please refer to Chem. Rev., 2007, 107 (4), 1233-1271. The suitable organic p-dopant is for example, but not limited to, selected from p-dopants as described below. A yet further suitable charge generation layer can be a photo-sensitive, particularly IR-sensitive charge generation layer.

A preferred QD-OLED structure including an organic charge generation layer has the following layer structure: substrate/cathode/EML/HIL or CGL/anode.

Optionally and also preferably, the QD-OLED of embodiments can further include an electron transport layer and/or buffer layer between EML and cathode, which may reduce the quenching from the cathode. This is because the organic p-dopants can usually be deposited by thermal vacuum evaporation.

According to other embodiments, the QD-OLED may be an electronic device including a cathode, an anode, an emissive layer, wherein the emissive layer includes a composition including one or more quantum dots and at least one organic emitter which is chosen from a small molecule emitter, a small molecule singlet emitter and a triplet emitter. The emission wavelength of at least one of the one or more quantum dots may be longer than the emission wavelength of the organic emitter. Further, the at least one quantum dot may have at least one absorption intensity maximum at a wavelength in a range of 450 to 900 nm; and/or wherein the organic emitter may have at least one emission intensity maximum at a wavelength in a range of 450 to 900 nm. The ratio of the at least one quantum dot and the organic emitter may be from 1:2 to 2:1 in volume, preferably from 0.01:1 to 0.2:1 in volume.

The QD-LECs and/or QD-OLEDs used in the cells and/or cell tissue treatment device according to the present invention can include as many quantum dots as required to achieve the desired effect. Preferably the QD-LECs and/or QD-OLEDs include less than 100, particularly preferably less than 70 and very particularly preferably less than 40 different quantum dots. In a further preferred embodiment the said array includes less than 20 different types of quantum dots.

In yet another embodiment the QD-LECs and/or QD-OLEDs according to the present invention include 4, preferably 3, particularly preferably 2, and very particularly preferably 1 quantum dot(s). Preference is given to QD-LECs and/or QD-OLEDs including one quantum dot.

A QD-LEC and/or QD-OLED according to the present invention preferably include the quantum dot(s) in each a concentration of at least 0.1 wt %, particularly preferably at least 0.5 wt %, and very particularly preferably of at least 3 wt % with respect to the total amount of the emissive layer of the LEC and/or OLED. In one embodiment the QD-LECs and/or QD-OLEDs according to the present invention include less than 15, preferably less than 10, particularly preferably less than 7, and very particularly preferably less than 5 small organic functional material(s).

The small organic functional materials, such as a small molecule emitter or small molecule singlet emitter, according to the present invention are materials which are commonly used in the field of organic electronics and which are well known to one skilled in the art. A preferred compilation of small organic functional materials is disclosed in EP 09015222.4 and EP 10002558.4. The term small organic functional materials refers to small molecules having the desired host, light emitting, hole injecting, hole transporting, electron injecting, and/or electron transporting properties.

A small molecule according to the present invention is a molecule which is not a polymer, oligomer, dendrimer, or a blend. In particular, repeating structures are absent in small molecules. The molecular weight of small molecules is typically in the range of polymers with a low number of repeating units, oligomers or less. The molecular weight of the small molecule may be preferably below 4000 g/mol, particularly preferably below 3000 g/mol, and very particularly preferably below 2000 g/mol.

Polymers may have 10 to 10000, particularly preferably 20 to 5000 and very particularly preferably 50 to 2000 repeating units. Oligomers may have 2 to 9 repeating units. The branching index of the polymers and oligomers is between 0 (linear polymer without branching) and 1 (completely branched dendrimer). The term dendrimer as used herein is defined according to M. Fischer et al. in Angew. Chem., Int. Ed. 1999, 38, 885.

The molecular weight ($M_w$) of the polymers may preferably be in the range of about 10000 to about 2000000 g/mol, particularly preferably in the range of about 100000 to about 1500000 g/mol, and very particularly preferably in the range of about 200000 to about 1000000 g/mol. The determination of $M_w$ can be performed according to standard techniques known to the person skilled in the art by employing gel permeation chromatography (GPC) with polystyrene as internal standard, for instance.

A blend may be a mixture including at least one polymeric, dendrimeric, or oligomeric component.

The term host, host material or matrix material refers to a material having a bigger energy gap as emitter, and have either electron or hole transport properties or both. In the case of singlet OLEDs, e.g. of cells and/or cell treatment device according to the present invention, it is highly desired that the absorption spectrum of emitter overlaps essentially with photoluminescent spectrum of the host to ensure energy transfer. The QD-LECs of the cells and/or cell treatment device according to the present invention may include at least one small molecular host. In principle any small molecule host or matrix material can be used according to the present invention.

The term emitter refers to a material which upon receiving excitonic energy optically or electronically undergoes radiative decay to emit light. Principally, there are two classes of emitters, fluorescent emitters and phosphorescent emitters. The term fluorescent emitter relates to materials or compounds which undergo a radiative transition from an excited singlet state to its ground state. Thus, fluorescent emitters are sometimes also called singlet emitters. The term phosphorescent emitter relates to luminescent materials or compounds which include transition metals, which also include rare earth metals, lanthanides and actinides. Phosphorescent emitters predominately emit light by spin forbidden transitions occur, e.g., transitions from excited triplet and/or quintet states. However, a certain fraction of light emitted by phosphorescent emitters may also be caused by light emitting transitions from singlet states.

The term dopant as employed herein is also used for the term emitter or emitter material. In principle any small molecule light emitting compound can be used according to the present invention.

The OLEC, QD-LEC and/or QD-OLED according to the present invention may include at least one small organic functional material selected from hole transport materials (HTM). A HTM is characterized in that it is a material or unit capable of transporting holes (i.e. positive charges) injected from a hole injecting material or an anode.

The OLEC, QD-LEC and/or QD-OLED according to the present invention may include 4, preferably 3, particularly preferably 2, and very particularly preferably 1 HTM(s). Preference is given to QD-LECs including one HTM.

The OLEC, QD-LEC and/or QD-OLED according to the present invention preferably include the HTM(s) in each a concentration of at least 0.1 wt %, particularly preferably at least 2 wt %, and very particularly preferably of at least 10 wt % with respect to the total amount of the hole transport layer.

The OLEC, QD-LEC and/or QD-OLED according to the present invention may include at least one small organic functional material selected from hole injection materials (HIM). A HIM refers to a material or unit capable of facilitating holes (i.e. positive charges) injected from an anode.

The OLEC, QD-LEC and/or QD-OLED according to the present invention include 4, preferably 3, particularly preferably 2, and very particularly preferably 1 HIM(s). Preference is given to QD-LECs including one HIM.

OLEC, QD-LEC and/or QD-OLED according to the present invention preferably include the HIM(s) in each a concentration of at least 0.1 wt %, particularly preferably at least 0.5 wt %, and very particularly preferably of at least 3 wt % with respect to the total amount of hole injection layer.

The OLEC, QD-LEC and/or QD-OLED according to the present invention may include at least one small organic functional material selected from electron transport materials (ETM). An ETM refers to a material capable of transporting electrons (i.e. negative charges) injected from an EIM or a cathode.

The OLEC, QD-LEC and/or QD-OLED according to the present invention include 4, preferably 3, particularly preferably 2, and very particularly preferably 1 ETM(s). Preference is given to QD-LECs including one ETM.

OLEC, QD-LEC and/or QD-OLED according to the present invention preferably include the ETM(s) in each a concentration of at least 0.1 wt %, particularly preferably at least 2 wt %, and very particularly preferably of at least 10 wt % with respect to the total amount of the electron transporting layer.

The OLEC, QD-LEC and/or QD-OLED according to the present invention may include at least one small organic functional material selected from electron injection materials (EIM). An EIM refers to a material capable of facilitating electrons (i.e. negative charges) injected from cathode into an organic layer.

The OLEC, QD-LEC and/or QD-OLED according to the present invention include 4, preferably 3, particularly preferably 2, and very particularly preferably 1 EIM(s). Preference is given to QD-LECs including one EIM.

OLEC, QD-LEC and/or QD-OLED according to the present invention preferably include the EIM(s) in each a concentration of at least 0.1 wt %, particularly preferably at least 0.5 wt %, and very particularly preferably of at least 3 wt % with respect to the total amount of the electron injection layer.

In some embodiments, the at least one element chosen from OLEC, QD-LEC, QD-OLED is adapted for activation, stimulation, deactivation, disinfection, depilation, phototherapy, extracorporeal treatment, and/or intracorporeal treatment of cells and/or cell tissue, and/or lifting of cell tissue.

Further, in embodiments the at least one element chosen from OLEC, QD-LEC, QD-OLED is adapted to emit multichromatic and/or narrowband light and/or light in the yellow wavelength range and/or light in the infrared wavelength range; and/or wherein the cells and/or cell tissue treatment device is a continuous wave and/or pulsed device.

In embodiments, the at least one element chosen from OLEC, QD-LEC, QD-OLED is adapted to emit a multichromatic light having a effective radiated power ratio of about 4:1 of yellow light to infrared light. For instance, at least one element chosen from OLEC, QD-LEC, QD-OLED is adapted to emit a multichromatic light including yellow light of about 590 nm at an effective radiated power of about 4 mW/cm$^2$ and infrared light of about 850 nm at an effective radiated power of about 1 mW/cm$^2$.

At least one element chosen from OLEC, QD-LEC, QD-OLED may be adapted to emit light at a wavelength from about 300 nm to about 1300 nm, and/or at a total energy fluence of less than 10 J/cm$^2$, and/or at pulses having a duration of from about 0.1 femtoseconds to about 100 seconds, and/or the interpulse delay being between said pulses being from about 0.1 to about 1000 milliseconds.

Embodiments of the cells and/or cell treatment device may include at least one further light source chosen from a light emitting diode, a laser, a fluorescent light source a light emitting polymer, a xenon arc lamp, a metal halide lamp, a filamentous light source, an intense pulsed light source, a sulfur lamp, and combinations thereof, wherein the at least one further light source is adapted to emit light at a wavelength from about 400 nm to about 1600 nm.

Moreover, embodiments of the cells and/or cell treatment device may include at least one element chosen from an ultrasound source, filter means adapted for reducing the intensity of infrared radiation received by the cells and/or cell tissue, filter means for selecting a wavelength or a wavelength band, and cooling means.

The device of any of the preceding claims, wherein the device is an ambulatory device and/or includes an attachment means for attaching the device to a patient.

In principle any small molecule EIM known to one skilled in the art can be employed according to the present invention. Further to EIM mentioned elsewhere herein, suitable EIMs include at least one organic compound selected from metal complexes of 8-hydroxyquinoline, heterocyclic organic compounds, fluorenones, fluorenylidene methane, perylenetetracarboxylic acid, anthraquinone dimethanes, diphenoquinones, anthrones, anthraquinonediethylene-diamines, isomers and derivates thereof can be used according to the invention.

Metal complexes of 8 hydroxyquinoline, such as, for example, $Alq_3$ and $Gaq_3$, can be used as EIM. A reducing doping with alkali metals or alkaline-earth metals, such as, for example, Li, Cs, Ca or Mg, at the interface to the cathode is advantageous. Preference is given to combinations which include Cs, for example Cs and Na, Cs and K, Cs and Rb or Cs, Na and K.

Heterocyclic organic compounds, such as, for example, 1,10-phenanthroline derivatives, benzimidazoles, thiopyran dioxides, oxazoles, triazoles, imidazoles or oxadiazoles, are likewise suitable. Examples of suitable five-membered rings containing nitrogen are oxazoles, thiazoles, oxadiazoles, thiadiazoles, triazoles, and compounds which are disclosed in US 2008/0102311 A1.

Preferred EIMs are selected from compounds with the Formulae (1) to (3), which may be substituted or unsubstituted.

Formula (5)

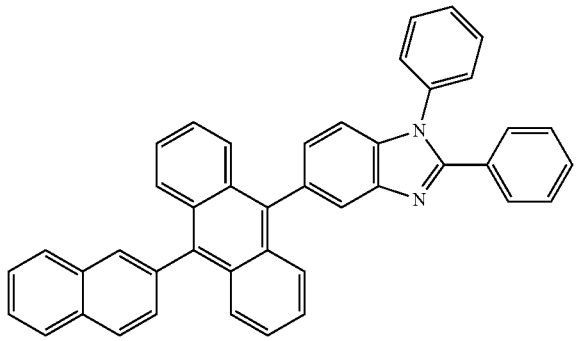

In principle any ETM known to one skilled in the art can be employed according to the present invention. Further to ETM mentioned elsewhere herein, suitable ETMs are selected from the group consisting of imidazoles, pyridines, Formula (1)

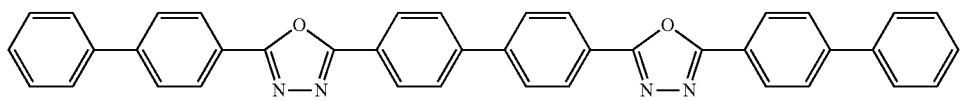

Formula (2)

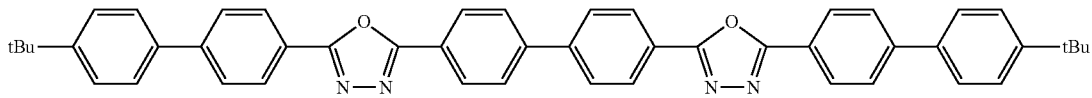

Formula (3)

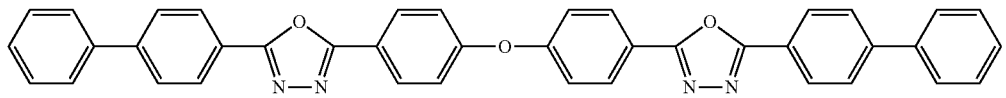

Organic compounds, such as fluorenones, fluorenylidene methane, perylenetetracarboxylic acid, anthraquinone dimethanes, diphenoquinones, anthrones and anthraquinonediethylenediamines, can also be employed, for example Formula (4)

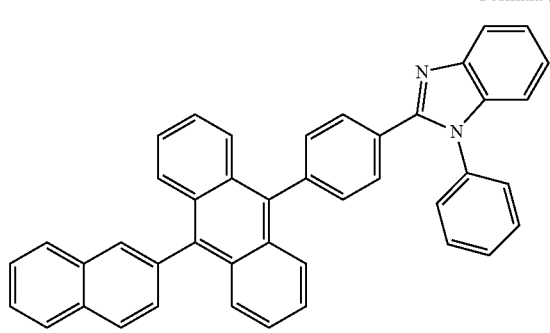

pyrimidines, pyridazines, pyrazines, oxadiazoles, chinolines, chinoxalines, anthracenes, benzanthracenes, pyrenes, perylenes, benzimidazoles, triazines, ketones, phosphinoxides, phenazines, phenanthrolines, triarylboranes, isomers and derivatives thereof.

Further suitable ETMs are selected from imidazoles, pyridines, pyrimidines, pyridazines, pyrazines, oxadiazoles, chinolines, chinoxalines, anthracenes, benzanthracenes, pyrenes, perylenes, benzimidazoles, triazines, ketones, phosphinoxides, phenazines, phenanthrolines, and triarylboranes.

Further suitable ETMs for electron-transporting layers are metal chelates of 8 hydroxyquinoline (for example Liq, $Alq_3$, $Gaq_3$, $Mgq_2$, $Znq_2$, $Inq_3$, $Zrq_4$), Balq, 4 azaphenanthrene-5-ol/Be complexes (U.S. Pat. No. 5,529,853 A; e.g. Formula (6)), butadiene derivatives (U.S. Pat. No. 4,356,429), heterocyclic optical brighteners (U.S. Pat. No. 4,539,507), benzazoles, such as, for example, 1,3,5-tris(2-N-phenylbenzimidazolyl)benzene (TPBI) (U.S. Pat. No. 5,766,779, Formula (7)), 1,3,5-triazines, pyrenes, anthracenes, tetracenes, fluorenes, spirobifluorenes, dendrimers, tetracenes, for example rubrene derivatives, 1,10-phenanthroline derivatives (JP 2003/115387, JP 2004/311184, JP 2001/267080, WO 2002/043449), silacyl-cyclopentadiene derivatives (EP 1480280, EP 1478032, EP 1469533), pyridine derivatives (JP 2004/200162 Kodak), phenanthrolines, for example BCP and Bphen, also a number of phenanthrolines bonded via biphenyl or other aromatic groups (US 2007/0252517 A1) or phenanthrolines bonded to anthracene (US 2007/0122656 A1, e.g. Formulae (8) and (9)), 1,3,4-oxadiazoles, for example Formula (10), triazoles, for example Formula (11), triarylboranes, for example also with Si, benzimidazole derivatives and other N heterocyclic compounds (cf. US 2007/0273272 A1), silacyclopentadiene derivatives, borane derivatives, Ga oxinoid complexes.

Preference is given to 2,9,10-substituted anthracenes (with 1- or 2-naphthyl and 4- or 3-biphenyl) or molecules which contain two anthracene units (US 2008/0193796 A1).

Formula (6)

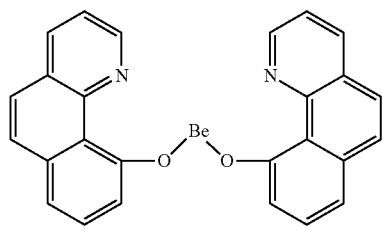

Formula (7)

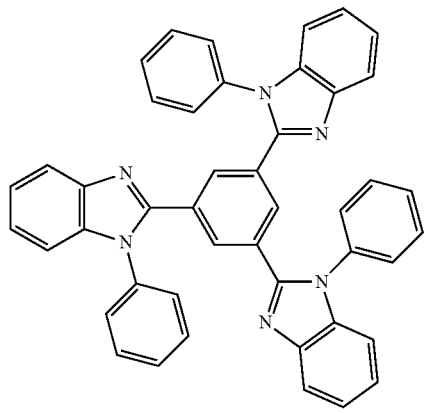

Formula (8)

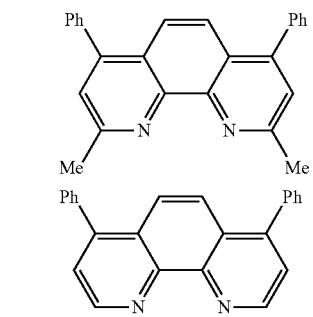

Formula (9)

Formula (10)

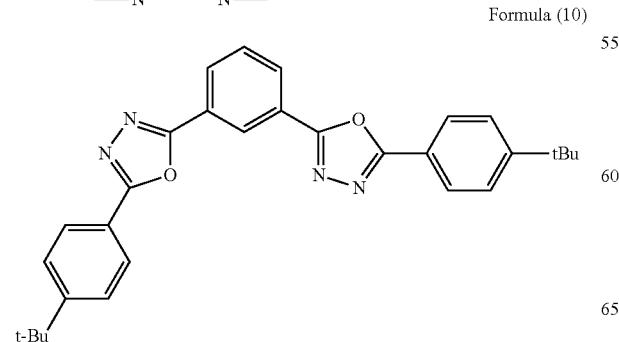

Formula (11)

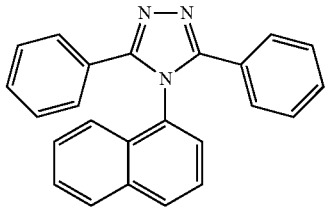

Preference is likewise given to anthracene-benzimidazole derivatives, such as, for example, the compounds of Formulae (12) to (14), and as disclosed in, e.g., U.S. Pat. No. 6,878,469 B2, US 2006/147747 A, and EP 1551206 A1.

Formula (12)

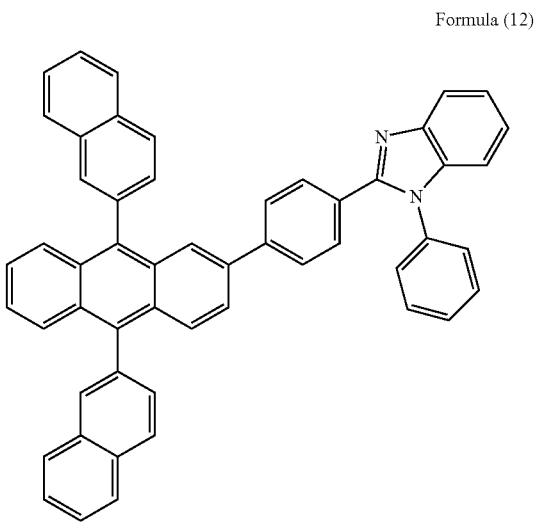

Formula (13)

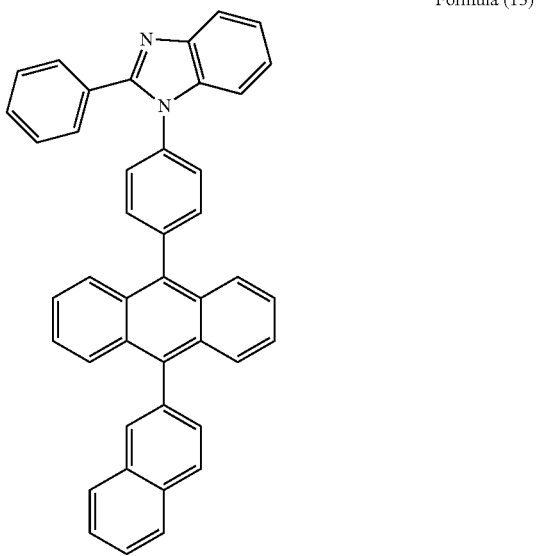

-continued

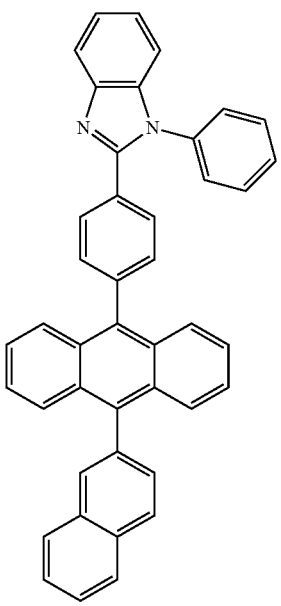

Formula (14)

Further to HIMs mentioned elsewhere herein, suitable HIMs are phenylenediamine derivatives (U.S. Pat. No. 3,615,404), arylamine derivatives (U.S. Pat. No. 3,567,450), amino-substituted chalcone derivatives (U.S. Pat. No. 3,526,501), styrylanthracene derivatives (JP Showa 54 (1979) 110837), hydrazone derivatives (U.S. Pat. No. 3,717,462), acylhydrazones, stilbene derivatives (JP Showa 61 (1986) 210363), silazane derivatives (U.S. Pat. No. 4,950,950), polysilane compounds (JP Heisei 2 (1990) 204996), PVK, porphyrin compounds (JP Showa 63 (1988) 2956965, U.S. Pat. No. 4,720,432), aromatic tertiary amines and styrylamines (U.S. Pat. No. 4,127,412), triphenylamines of the benzidine type, triphenylamines of the styrylamine type, and triphenylamines of the diamine type. Arylamine dendrimers can also be used (JP Heisei 8 (1996) 193191), as can phthalocyanine derivatives, naphthalocyanine derivatives, or butadiene derivatives, are also suitable.

Preferably, the HIM is selected from monomeric organic compound including amine, triarylamine, thiophene, carbazole, phthalocyanine, porphyrine and their derivatives.

Particular preference is given to the tertiary aromatic amines (US 2008/0102311 A1), for example N,N'-diphenyl-N,N'-di(3-tolyl)benzidine (=4,4'-bis[N-3-methylphenyl]-N-phenylamino)biphenyl (NPD) (U.S. Pat. No. 5,061,569), N,N'-bis(N,N'-diphenyl-4-aminophenyl)-N,N-diphenyl-4,4'-diamino-1,1'-biphenyl (TPD 232) and 4,4',4"-tris[3-methylphenyl)phenylamino]-triphenylamine (MTDATA) (JP Heisei 4 (1992) 308688) or phthalocyanine derivatives (for example H2Pc, CuPc, CoPc, NiPc, ZnPc, PdPc, FePc, MnPc, ClAlPc, ClGaPc, ClInPc, ClSnPc, Cl$_2$SiPc, (HO)AlPc, (HO)GaPc, VOPc, TiOPc, MoOPc, GaPc-O-GaPc).

Particular preference is given to the following triarylamine compounds of the Formulae (15) (TPD 232), (16), (17), and (18), which may also be substituted, and further compounds as disclosed in U.S. Pat. No. 7,399,537 B2, US 2006/0061265 A1, EP 1661888 A1, and JP 08292586A. Further compounds suitable as hole injection material are disclosed in EP 0891121 A1 and EP 1029909 A1. Hole injection layers in general are described in US 2004/0174116.

Formula (15)

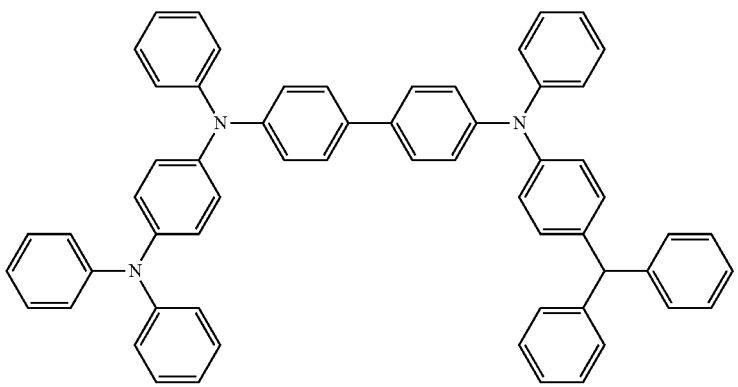

Formula (16)

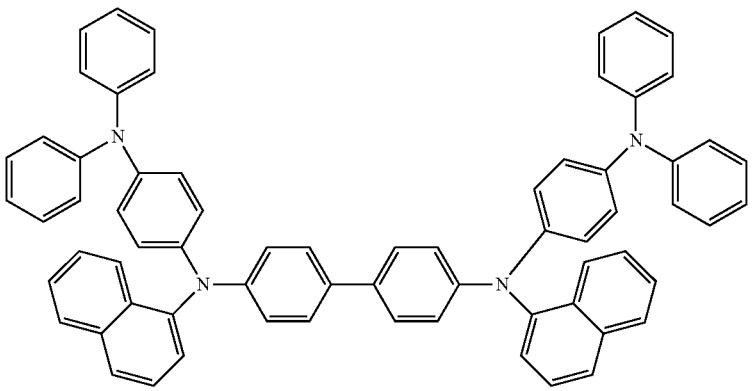

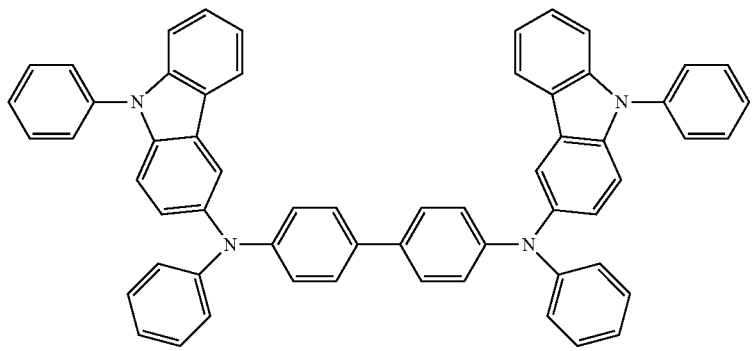

Formula (17)

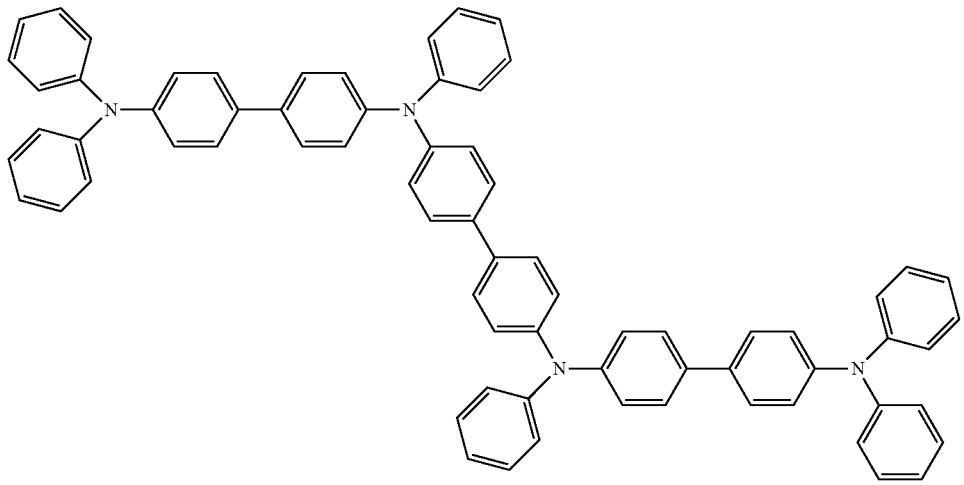

Formula (18)

In principle any HTM known to one skilled in the art can be employed in embodiments according to the present invention. Further to HTM mentioned elsewhere herein, HTM is preferably selected from amines, triarylamines, thiophenes, carbazoles, phthalocyanines, porphyrines, isomers and derivatives thereof. HTM is particularly preferably selected from amines, triarylamines, thiophenes, carbazoles, phthalocyanines, and porphyrines.

Suitable small molecule materials for hole-transporting are phenylenediamine derivatives (U.S. Pat. No. 3,615,404), arylamine derivatives (U.S. Pat. No. 3,567,450), amino-substituted chalcone derivatives (U.S. Pat. No. 3,526,501), styrylanthracene derivatives (JP A 56-46234), polycyclic aromatic compounds (EP 1009041), polyarylalkane derivatives (U.S. Pat. No. 3,615,402), fluorenone derivatives (JP A 54-110837), hydrazone derivatives (U.S. Pat. No. 3,717,462), stilbene derivatives (JP A 61-210363), silazane derivatives (U.S. Pat. No. 4,950,950), polysilanes (JP A 2-204996), aniline copolymers (JP A 2-282263), thiophene oligomers, polythiophenes, PVK, polypyrroles, polyanilines and further copolymers, porphyrin compounds (JP A 63-2956965), aromatic dimethylidene-type compounds, carbazole compounds, such as, for example, CDBP, CBP, mCP, aromatic tertiary amine and styrylamine compounds (U.S. Pat. No. 4,127,412), and monomeric triarylamines (U.S. Pat. No. 3,180,730).

Preference is given to aromatic tertiary amines containing at least two tertiary amine units (U.S. Pat. No. 4,720,432 and U.S. Pat. No. 5,061,569), such as, for example, 4,4'-bis[N-(1-naphthyl)-N-phenylamino]biphenyl (NPD) (U.S. Pat. No. 5,061,569) or MTDATA (JP A 4-308688), N,N,N',N'-tetra(4-biphenyl)diaminobiphenylene (TBDB), 1,1-bis(4-di-p-tolylaminophenyl)cyclohexane (TAPC), 1,1-bis(4-di-p-tolylaminophenyl)-3-phenylpropane (TAPPP), 1,4-bis[2-[4-[N,N-di(p-tolyl)amino]phenyl]vinyl]benzene (BDTAPVB), N,N,N',N'-tetra-p-tolyl-4,4'-diaminobiphenyl (TTB), TPD, N,N,N',N'-tetraphenyl-4,4'''-diamino-1,1':4',1'':4'',1'''-quaterphenyl, likewise tertiary amines containing carbazole units, such as, for example, 4 (9H-carbazol-9-yl)-N,N-bis[4-(9H-carbazol-9-yl)phenyl]benzeneamine (TCTA). Preference is likewise given to hexaazatriphenylene compounds in accordance with US 2007/0092755 A1.

Particular preference is given to the following triarylamine compounds of the Formulae (19) to (24), which may also be substituted, and as disclosed in EP 1162193 A1, EP 650955 A1, Synth. Metals 1997, 91(1-3), 209, DE 19646119 A1, WO 2006/122630 A1, EP 1860097 A1, EP 1834945 A1, JP 08053397 A, U.S. Pat. No. 6,251,531 B1, and WO 2009/041635.

Formula (19)
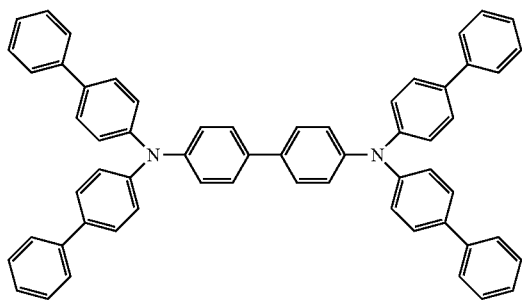
Formula (20)
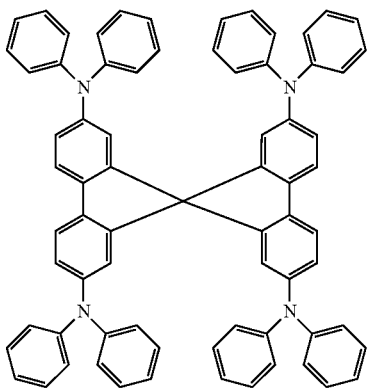
Formula (21)
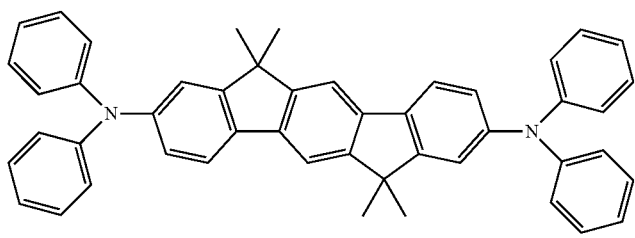
Formula (22)
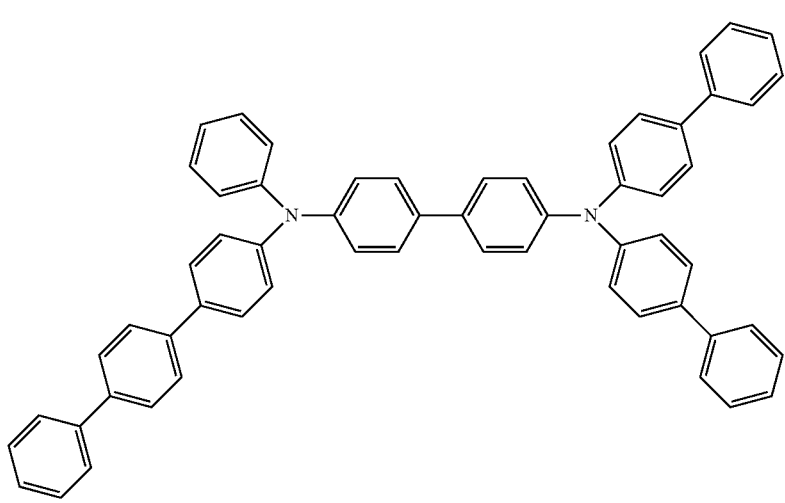

Formula (23)

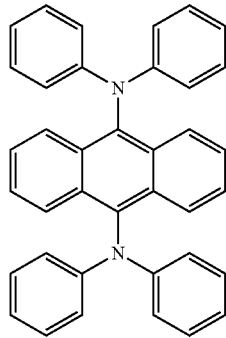

Formula (24)

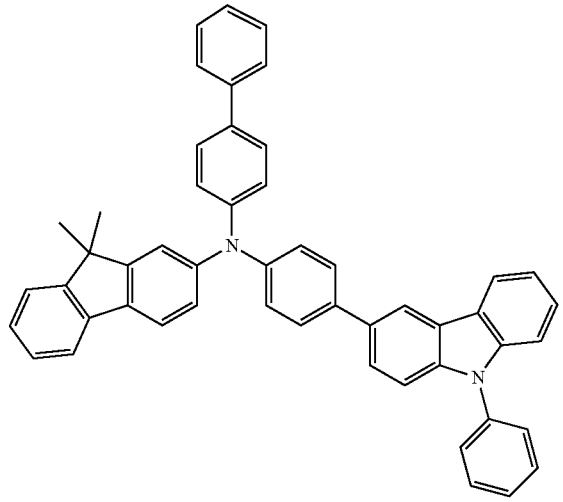

The OLEC, QD-LEC and/or QD-OLED contained in embodiments may include 4, preferably 3, particularly preferably 2, and very particularly preferably 1 host material(s). Preference is given to QD-LECs including one host material. If more than one host material is included, the term co-host is often used for additional host materials.

Preferred host materials suitable for embodiments, e.g. for fluorescent emitters of embodiments, are selected from anthracenes, benzanthracenes, indenofluorenes, fluorenes, spirobifluorenes, phenanthrenes, dehydrophenanthrenes, thiophenes, triazines, imidazole and derivatives thereof.

Particularly preferred host materials for fluorescent emitter are selected from the classes of the oligoarylenes (for example 2,2',7,7'-tetraphenyl-spirobifluorene in accordance with EP 676461 or dinaphthylanthracene), in particular the oligoarylenes containing condensed aromatic groups, such as, for example, phenanthrene, tetracene, coronene, chrysene, fluorene, spirofluorene, perylene, phthaloperylene, naphthaloperylene, decacyclene, rubrene, the oligoarylenevinylenes (for example 4,4'-bis(2,2-diphenyl-ethenyl)-1,1'-biphenyl (DPVBi) or 4,4-bis-2,2-diphenylvinyl-1,1-spirobi-phenyl (spiro-DPVBi) in accordance with EP 676461), the polypodal metal complexes (for example in accordance with WO 2004/081017), in particular metal complexes of 8 hydroxyquinoline, for example aluminium (III)tris(8-hydroxyquinoline) (aluminium quinolate, $Alq_3$) or bis(2-methyl-8-quinolinolato)-4-(phenylphenolinolato)aluminium, also with imidazole chelate (US 2007/0092753 A1) and quinoline-metal complexes, aminoquinoline-metal complexes, benzoquinoline-metal complexes, the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (e.g. DE 102007024850). Particularly preferred host materials are selected from the classes of the oligoarylenes, containing naphthalene, anthracene, benzanthracene and/or pyrene, or atropisomers of these compounds, the ketones, the phosphine oxides and the sulfoxides. Very particularly preferred host materials are selected from the classes of the oligoarylenes, containing anthracene, benzanthracene and/or pyrene, or atropisomers of these compounds. For the purposes of this invention, an oligoarylene is intended to be taken to mean a compound in which at least three aryl or arylene groups are bonded to one another.

Further preferred host materials for fluorescent emitter are selected, in particular, from compounds of the Formula (25)

$$Ar^4—(Ar^5)_p—Ar^6 \qquad \text{Formula (25)}$$

wherein
$Ar^4$, $Ar^5$, $Ar^6$ are on each occurrence, identically or differently, an aryl or heteroaryl group having 5 to 30 aromatic ring atoms, which may be substituted by one or more radicals and
p is 1, 2, or 3,
the sum of the π-electrons in $Ar^4$, $Ar^5$ and $Ar^6$ is at least 30 if p=1 and is at least 36 if p=2 and is at least 42 if p=3.

It is particularly preferred in the host materials of the Formula (25) for the group $Ar^5$ to stand for anthracene, which may be substituted by one or more radicals $R^1$, and for the groups $Ar^4$ and $Ar^6$ to be bonded in the 9 and 10-positions. Very particularly preferably, at least one of the groups $Ar^4$ and/or $Ar^6$ is a condensed aryl group selected from 1-or 2-naphthyl, 2-, 3- or 9-phenanthrenyl or 2-, 3-, 4-, 5-, 6- or 7-benzanthracenyl, each of which may be substituted by one or more radicals $R^1$. Anthracene-based compounds are described in US 2007/0092753 A1 and US 2007/0252517 A1, for example 2-(4-methylphenyl)-9,10-di-(2-naphthyl)anthracene, 9-(2-naphthyl)-10-(1,1'-biphenyl)anthracene and 9,10-bis[4-(2,2-diphenyl-ethenyl)phenyl]anthracene, 9,10-diphenylanthracene, 9,10-bis(phenyl-ethynyl)anthracene and 1,4-bis(9'-ethynylanthracenyl)benzene. Preference is also given to host materials containing two anthracene units (US 2008/0193796 A1), for example 10, 10'-bis[1,1',4',1"]terphenyl-2-yl-9,9'-bisanthracenyl.

Further preferred host materials are derivatives of arylamine, styrylamine, fluorescein, perynone, phthaloperynone, naphthaloperynone, diphenyl-butadiene, tetraphenylbutadiene, cyclopentadienes, tetraphenylcyclopentadiene, pentaphenylcyclopentadiene, coumarine, oxadiazole, bisbenzoxazoline, oxazone, pyridine, pyrazine, imine, benzothiazole, benzoxazole, benzimidazole (US 2007/0092753 A1), for example 2,2',2"-(1,3,5-phenylene)tris[1-phenyl-1H-benzimidazole]⁻, aldazines, stilbene, styrylarylene derivatives, for example 9, 10-bis[4-(2,2-diphenylethenyl)phenyl]anthracene, and distyrylarylene derivatives (U.S. Pat. No. 5,121,029), diphenylethylene, vinylanthracene, diaminocarbazole, pyran, thiopyran, diketopyrrolopyrrole, polymethine, mellocyanine, acridone, quinacridone, cinnamic acid esters and fluorescent dyes.

Particular preference is given to derivatives of arylamine and styrylamine, for example 4,4'-bis[N-(1-naphthyl)-N-(2-naphthyl)amino]biphenyl (TNB).

Preferred compounds with oligoarylene as hosts for fluorescent emitter are compounds as disclosed in, e.g., US 2003/0027016 A1, U.S. Pat. No. 7,326,371 B2, US 2006/043858 A, U.S. Pat. No. 7,326,371 B2, US 2003/0027016 A1, WO 2007/114358, WO 2008/145239, JP 3148176 B2, EP 1009044, US 2004/018383, WO 2005/061656 A1, EP 0681019B1, WO 2004/013073A1, U.S. Pat. No. 5,077,142, WO 2007/065678, and US 2007/0205412 A1. Particularly preferred oligoarylene-based compounds are compounds having the Formulae (26) to (32).

Formula (26)

Formula (27)

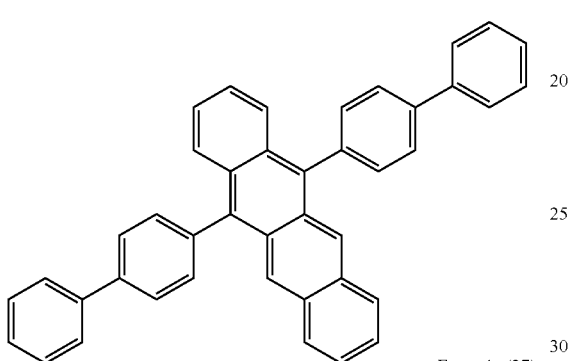

Formula (28)

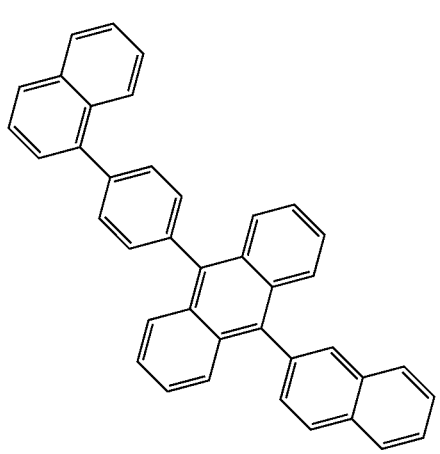

Formula (29)

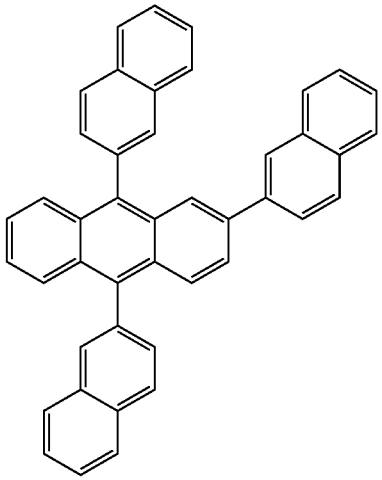

Formula (30)

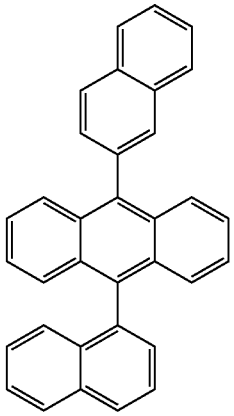

Formula (31)

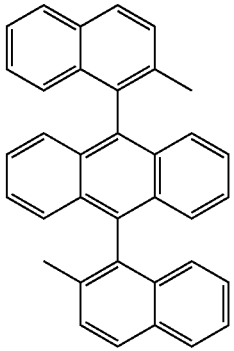

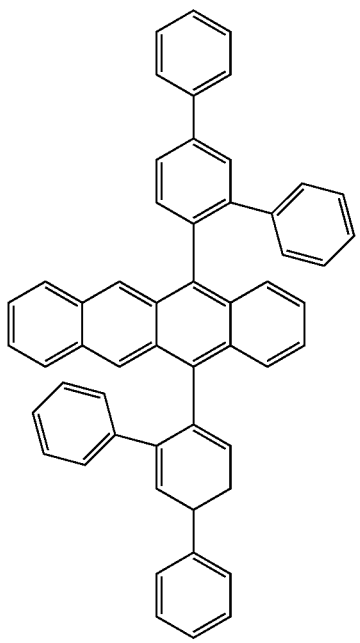

Formula (32)

Further host materials for fluorescent emitter can be selected from spirobifluorene and derivates thereof, for example Spiro-DPVBi as disclosed in EP 0676461 and indenofluorene as disclosed in U.S. Pat. No. 6,562,485.

The preferred host materials for phosphorescent emitter, i.e. matrix materials, are selected from ketones, carbazoles, indolocarbazoles, triarylamines, indenofluorenes, fluorenes, spirobifluorenes, phenantrenes, dehydrophenanthrenes, thiophenes, triazines, imidazoles and their derivatives. Some preferred derivatives are described below in more details.

If a phosphorescent emitter is employed the host material must fulfil rather different characteristics as compared to host materials used for fluorescent emitter. The host materials used for phosphorescent emitter are required to have a triplet level which is higher in energy as compared to the triplet level of the emitter. The host material can either transport electrons or holes or both of them. In addition, the emitter is supposed to have large spin-orbital coupling constants in order to facilitate singlet-triplet mixing sufficiently. This can be enabled by using metal complexes.

Preferred matrix materials are N,N-biscarbazolylbiphenyl (CBP), carbazole derivatives (for example in accordance with WO 2005/039246, US 2005/0069729, JP 2004/288381, EP 1205527 or DE 102007002714), azacarbazoles (for example in accordance with EP 1617710, EP 1617711, EP 1731584, JP 2005/347160), ketones (for example in accordance with WO 2004/093207), phosphine oxides, sulfoxides and sulfones (for example in accordance with WO 2005/003253), oligophenylenes, aromatic amines (for example in accordance with US 2005/0069729), bipolar matrix materials (for example in accordance with WO 2007/137725), silanes (for example in accordance with WO 2005/111172), 9,9-diarylfluorene derivatives (e.g. in accordance with DE 102008017591), azaboroles or boronic esters (for example in accordance with WO 2006/117052), triazole derivatives, oxazoles and oxazole derivatives, imidazole derivatives, polyarylalkane derivatives, pyrazoline derivatives, pyrazolone derivatives, distyrylpyrazine derivatives, thiopyran dioxide derivatives, phenylenediamine derivatives, tertiary aromatic amines, styrylamines, indoles, anthrone derivatives, fluorenone derivatives, fluorenylidenemethane derivatives, hydrazone derivatives, silazane derivatives, aromatic dimethylidene compounds, porphyrin compounds, carbodiimide derivatives, diphenylquinone derivatives, phthalocyanine derivatives, metal complexes of 8 hydroxyquinoline derivatives, such as, for example, $Alq_3$, the 8 hydroxyquinoline complexes may also contain triarylaminophenol ligands (US 2007/0134514 A1), various metal complex-polysilane compounds with metal phthalocyanine, benzoxazole or benzothiazole as ligand, hole-conducting polymers, such as, for example, poly(N-vinylcarbazole) (PVK), aniline copolymers, thiophene oligomers, polythiophenes, polythiophene derivatives, polyphenylene derivatives, polyfluorene derivatives.

Further particularly preferred matrix materials are selected from compounds including indolocarbazoles and their derivatives (e.g. Formulae (33) to (39)), as disclosed for examples in DE 102009023155.2, EP 0906947B1, EP 0908787B1, EP 906948B1, WO 2008/056746A1, WO 2007/063754A1, WO 2008/146839A1, and WO 2008/149691A1.

Formula (33)

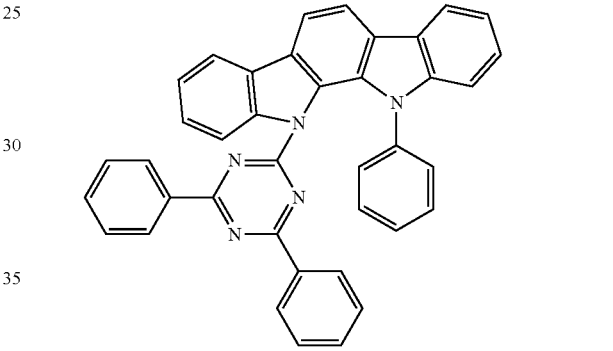

Formula (34)

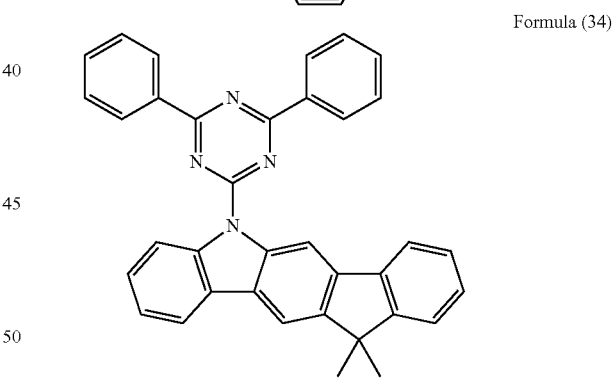

Formula (35)

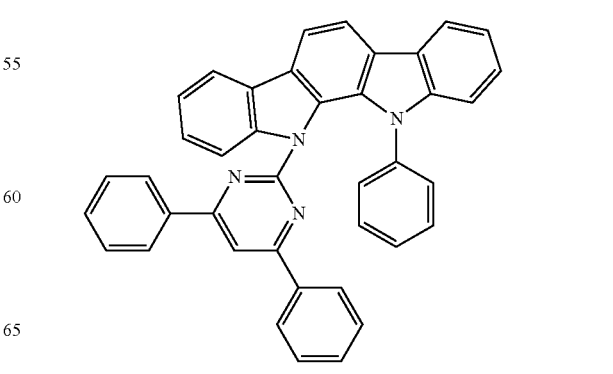

-continued

Formula (36)
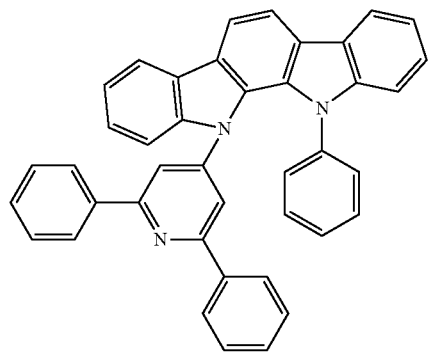

Formula (37)
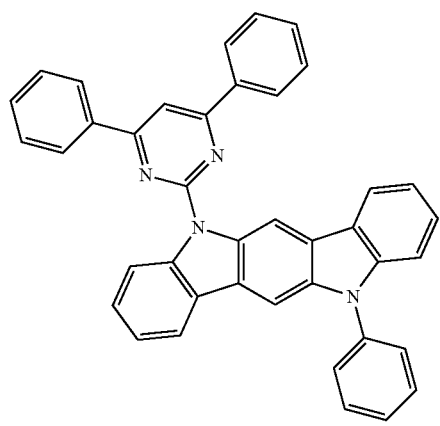

Formula (38)
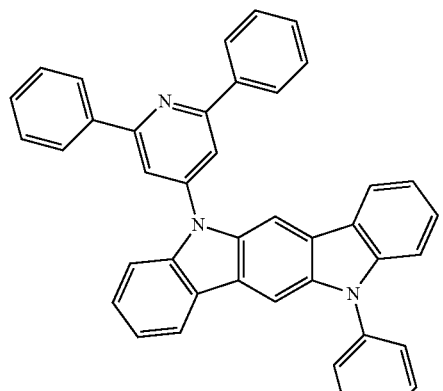

Formula (39)
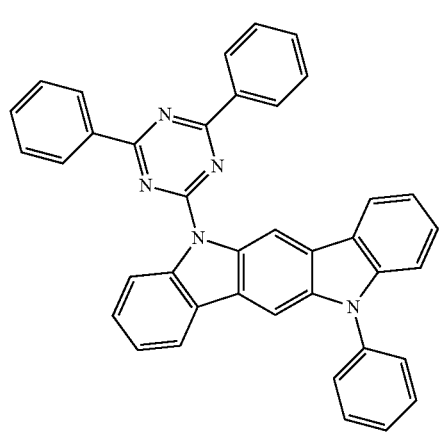

Examples of preferred carbazole derivatives are, 1,3-N,N-dicarbazole-benzene (=9,9'-(1,3-phenylene)bis-9H-carbazole) (mCP), 9,9'-(2,2'-dimethyl[1,1'-biphenyl]-4,4'-diyl)bis-9H-carbazole (CDBP), 1,3-bis(N,N'-dicarbazole)benzene (=1,3-bis(carbazol-9-yl)benzene), PVK (polyvinylcarbazole), 3,5-di(9H-carbazol-9-yl)biphenyl and compounds of the Formulae (40) to (44).

Formula (40)
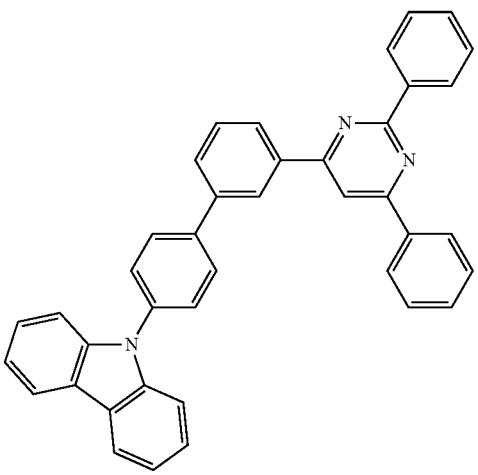

Formula (41)
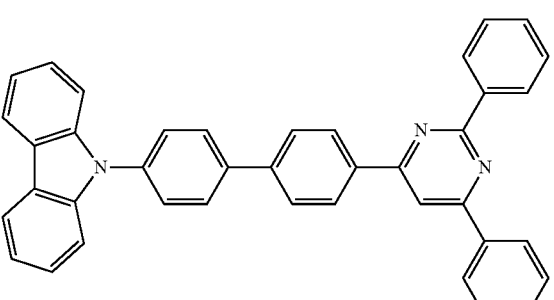

Formula (42)
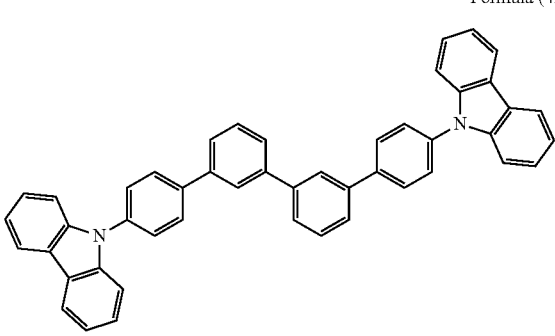

Formula (43)
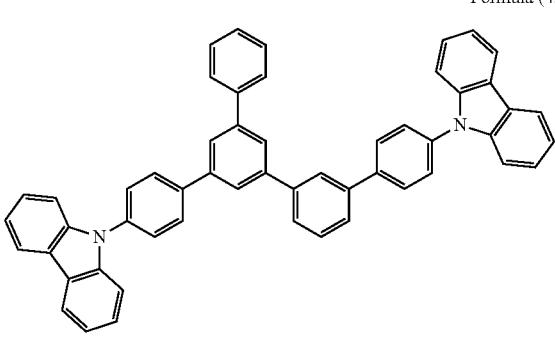

Formula (44)

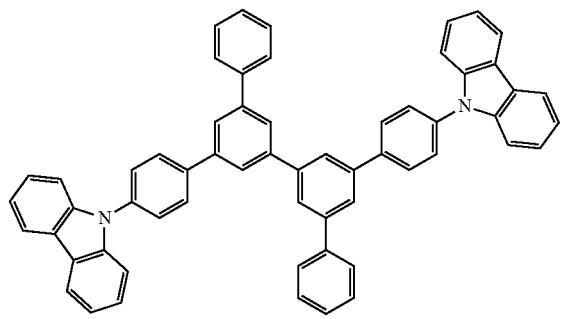

Preferred Si tetraaryl compounds are, for example, (US 2004/0209115, US 2004/0209116, US 2007/0087219 A1, US 2007/0087219 A1) the compounds of the Formulae (45) to (59).

Formula (45)

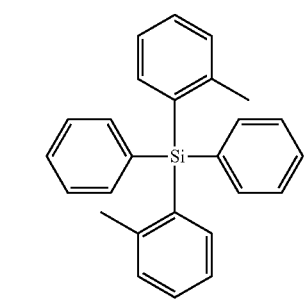

Formula (46)

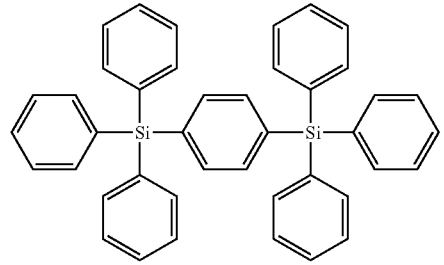

Formula (47)

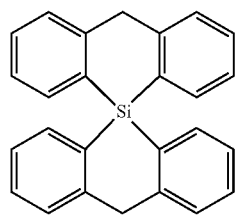

Formula (48)

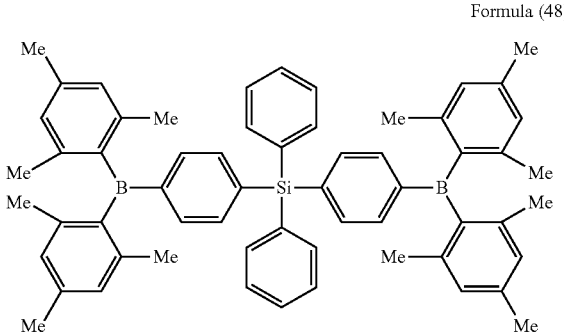

Formula (49)

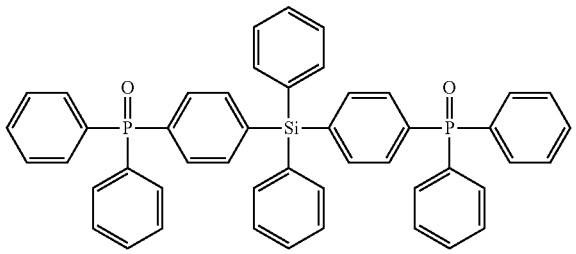

Formula (50)

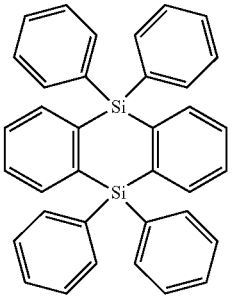

A particularly preferred matrix for phosphorescent dopants is the compound of Formula (51) (EP 652273 B1)

Formula (51)

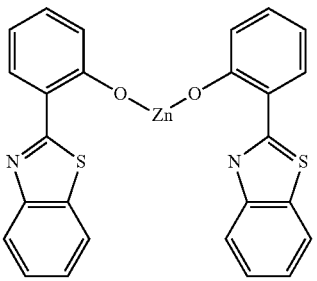

Further particularly preferred matrix materials for phosphorescent dopants are selected from compounds of the general Formula (52) (EP 1923448A1).

$$[M(L)_2]_n \quad \text{Formula (52)}$$

wherein M, L, and n are defined as in the reference. Preferably M is Zn, and L is quinolinate, and n is 2, 3 or 4. Very particularly preferred are $[Znq_2]_2$, $[Znq_2]_3$, and $[Znq_2]_4$.

Preference is given to co-hosts selected from metal oxinoid complexes whereby lithium quinolate (Liq) or $Alq_3$ are particularly preferred.

In a preferred embodiment the said QD-LEDs and/or QD-OLEDs include at least one small molecule organic fluorescent emitter. Thus, the present invention also relates to said cells and/or cell treatment device including QD-LEC and/or QD-OLEDs, characterized in that the at least one small molecule organic functional material is selected from fluorescent emitters.

In principle any fluorescent emitter known to one skilled in the art can be used for the purpose of the present invention. In general, emitter compounds tend to have an extended conjugated π-electron systems.

Many examples have been published, e.g. styrylamine derivatives as disclosed in JP 2913116B and WO 2001/021729 A1, and indenofluorene derivatives as disclosed in WO 2008/006449 and WO 2007/140847.

Blue fluorescent emitters are preferably polyaromatic compounds, such as, for example, 9,10-di(2-naphthylanthracene) and other anthracene derivatives, derivatives of tetracene, xanthene, perylene, such as, for example, 2,5,8,11-tetra-t-butylperylene, phenylene, for example 4,4'-(bis(9-ethyl-3-carbazovinylene)-1,1'-biphenyl, fluorene, arylpyrenes (US 2006/0222886), arylenevinylenes (U.S. Pat. No. 5,121,029, U.S. Pat. No. 5,130,603), derivatives of rubrene, coumarine, rhodamine, quinacridone, such as, for example, N,N'-dimethylquinacridone (DMQA), dicyanomethylenepyrane, such as, for example, 4 (dicyanoethylene)-6-(4-dimethylaminostyryl-2-methyl)-4H-pyrane (DCM), thiopyrans, polymethine, pyrylium and thiapyrylium salts, periflanthene, indenoperylene, bis(azinyl)imine-boron compounds (US 2007/0092753 A1), bis(azinyl)methene compounds and carbostyryl compounds.

Further preferred blue fluorescent emitters are described in C. H. Chen et al.: "Recent developments in organic electroluminescent materials" Macromol. Symp. 125, (1997), 1-48 and "Recent progress of molecular organic electroluminescent materials and devices" Mat. Sci. and Eng. R, 39 (2002), 143-222.

Preferred fluorescent dopants according to the present invention are selected from the class of the monostyrylamines, the distyrylamines, the tristyrylamines, the tetrastyrylamines, the styrylphosphines, the styryl ethers and the arylamines.

A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. The corresponding phosphines and ethers are defined analogously to the amines. For the purposes of this invention, an arylamine or an aromatic amine is taken to mean a compound which contains three substituted or unsubstituted aromatic or heteroaromatic ring systems bonded directly to the nitrogen. At least one of these aromatic or heteroaromatic ring systems is preferably a condensed ring system, preferably having at least 14 aromatic ring atoms. Preferred examples thereof are aromatic anthracene-amines, aromatic anthracene-diamines, aromatic pyrene-amines, aromatic pyrene-diamines, aromatic chrysene-amines and aromatic chrysene-diamines. An aromatic anthracene-amine is taken to mean a compound in which one diarylamino group is bonded directly to an anthracene group, preferably in the 9 position. An aromatic anthracene-diamine is taken to mean a compound in which two diarylamino groups are bonded directly to an anthracene group, preferably in the 9,10-position. Aromatic pyrene-amines, pyrene-diamines, chrysene-amines and chrysene-diamines are defined analogously thereto, where the diarylamino groups on the pyrene are preferably bonded in the 1 position or in the 1,6-position.

Further preferred fluorescent dopants are selected from indenofluorene-amines and indenofluorene-diamines, for example in accordance with WO 2006/122630, benzoindenofluorene-amines and benzoindenofluorene-diamines, for example in accordance with WO 2008/006449, and dibenzoindenofluorene-amines and dibenzoindenofluorene-diamines, for example in accordance with WO 2007/140847.

Examples of dopants from the class of the styrylamines are substituted or unsubstituted tristilbene-amines or the dopants described in WO 2006/000388, WO 2006/058737, WO 2006/000389, WO 2007/065549 and WO 2007/115610. Distyrylbenzene and distyrylbiphenyl derivatives are described in U.S. Pat. No. 5,121,029. Further styrylamines are found in US 2007/0122656 A1.

Particularly preferred styrylamine dopants and triarylamine dopants are the compounds of the Formulae (53) to (58) and as disclosed in U.S. Pat. No. 7,250,532 B2, DE 102005058557 A1, CN 1583691 A, JP 08053397 A, U.S. Pat. No. 6,251,531 B1, and US 2006/210830 A.

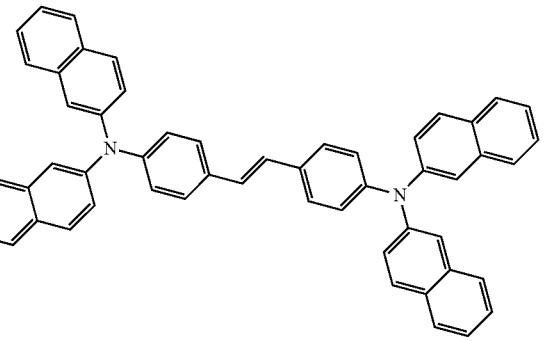

Formula (53)

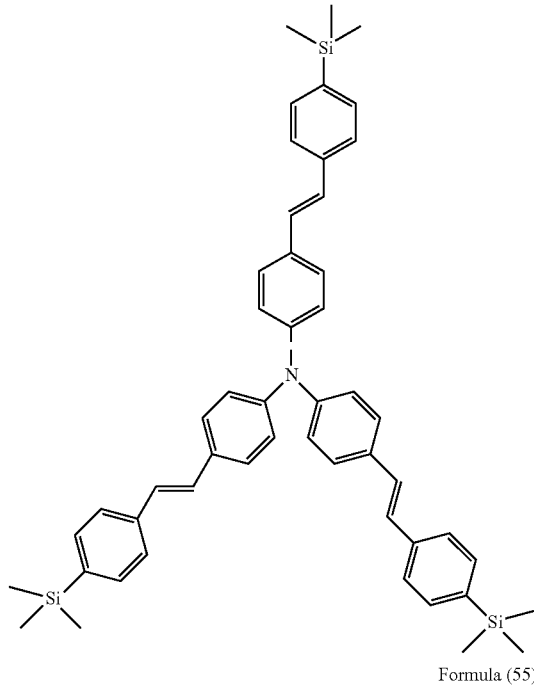

Formula (54)

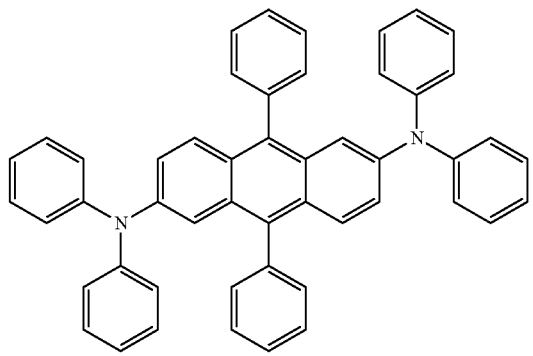

Formula (55)

Formula (56)

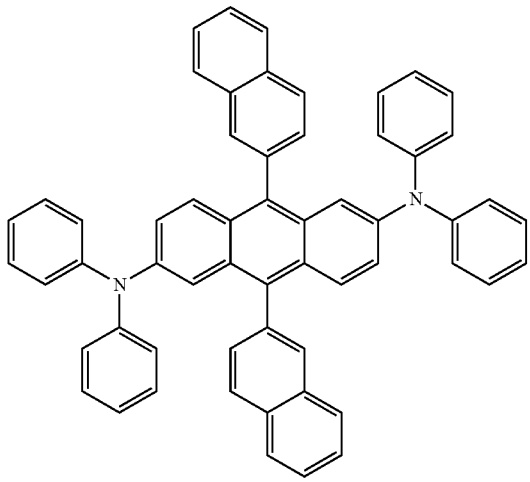

Formula (57)

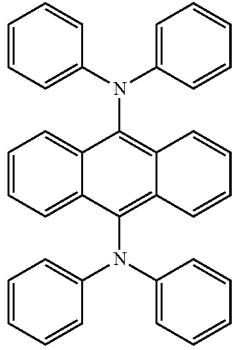

Formula (58)

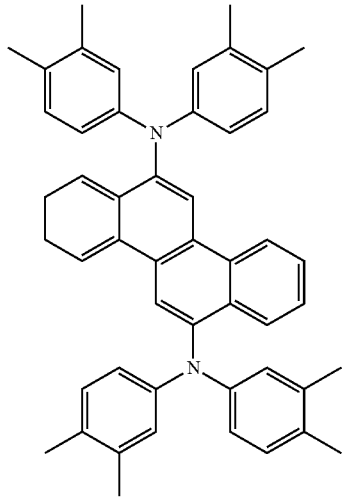

Further preferred fluorescent dopants are selected from the group of triarylamines as disclosed in EP 1957606 A1 and US 2008/0113101 A1.

Further preferred fluorescent dopants are selected from derivatives of naphthalene, anthracene, tetracene, fluorene, periflanthene, indenoperylene, phenanthrene, perylene (US 2007/0252517 A1), pyrene, chrysene, decacyclene, coronene, tetraphenylcyclopentadiene, pentaphenylcyclopentadiene, fluorene, spirofluorene, rubrene, coumarine (U.S. Pat. No. 4,769,292, U.S. Pat. No. 6,020,078, US 2007/0252517 A1), pyran, oxazone, benzoxazole, benzothiazole, benzimidazole, pyrazine, cinnamic acid esters, diketopyrrolopyrrole, acridone and quinacridone (US 2007/0252517 A1).

Of the anthracene compounds, particular preference is given to 9,10-substituted anthracenes, such as, for example, 9,10-diphenylanthracene and 9,10-bis(phenylethynyl)anthracene. 1,4-Bis(9'-ethynylanthracenyl)-benzene is also a preferred dopant.

The OLEC, QD-LEC and/or QD-OLED of embodiments include 4, preferably 3, particularly preferably 2, and very particularly preferably fluorescent emitter(s). Preference is given to QD-LECs including one EIM. OLEC, QD-LEC and/or QD-OLED according to the present invention preferably include the fluorescent emitter in a concentration of at least 0.1 wt %, particularly preferably at least 0.5 wt %, and very particularly preferably of at least 3 wt % with respect to the total amount of the emissive layer.

In a preferred embodiment the said OLEC, QD-LEC and/or QD-OLED include at least one small molecule organic phosphorescent emitter. Thus, the present invention also relates to said cells and/or cell treatment device including QD-LEC and/or QD-OLEDs, characterized in that the at least one small molecule organic functional material is selected from phosphorescent emitters.

In principle any phosphorescent emitter known to one skilled in the art can be used for the purpose of the present invention. In some embodiments, the at least one small molecule organic functional material is selected from phosphorescent emitters.

Examples of phosphorescent emitters are disclosed in the applications WO 00/70655, WO 01/41512, WO 02/02714, WO 02/15645, EP 1191613, EP 1191612, EP 1191614 and WO 2005/033244. In general, all phosphorescent complexes as used in accordance with the prior art and as are known to the person skilled in the art in the area of organic electroluminescence are suitable.

The phosphorescent emitter may be a metal complex, preferably with the formula $M(L)_z$, wherein M is a metal atom, L is in each occurrence independently of one another an organic ligand that is bonded to or coordinated with M via one, two or more positions, and z is an integer ≥1, preferably 1, 2, 3, 4, 5 or 6, and wherein, optionally, these groups are linked to a polymer via one or more, preferably one, two or three positions, preferably via the ligands L.

M is in particular a metal atom selected from transition metals, preferably selected from transition metals of group VIII, or lanthanoides, or actinides, particularly preferably selected from Rh, Os, Ir, Pt, Pd, Au, Sm, Eu, Gd, Tb, Dy, Re, Cu, Zn, W, Mo, Pd, Ag, or Ru, and very particularly preferably selected from Os, Ir, Ru, Rh, Re, Pd, or Pt. M may also be Zn.

Preferred ligands are 2 phenylpyridine derivatives, 7,8-benzoquinoline derivatives, 2 (2-thienyl)pyridine derivatives, 2 (1-naphthyl)pyridine derivatives or 2 phenylquinoline derivatives. All these compounds may be substituted, for example by fluoro- or trifluoromethyl substituents for blue. Auxiliary ligands are preferably acetylacetonate or picric acid.

In particular, complexes of Pt or Pd with tetradentate ligands of the Formula (59) as disclosed in US 2007/0087219 A1, wherein $R^1$ to $R^{14}$ and $Z^1$ to $Z^5$ are as defined in the reference, Pt porphyrin complexes having an enlarged ring system (US 2009/0061681 A1) and Ir complexes are suitable, for example 2,3,7,8,12,13,17,18-octaethyl-21H, 23H-porphyrin-Pt(II), tetraphenyl-Pt(II)-tetrabenzoporphyrin (US 2009/0061681 A1), cis-bis(2-phenylpyridinato-N, C2')Pt(II), cis-bis(2-(2'-thienyl)pyridinato-N,C3')-Pt(II), cis-bis(2-(2'-thienyl)quinolinato-N,C5')Pt(II), (2-(4,6-difluorophenyl)-pyridinato-N,C2')Pt(II) acetylacetonate, or tris (2-phenylpyridinato-N,C2')-Ir(III) (Ir(ppy)$_3$, green), bis(2-phenylpyridinato-N,C2)Ir(III) acetylacetonate (Ir(ppy)$_2$ acetylacetonate, green, US 2001/0053462 A1, Baldo, Thompson et al. Nature 403, (2000), 750-753), bis(1-phenylisoquinolinato-N,C2')(2-phenylpyridinato-N,C2')iridium (III), bis(2-phenylpyridinato-N,C2')(1-phenylisoquinolinato-N,C2')iridium(III), bis(2-(2'-benzothienyl)pyridinato-N,C3')iridium(III) acetylacetonate, bis(2-(4',6'-difluorophenyl)pyridinato-N,C2')iridium(III) piccolinate (Firpic, blue), bis(2-(4',6'-difluorophenyl)-pyridinato-N,C2') Ir(III) tetrakis(1-pyrazolyl)borate, tris(2-(biphenyl-3-yl)-4-tert-butylpyridine)iridium(III), (ppz)$_2$Ir(5phdpym) (US 2009/0061681 A1), (45ooppz)$_2$Ir(5phdpym) (US 2009/0061681 A1), derivatives of 2 phenyl-pyridine-Ir complexes, such as, for example, iridium(III)bis(2-phenyl-quinolyl-N,C2')acetylacetonate (PQIr), tris(2-phenylisoquinolinato-N,C)Ir(III) (red), bis(2-(2'-benzo[4,5-a]thienyl)pyridinato-N,C3)Ir acetylacetonate ([Btp$_2$Ir (acac)]⁻, red, Adachi et al. Appl. Phys. Lett. 78 (2001), 1622-1624).

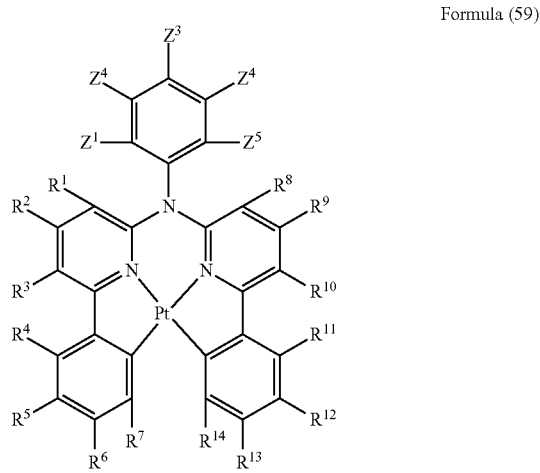

Formula (59)

Also suitable are complexes of trivalent lanthanides, such as, for example, Tb$^{3+}$ and Eu$^{3+}$ (J. Kido et al. Appl. Phys. Lett. 65 (1994), 2124, Kido et al. Chem. Lett. 657, 1990, US 2007/0252517 A1), or phosphorescent complexes of Pt(II), Ir(I), Rh(I) with maleonitrile dithiolate (Johnson et al., JACS 105, 1983, 1795), Re(I) tricarbonyl diimine complexes (Wrighton, JACS 96, 1974, 998 inter alia), Os(II) complexes with cyano ligands and bipyridyl or phenanthroline ligands (Ma et al., Synth. Metals 94, 1998, 245) or Alq$_3$.

Further phosphorescent emitters with tridentate ligands are described in U.S. Pat. No. 6,824,895 and U.S. Pat. No. 7,029,766. Red-emitting phosphorescent complexes are mentioned in U.S. Pat. No. 6,835,469 and U.S. Pat. No. 6,830,828.

A particularly preferred phosphorescent dopant is a compound with the Formula (60) and further compounds as disclosed, e.g., in US 2001/0053462 A1.

A particularly preferred phosphorescent dopant is a compound with the Formula (61) and further compounds as disclosed, e.g., in WO 2007/095118 A1.

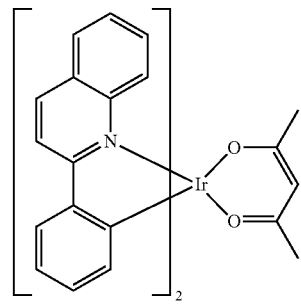

Formula (60)

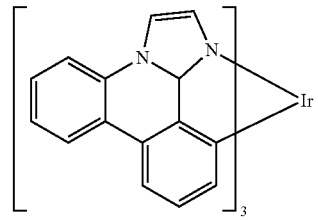

Formula (61)

Further derivatives are described in U.S. Pat. No. 7,378,162 B2, U.S. Pat. No. 6,835,469 B2, and JP 2003/253145 A.

Particular preference is given to organic electroluminescent compounds selected from organo metallic complexes.

The term electroluminescent compound refers to a material which, upon receiving energy by applying a voltage, undergoes radiative decay to emit light.

Further to metal complexes mentioned elsewhere herein, a suitable metal complex according to the present invention can be selected from transition metals, rare earth elements, lanthanides and actinides is also subject of this invention. Preferably the metal is selected from Ir, Ru, Os, Eu, Au, Pt, Cu, Zn, Mo, W, Rh, Pd, or Ag.

In a preferred embodiment, the small organic functional material emits in ultraviolet (UV) range. Suitable UV emitter materials can be selected from organic compounds including a wide-gap between the highest occupied molecular orbital (HOMO) and the lowest unoccupied molecular orbital (LUMO) moieties with a small π-conjugated system. Such UV emitter can be preferably selected from small molecular compounds including carbazoles, indenocarbazole, indolocarbazole, silane, fluorene, triazine, thiophene, dibenzothiophene, furane, dibenzofurane, imidazole, benzimidazole, anthracene, naphthalene, phenanthrene, amine, triarylamine and derivatives thereof.

The OLEC, QD-LEC and/or QD-OLED according to the present invention include 4, preferably 3, particularly preferably 2, and very particularly preferably fluorescent emitter(s). Preference is given to QD-LECs including one EIM.

The OLEC, QD-LEC and/or QD-OLED according to the present invention preferably include the fluorescent emitter in a concentration of at least 1 wt %, particularly preferably at least 5 wt %, and very particularly preferably of at least 10 wt % with respect to the total amount of the emissive layer.

In one embodiment, the QD-LEC of the cells and/or cell treatment device according to the present invention includes
(1) a first electrode;
(2) a second electrode;
(3) an emissive layer (EML) including the at least one quantum dot, at least one ionic compound and the at least one small organic functional material positioned between the first and second electrode.

As outlined elsewhere within the present application, embodiments of the cells and/or cell tissue treatment device including OLEC (also called herein LEC), QD-LEC and/or QD-OLED are particularly suited for the application in phototherapy and PDT. They are rather simple in terms of structure and manufacturing, which reduces production costs. More advantages of OLECs, particularly QD-LEC(s) have already been discussed within the present invention. The OLECs or QD-LECs preferably include at least two electrodes, particularly preferably two electrodes, a cathode and an anode. Both electrodes are connected through the EML.

Preferred materials for the electrodes used in OLEC, QD-LEC and/or QD-OLED are selected from metals, particularly preferably selected from Al, Cu, Au, Ag, Mg, Fe, Co, Ni, Mn, Zn, Cr, V, Pd, Pt Ga, In and their alloys, conductive oxide, for example ITO, AZO, ZnO, and conductive organic thin films including such as poly(ethylenedioxythiophene)-polystyrene sulfonate (PEDOT:PSSH), Polyaniline (PANI). Further suitable conducting polymers could be found for example in the reviews edited by Michael S. Freund & Bhavana Deore, in "Self-Doped Conducting Polymers", John Willey & Sons, Ltd., 2007.

Preferably, the OLECs, QD-LECs and/or QD-OLEDs are prepared on a flexible substrate. The suitable substrate is preferably selected from films or foils based on polymers or plastics. The main selection criteria for polymers or plastics are 1) hygienic property and 2) glass transition temperature. The glass temperature ($T_g$) of the polymers can be found in a common handbooks, e.g. in "Polymer Handbook", Eds. J. Brandrup, E. H. Immergut, and E. A. Grulke, John Willey & Sons, Inc., 1999, VI/193-VI/276. Preferably, the $T_g$ of the polymer is above 100° C., particularly preferably above 150° C., and very particularly preferably above 180° C. Very preferred substrates are for example, poly(ethylene terephthalate) (PET) and poly(ethylene 2,6-naphthalate) (PEN).

To avoid degradations caused by oxygen and moisture, and also to prevent active materials in the devices, for example the ionic compounds and the organic electroluminescent compounds from being in contact with the subject to be treated, an appropriate encapsulation for the said device is a prerequisite for the applications in therapeutic treatments and cosmetic conditions.

There are many technologies suitable for encapsulation of the devices according to the present invent. In general, all encapsulation techniques, which are developed for organic light emitting diodes (OLEDs), organic solar cells, organic dye-sensitized solar cells, organic field-effect transistor (OFETs), thin film batteries, microelectromechanical systems (MEMS) and electronic papers, can be applied in order to encapsulate the devices according to the present invention.

In a preferred embodiment, the device of the present invention is encapsulated using a thin film encapsulation. Typically, a thin film encapsulation consists of a multi alternating layers of an inorganic/organic stack, wherein inorganic layers are used to achieve adequate barrier performance and organic layers to eliminate inevitable defects of the inorganic layers. The materials used for inorganic layers can be selected from metals, metal oxides or mixed oxides, for example Ag, $SiO_x$, $SiN_x$, $AlO_x$, $ZrO_x$, $ZnO_x$, $HfO_x$, $TiO_x$ and indium tin oxide and so on. Some examples are alternating multilayers of vacuum-deposited acrylate polymers/$AlO_x$ as reported by Graff, G. L. et al. (J. Appl. Phys. 2004, 96, 1840), $Al_2O_3$/polyurea layers as reported by Young Gu Lee et al. (Org. Electron. 2009, 10, 1352 and in Dig. Tech. Pap.-Soc. Inf. Disp. Int. Symp. 2008, 39, 2011), $SiON/SiO_2$/parylene on PET substrate as reported by Han, Jin Woo, et al. (Jpn. J. Appl. Phys., Part 1 2006, 45, 9203), and polyacrylate (20 μm)-Ag (200 nm) as reported by Wang, Li Duo et al. (Chin. Phys. Lett. 2005, 22, 2684).

By using advanced deposition techniques, for example atomic layer deposition (ALD), plasma assisted pulsed laser deposition (PAPLD) and plasma enhanced chemical vapor deposition (PECVD), the defects in inorganic layer can be significantly reduced so that all inorganic layers can be used, for example $Al_2O_3/HfO_2$ nanolaminated films by ALD as reported by Chang, Chih Yu et al. (Org. Electron. 2009, 10, 1300), and $SiN_x/SiO_x$ layers as reported by Li, C. Y. et al. (IEEE Electron. Compon. Technol. Conf. 2008, 58$^{th}$, 1819), (PECVD SiO)/poly-benzo-oxazole (PBO) by Shimooka, Y. et al. (IEEE Electron. Compon. Technol. Conf. 2008, 58$^{th}$, 824), nanolaminated alternating layers of $Al_2O_3/ZrO_2$ by Meyer, J. et al. (Appl. Phys. Lett. 2009, 94, 233305/1), and nanolaminates of $Al_2O_3/ZrO_2$ by PAPLD as reported by Gorrn, Patrick et al. (J. Phys. Chem. 2009, 113, 11126), and SiC layers by PECVD as reported by Weidner, W. K. et al. (Annu. Tech. Conf. Proc—Soc. Vac. Coaters 2005, 48$^{th}$, 158), multilayer stack of silicon nitride-silicon oxide-silicon nitride silicon oxide-silicon nitride (NONON) by PECVD as reported by Lifka, H., et al. (Dig. Tech. Pap.-Soc. Inf. Disp. Int. Symp. 2004, 35, 1384), and polyethersulfon (PES)/ALD $AlO_x$ as reported by Park, Sang-Hee Ko, et al. (ETRI Journal 2005, 545). A review on thin film encapsulation by CVD and ALD is provided by Stoldt, Conrad R, et al. (J. Phys. D: Appl. Phys. 2006, 39, 163).

Further single layer encapsulation was also developed. Examples of single barrier layers are a perfluorinated polymer (Cytop), which can be easily spin-coated on OLEDs, as reported by Granstrom, J. et al. (Appl. Phys. Lett. 2008, 93, 193304/1), and single layer consisting of aluminum oxynitride ($AlO_xN_y$) by using a reactive radio frequency (RF) magnetron sputtering as reported by Huang, L. T. et al. (Thin Solif Films 2009, 517, 4207), single poly-SiGe layer by PECVD as reported by Rusu, Cristina et al. (J. Microelectromech. Syst. 2003, 12, 816).

Further details on materials and methods for encapsulation are disclosed, e.g., in WO 2009/089417, WO 2009/089417, WO 2009/042154, WO 2009/042052, US 2009/081356, US 2009/079328, WO 2008/140313, WO 2008/012460, EP 1868256, KR 2006/084743, KR 2005/023685, US 2005/179379, US 2005/023974, KR 2003/089749, US 2004/170927, US 2004/024105, WO 2003/070625, and WO 2001/082390.

In another preferred embodiment, the device of the present invention is encapsulated by using a curable resin together with a cap, wherein the cap covers at least the light emitting area, and the curable resin is applied between the substrate and the cap. The cap materials can be selected from metals and plastics in form of a plate or foil, and glass cap. Preferably, the cap is flexible, which is preferably selected from metal foils, plastic foils or metallised plastic foils. The metal can be selected from Al, Cu, Fe, Ag, Au Ni, whereby Al is particularly preferred. The selection criteria for plastics are 1) hygienic aspects 2) the glass transition temperature ($T_g$), which is supposed to be high enough. $T_g$ of polymers can be found in a suitable handbook, for example in "Polymer Handbook", Eds. J. Brandrup, E. H. Immergut, and E. A. Grulke, John Willey & Sons, Inc., 1999, VI/193-VI/276. Preferably, the polymer suitable for cap material has a $T_g$ above 60° C., preferably above 70° C., particularly preferably above 100° C., and very particularly preferably above 120° C. The cap used in the present invention is poly(ethylene 2,6-naphthalate) (PEN).

The suitable resin can be thermally cured or UV-curable. Preferably, the resin is UV-curable, optionally supported or facilitated by heating. A typical resin is the epoxy-based resin, which is commercially available at for example Nagase & Co., LTD. and DELO Industrie Klebstoffe. The resin can be applied on full-area of the emitting area or just on the edge, where no light emitting area is underneath.

OLECS and QD-LECs are characterized in that charge transport occurs via transport of charged species, rather than pure transport of electrons and holes as observed in OLEDs. Thus, OLECs and QD-LECs typically include ionic species.

Typical ionic species, also called ionic materials, which are suitable for the OLECS and/or QD-LECs according to the present invention, have the general formula $K^+A^-$, wherein $K^+$ and $A^-$ represent a cation and an anion, respectively.

Preferably the ionic materials are soluble in the same solvent as the organic emissive material. This easily allows the preparation of a mixture including the said emitter material(s) and the ionic material(s). Typically organic emissive materials are soluble in common organic solvents, such as toluene, anisole, chloroform.

Preferably, the said ionic material is solid at room temperature and particularly preferably, the said ionic material is solid at room temperature and getting softer between 30 to 37° C.

The cation can be organic or inorganic. Suitable inorganic cations $K^+$ can be selected from, for example, $K^+$ (potassium) and $Na^+$. Suitable organic cations $K^+$ can be selected from ammonium-, phosphonium, thiouronium-, guanidinium cations as shown in Formulae (62) to (66) or heterocyclic cations as shown in Formulae (67) to (94).

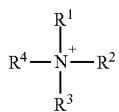

Formula (62)

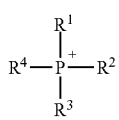

Formula (63)

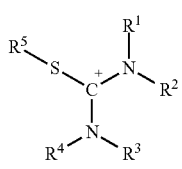

Formula (64)

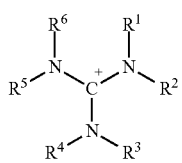

Formula (65)

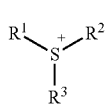

Formula (66)

wherein $R^1$ to $R^6$ can be, independently from each other, selected from linear or hyperbranched alkyl rests with 1 to 20 C-atoms, linear or hyperbranched alkenyl rests with 2 to 20 C-atoms and one or more non-conjugated double bonds, linear or hyperbranched alkinyl rests with 2 to 20 C-atoms and one or more non-conjugated triple bond, saturated, partly saturated or completely saturated cycloalkyl with 3 to 7 C-atoms, which can further be substituted with alkyl groups having 1 to 6 C-atoms, wherein one or more substituents R may be partly or completely substituted with halogen, particularly with —F and/or —Cl, or partly substituted with —OR', —CN, —C(O)OH, —C(O)$NR_{12}$, —$SO_2NR_{12}$, —$SO_2OH$, —$SO_2X$, —$NO_2$, wherein one or two non adjacent and non α-carbon atoms of $R^1$ to $R^6$ can be substituted with groups selected from —O—, —S—, —S(O)—, —$SO_2$—, —$N^+R'_2$—, —C(O)NR'—, —$SO_2NR'$—, and —P(O)R'—, wherein R'=H, unsubstituted, partly or completely with —F substituted C1 to C6-alkyl, C3 to C7-cycloalkyl, unsubstituted or substituted phenyl and X=halogen.

In Formula (62) $R^1$ to $R^4$ can be H, with the provisio that at least one of the rests $R^1$ to $R^4$ is not H. In Formula (63) $R^1$ to $R^4$ can be H and $NR'_2$, wherein $R^1$ is defined as above. In Formula (64) $R^1$ to $R^5$ can be H. In Formula (65) $R^1$ to $R^6$ can be H, CN, and $NR'_2$, wherein R' is defined as above.

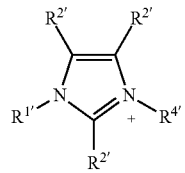

Formula (67)

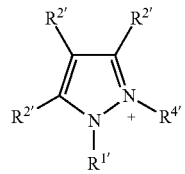

Formula (68)

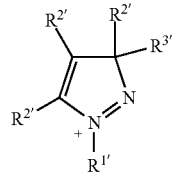

Formula (69)

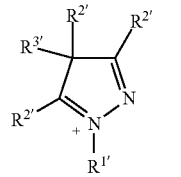

Formula (70)

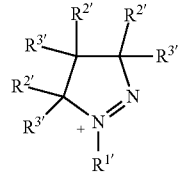

Formula (71)

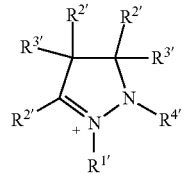

Formula (72)

-continued
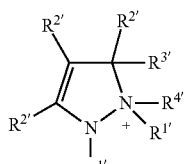
Formula (73)
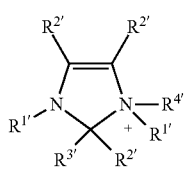
Formula (74)
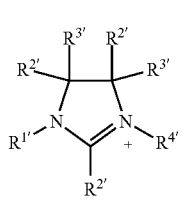
Formula (75)
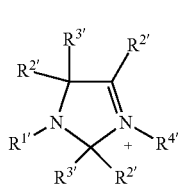
Formula (76)
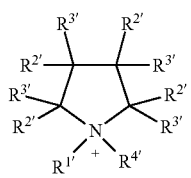
Formula (77)
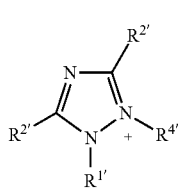
Formula (78)
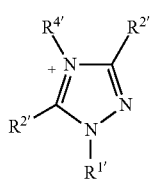
Formula (79)
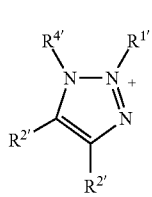
Formula (80)
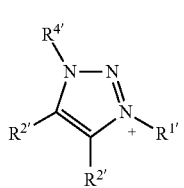
Formula (81)
-continued
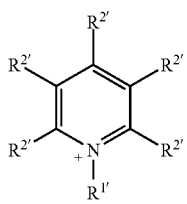
Formula (82)
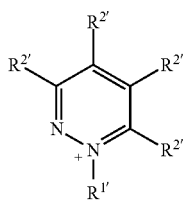
Formula (83)
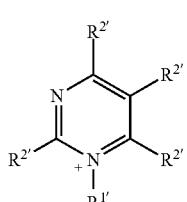
Formula (84)
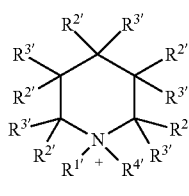
Formula (85)
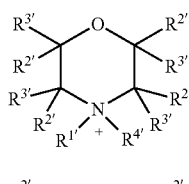
Formula (86)
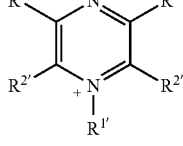
Formula (87)
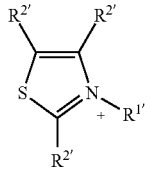
Formula (88)
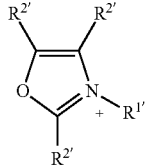
Formula (89)

-continued

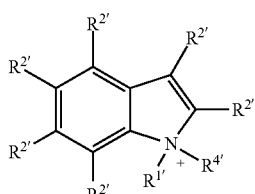

Formula (90)

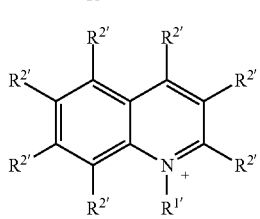

Formula (91)

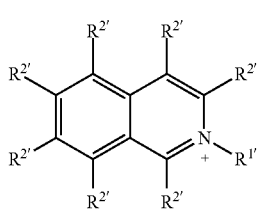

Formula (92)

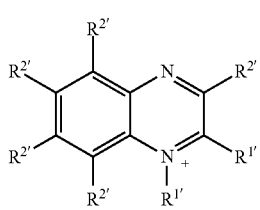

Formula (93)

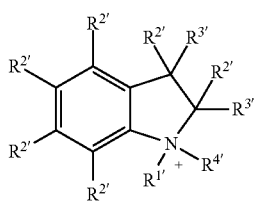

Formula (94)

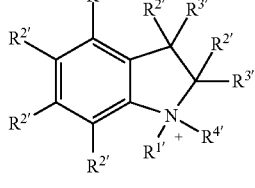

Wherein the substituents $R^{1'}$ to $R^{4'}$ are independently from each other selected from H, CN, linear and branched alkyl rest with 1 to 20 C-atoms, linear or branched alkenyl rest with 2 to 20 C-atoms and one or more non conjugated double bonds, linear or branched alkinyl rest with 2 to 20 C-atoms and one or more non conjugated triple bonds, partly or completely non saturated cycloalkyl rest with 3 to 7 C-atoms which can be substituted with alkyl rests with 1 to 6 C-atoms, saturated and partly or completely non saturated heteroaryls, heteroaryl-$C_1$-$C_6$-alkyl, or alkyl-$C_1$-$C_6$-alkyl, wherein the substituents $R^{1'}$, $R^{2'}$, $R^{3'}$ and/or $R^{4'}$ together can form a ring, wherein one or more of the substituents $R^{1'}$ to $R^{4'}$ can partly or completely be substituted with halogen, particularly with —F and/or —Cl, and —OR', —CN, —C(O)OH, —C(O)$NR'_2$, —$SO_2NR'_2$, —C(O)X, —$SO_2OH$, —$SO_2X$, —$NO_2$, wherein the substituents $R^{1'}$ and/or $R^{4'}$ are not substituted with halogen at the same time, wherein one or two carbon atoms of the substituents $R^{1'}$ and $R^{2'}$, which are non adjacent or bound to an heteroatom, can be substituted by a group selected from —O—, —S—, —S(O)—, —$SO_2$—, —$N^+R'_2$—, —C(O)NR'—, —$SO_2NR'$—, and —P(O)R'— wherein R'=H, unsubstituted, partly or completely with —F substituted alkyl with 1 to 6 C-atoms, cycloalkyl with 3 to 7 C-atoms, unsubstituted or substituted phenyl and X=halogen.

Preference is given to $R^{2'}$ selected from —OR', —$NR'_2$, —C(O)OH, —C(O)$NR'_2$, —$SO_2NR'_2$)—$SO_2OH$, —$SO_2X$, and —$NO_2$.

Further preferred ionic materials are disclosed in, e.g., US 2007/0262694 A1.

Further particularly preferred ionic materials include a cation having a structure represented by Formula (95). They include N,N,N-trimethylbutyl ammonium ion, N-ethyl-N,N-dimethyl-propyl ammonium ion, N-ethyl-N,N-dimethylbutyl ammonium ion, N,N,-dimethyl-N-propylbutyl ammonium ion, N-(2-methoxyethyl)-N,N-dimethylethyl ammoniumion, 1-ethyl-3-methyl imidazolium ion, 1-ethyl-2,3-dimethyl imidazolium ion, 1-ethyl-3,4-dimethyl imidazolium ion, 1-ethyl-2,3,4-trimethyl imidazolium ion, 1-ethyl-2,3,5-trimethyl imidazolium ion, N-methyl-N-propyl pyrrolidinium ion, N-butyl-N-methylpyrrolidinium ion, N-sec-butyl-N-methylpyrrolidinium ion, N-(2-methoxyethyl)-N-methylpyrrolidinium ion, N-(2-ethoxyethyl)-N-methylpyrrolidinium ion, N-methyl-N-propyl piperidinium ion, N-butyl-N-methyl piperidinium ion, N-sec-butyl-N-methylpiperidinium ion, N-(2-methoxyethyl)-N-methyl piperidiniumion and N-(2-ethoxyethyl)-N-methyl piperidinium ion.

Formula (95)

$$-\underset{|}{\overset{|}{N^+}}-$$

Very particularly preferred is N-methyl-N-propyl piperidinium.

Particularly preferred ionic material is a compound selected from the group of ionic compounds, which are soluble in common organic solvents such as toluene, anisole, and chloroform, consisting of methyltrioctylammonium trifluoromethane-sulfonate (MATS), 1-methyl-3-octylimidazolium octylsulfate, 1-butyl-2,3-dimethylimidazolium octylsulfate, 1-octadecyl-3-methylimidazolium bis(trifluoromethylsulfonyl)imide, 1-octadecyl-3-methylimidazolium tris(pentafluoroethyl)trifluorophosphate, 1,1-dipropylpyrrolidimium bis(trifluoromethylsulfonyl)imide, trihexyl(tetradecyl)phosphonium bis(1,2-benzenediolato(2-)-O,O')borate, and N,N,N',N',N',N'-pentamethyl-N'-propyl-guanidinium trifluoromethanesulfonate.

Further preferred cations are selected from compounds of one of the general Formulae (96) to (101)

Formula (96)

$$R^4-\underset{\underset{R^3}{|}}{\overset{\overset{R^1}{|}}{N^+}}-R^2$$

Formula (97)

$$R^1-\underset{\underset{R^3}{}}{\overset{\overset{R^2}{|}}{S^+}}R^3$$

Formula (98)

$$R^4-\underset{\underset{R^3}{|}}{\overset{\overset{R^1}{|}}{P^+}}-R^2$$

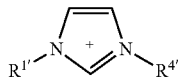

Formula (99)

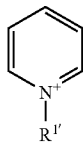

Formula (100)

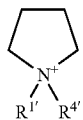

Formula (101)

Wherein $R^1$ to $R^4$ are defined as in Formulae (62), (63), and (67), and $R^{1'}$ and $R^{4'}$ as in Formulae (68), (82), and (77).

Further preferred ionic materials suitable for the OLECs and/or QD-LECs of embodiments is a compound wherein one of $K^+$ or $A^-$ is covalently bounded to a polymer backbone.

Further preferred ionic materials suitable for the OLECs and/or QD-LECs of embodiments are selected from compounds wherein one of $K^+$ or $A^-$ is an organic emissive material, which can be selected from small molecule and polymeric emissive materials as described elsewhere within the present invention.

Suitable anions $A^-$ can be selected from $[HSO_4]^-$, $[SO_4]^{2-}$, $[NO_3]^-$, $[BF_4]^-$, $[(R_F)BF3]^-$, $[(R_F)_2BF_2]^-$, $[(R_F)_3BF]^-$, $[(R_F)_4B]^-$, $[B(CN)_4]^-$, $[PO_4]^{3-}$, $[HPO_4]^{2-}$, $[H_2PO_4]^-$, $[Alkyl\text{-}OPO_3]^{2-}$, $[(Alkyl\text{-}O)_2PO_2]^-$, $[Alkyl\text{-}PO_3]^{2-}$, $[R_FPO_3]^{2-}$, $[(Alkyl)_2PO_2]^-$, $[(R_F)_2PO_2]^-$, $[RFSO_3]^-$, $[HOSO_2(CF_2)_nSO_2O]^-$, $[OSO_2(CF_2)_nSO_2O]^{2-}$, $[Alkyl\text{-}SO_3]^-$, $[HOSO_2(CH_2)_nSO_2O]^-$, $[OSO_2(CH_2)_nSO_2O]^{2-}$, $[Alkyl\text{-}OSO_3]^-$, $[Alkyl\text{-}C(O)O]^-$, $[HO(O)C(CH_2)_nC(O)O]^-$, $[R_FC(O)O]^-$, $[HO(O)C(CF_2)_nC(O)O]^-$, $[O(O)C(CF_2)_nC(O)O]^{2-}$, $[(R_FSO_2)_2N]^-$, $[(FSO_2)_2N]^-$, $[((R_F)_2P(O))_2N]^-$, $[(RFSO_2)_3C]^-$, $[(FSO_2)_3C]^-$, $Cl^-$ and/or $Br^-$
wherein:
n=1 to 8;
$R_F$ is fluorinated alkyl of formula $(C_mF_{2m-x+1}H_x)$ with m=1 to 12 and x=0 to 7, wherein for m=1 and x=0 to 2, and/or fluorinated (also perfluorinated) aryl or alkyl-aryl.

The alkyl-group mentioned above can be selected from linear or hyperbranched alkyl groups with 1 to 20 C-atoms, preferably with 1 to 14 C-atoms and particularly preferably with 1 to 4 C-atoms. Preferably $R_F$ means $CF_3$, $C_2F_5$, $C_3F_7$ or $C_4F_9$.

Preferred anions are selected from $PF_6^-$, $[PF_3(C_2F_5)_3]^-$, $[PF_3(CF_3)_3]^-$, $BF_4^-$, $[BF_2(CF_3)_2]^-$, $[BF_2(C_2F5)_2]^-$, $[BF_3(CF_3)]^-$, $[BF_3(C_2F_5)]^-$, $[B(COOCOO)_2]^-(BOB^-)$, $CF_3SO_3^-$ (Tf), $C_4F_9SO_3^-$ (Nf), $[(CF_3SO_2)_2N]^-(TFSI^-)$, $[(C_2F_5SO_2)_2N]^-$ (BETI$^-$), $[(CF_3SO_2)(C_4F_9SO_2)N]^-$, $[(CN)_2N]^-(DCA^-)$, $[CF_3SO_2]_3C]^-$, and $[(CN)_3C]^-$.

Further preferred ionic materials suitable for the OLECs and/or QD-LECs according to the present invention selected from compounds with the formula $(K^{n+})_a(A^{m-})_b$, wherein n, m, a, and b are integers from 1 to 3, and $n \times a - m \times b = 0$ and wherein one of $K^{n+}$ or $A^{m-}$ is an organic emissive material, which can be selected from compound including groups of small molecule or polymeric emitters as outlined elsewhere within the present invention. Preferably, n. m a, b are 1.

In a preferred embodiment, in the said compound in form of $(K^{n+})_a(A^{m-})_b$, one of $K^{n+}$ or $A^{m-}$ is an emissive metal complex, and particularly preferably $K^{n+}$ is an emissive metal complex, wherein the metal can be selected from transition metals, preferably those of group VIII elements, lanthanides, and actinides, particularly preferably selected from Rh, Os, Ir, Pt, Au, Sm, Eu, Gd, Tb, Dy, Re, Cu, W, Mo, Pd, Ag, Ru, and very particularly preferably selected from Ru, Os, Ir, Re. Some non-limiting examples for $K^{n+}$ are $[Ir(ppy)_2(bpy)]^+$, $[Ir(PPy)_2(dPP)]^-$, $[Ir(ppy)_2(phen)]^+$, $[Ru(bpy)_3]^{2+}$, $[Os(bpy)_2L)]^{2+}$ (L=cis-1,2-bis(diphenylphosphino)ethylene).

In a further embodiment of the present invention the said OLECs and/or QD-LECs include a compound with the formula $(K^{n+})_a(A^{m-})_b$, wherein one of $K^{n+}$ or $A^{m-}$ is an emissive singlet emitter, and particularly preferably $K^{n+}$ an emissive singlet emitter. Such kind of compound can be selected from charged laser dyes, for examples p-quaterphenyl-4,4'''-disulfonicacid disodiumsalt (polyphenyl 1), p-quaterphenyl-4,4'''-disulfonicacid dipotassiumsalt (polyphenyl 2), 2-(4-biphenylyl)-6-phenylbenzoxazo-tetrasulfonicacid potassium salt (furan 2), [1,1'-biphenyl]-4-sulfonic acid, 4',4'''-1,2-ethene-diylbis-, dipotassium salt (stilbene 1), 2,2'-([1,1'-biphenyl]-4,4'-diyldi-2,1-ethenediyl)-bis-benzenesulfonic acid disodium salt (stilbene 3), benzofuran, 2,2'-[1,1'-biphenyl]-4,4'-diyl-bis-tetrasulfonic acid (tetrasodium salt) (furan 1), 2-(p-dimethylaminostyryl)-pyridylmethyl Iodide (DASPI), 2-(p-dimethylaminostyryl)-benzothiazolylethyl Iodide (DASBTI), 3,3'-diethyloxacarbocyanine Iodide (DOCI), 4,4-difluoro-1,3,5,7,8-pentamethyl-4-bora-3a,4a-diaza-s-indacene 1,3,5,7,8-pentamethylpyrromethenedifluoroborate complex (pyrromethene 546), 3,3'-dimethyl-9-ethyl-thiacarbocyanine Iodide (DMETCI), disodium-1,3,5,7,8-pentamethylpyrro-methene-2,6-disulfonate-difluoroborate complex (pyrromethene 556), 4,4-difluoro-2,6-diethyl-1,3,5,7,8-pentamethyl-4-bora-3a,4a-diaza-s-indacene 2,6-diethyl-1,3,5,7,8-pentamethylpyrromethenedifluoroborate complex (pyrromethene 567), o-(6-amino-3-imino-3H-xanthen-9-yl)-benzoic acid (rhodamine 110), benzoic acid, 2-[6-(ethylamino)-3-(ethylimino)-2,7-dimethyl-3H-xanthen-9-yl], perchlorate (rhodamine 19), 4,4-difluoro-2,6-di-n-butyl-1,3,5,7,8-pentamethyl-4-bora-3a,4a-diaza-s-indacene 2,6-di-n-butyl-1,3,5,7,8-pentamethylpyrromethenedifluoroborate complex (pyrromethene 580), benzoic acid, and 2-[6-(ethylamino)-3-(ethylimino)-2,7-dimethyl-3H-xanthen-9-yl]-ethyl ester, monohydrochloride (rhodamine 6G), which are commercially available at Lambda Physik AG, Goettingen, Germany.

Another subject of the present invention is said QD-LEC including at least one compound of the formula $(K^{n+})_a(A^{m-})_b$, characterized in that one of $K^{n+}$ or $A^{m-}$ is an emissive singlet emitter.

Very preferably $K^{n+}$ is an emissive singlet emitter. $K^{n+}$ is preferably selected from the group as defined above.

Preferably the light emitting device is a electroluminescent device. Preference is given to said QD-LEC including 3, particularly preferably 2, and very particularly preferably 1 compound of said formula $(K^{n+})_a(A^{m-})_b$.

Actually, if the ionic species is itself a light emitting material it is considered as organic functional material as defined herein. In this case no further small functional material may be needed for said OLECs and/or QD-LECs.

In principle any quantum dot (QD) known to one skilled in the art can be employed in QD-LECs and/or QD-OLEDs according to the present invention.

Preference is given to quantum dots having emission intensity maxima in the range between 300 and 2000 nm, preferably between 350 and 1500 nm. Emission wavelengths can easily be adjusted by choosing the suitable organic semiconductor and/or by choosing the suitable quantum dot and/or by the size of a quantum dot, which in turn can precisely be tailored by synthesis. Intensities of emission can also be adapted by the concentration of a specifically sized quantum dot used in the said QD-LEC and/or QD-OLED.

Preferably the QD-LEC and/or QD-OLED according to the present invention includes quantum dots selected from Group II-VI, Group III-V, Group IV-VI and Group IV semiconductors, preferably ZnO, ZnS, ZnSe, ZnTe, CdS, CdSe, CdTe, HgS, HgSe, HgTe, MgS, MgSe, GeS, GeSe, GeTe, SnS, SnSe, SnTe, PbO, PbS, PbSe, PbTe, GaN, GaP, GaAs, GaSb, in N, in P, in As, in Sb, AlN, AlP, AlAs, AlSb, GaN, GaP, GaAs, GaSb, and a combination thereof.

Suitable semiconducting materials, which can be incorporated into quantum dots, are selected from elements of Group II-VI, such as CdSe, CdS, CdTe, ZnSe, ZnO, ZnS, ZnTe, HgS, HgSe, HgTe and alloys thereof such as CdZnSe; Group III-V, such as InAs, InP, GaAs, GaP, InN, GaN, InSb, GaSb, AlP, AlAs, AlSb and alloys such as InAsP, CdSeTe, ZnCdSe, InGaAs; Group IV-VI, such as PbSe, PbTe and PbS and alloys thereof; Group III-VI, such as InSe, InTe, InS, GaSe and alloys such as InGaSe, InSeS; Group IV semiconductors, such as Si and Ge alloys thereof, and combinations thereof in composite structures.

Further suitable semiconductor materials include those disclosed in U.S. patent application Ser. No. 10/796,832 and include any type of semiconductor, including group II-VI, group III-V, group IV-VI and group IV semiconductors. Suitable semiconductor materials include, but are not limited to, Si, Ge, Sn, Se, Te, B, C (including diamond), P, BN, BP, BAs, AlN, AlP, AlAs, AlS, AlSb, BaS, BaSe, BaTe, CaS, CaSe, CaTe, GaN, GaP, GaAs, GaSb, InN, InP, InAs, InSb, AlN, AlP, AlAs, AlSb, GaN, GaP, GaAs, GaSb, ZnO, ZnS, ZnSe, ZnTe, CdS, CdSe, CdTe, HgS, HgSe, HgTe, BeS, BeSe, BeTe, MgS, MgSe, GeS, GeSe, GeTe, SnS, SnSe, SnTe, PbO, PbS, PbSe, PbTe, CuF, CuCl, CuBr, CuI, $Si_3N_4$, $Ge_3N_4$, $Al_2O_3$, $(Al, Ga, In)_2 (S, Se, Te)_3$, $Al_2CO$, and an appropriate combination of two or more such semiconductors.

Preferably the quantum dot is selected from Group II-VI, Group III-V, Group IV-VI and Group IV semiconductors, particularly preferably from ZnO, ZnS, ZnSe, ZnTe, CdS, CdSe, CdTe, HgS, HgSe, HgTe, MgS, MgSe, GeS, GeSe, GeTe, SnS, SnSe, SnTe, PbO, PbS, PbSe, PbTe, GaN, GaP, GaAs, GaSb, InN, InP, InAs, InSb, AlN, AlP, AlAs, AlSb, GaN, GaP, GaAs, GaSb, and a combination thereof.

In some embodiments, the quantum dots may include a dopant from the group consisting of: a p-type dopant or an n-type dopant. The properties and synthesis of a doped quantum dot can be referred to "n-type colloidal semiconductor nanocrystals" by Moonsub Shim & Philippe Guyot-Sionnest, Nature vol407 (2000) p 981, and "Doped Nanocrystals" by Norris et al., Science, 319 (2008), p 1776. The quantum dots of the present invention can also include II-VI or III-V semiconductors. Examples of II-VI or III-V semiconductor nanocrystals include any combination of an element from Group II, such as Zn, Cd and Hg, with any element from Group VI, such as S, Se, Te, Po, of the Periodic Table; and any combination of an element from Group III, such as B, Al, Ga, In, and Tl, with any element from Group V, such as N, P, As, Sb and Bi, of the Periodic Table.

In quantum dots, photoluminescence and electroluminescence arise from the band edge states of the nanocrystal. The radiative band-edge emission from nanocrystals competes with non-radiative decay channel originating from surface electronic states, as reported by X. Peng, et al., J. Am. Chem. Soc. Vol119:7019-7029 (1997). Thus, the presence of surface defects such as dangling bonds provides non-radiative recombination centers and lower emission efficiency. An efficient method to passivate and remove the surface trap states is to epitaxially grow an inorganic shell material on the surface of the nanocrystal, as disclosed by X. Peng, et al., J. Am. Chem. Soc. Vol 119:7019-7029 (1997). The shell material can be chosen such that the electronic levels are type I with respect to the core material (e.g., with a larger bandgap to provide a potential step localizing the electron and hole to the core). As a result, the probability of non-radiative recombination can be reduced.

Core-shell structures are obtained by adding organometallic precursors containing the shell materials to a reaction mixture containing the core nanocrystal. In this case, rather than a nucleation-event followed by growth, the cores act as the nuclei, and the shells grow from their surface. The temperature of the reaction is kept low to favour the addition of shell material monomers to the core surface, while preventing independent nucleation of nanocrystals of the shell materials. Surfactants in the reaction mixture are present to direct the controlled growth of shell material and ensure solubility. A uniform and epitaxially grown shell is obtained when there is a low lattice mismatch between the two materials. Additionally, the spherical shape acts to minimize interfacial strain energy from the large radius of curvature, thereby preventing the formation of dislocations that could degrade the optical properties of the nanocrystal system.

In a preferred embodiment, ZnS can be used as the shell material using synthetic processes well known to one skilled in the art.

In a particularly preferred embodiment, the quantum dot of the invention includes semiconducting materials selected from Group II-VI semiconductors, alloys thereof and core/shell structures made there from. In further embodiments, the Group II-VI semiconductors are CdSe, CdS, CdTe, ZnSe, ZnS, ZnTe, alloys thereof, combinations thereof and core/shell, core multi-shell layered-structures thereof.

In some embodiments, the quantum dots according to the present invention include further ligands conjugated, cooperated, associated or attached to their surface. Suitable ligands include any group known to those skilled in the art, including those disclosed in U.S. Ser. No. 10/656,910 and U.S. 60/578,236. Use of such ligands can enhance the ability of the quantum dots to incorporate into various solvents and matrix materials, including polymers. Further preferred ligands are such having a "head-body-tail" structure, as disclosed in US 2007/0034833A1, wherein further preferably the "body" has an electron or hole transport function, as disclosed in US 20050109989A1.

The term quantum dot refers to nanocrystals that are substantially mono-dispersive in size. A quantum dot has at least one region or characteristic dimension with a dimension of less than about 500 nm, and down to on the order of less than about 1 nm. The term mono-dispersive means the size distribution is within +−10% of the stated value, for example a mono-dispersive nanocrystals of 100 nm in diameter encompasses a range of sizes from 90 nm or larger to 110 nm or smaller.

Due to the finite size of the QDs, in particular core-shell QDs, they display unique optical properties compared to their bulk counterparts. The emission spectrum is defined by a single Gaussian peak, which arises from the band-edge luminescence. The emission peak location is determined by the core particle size as a direct result of quantum confinement effects. The electronic & optical properties are discussed by Al. L. Efros and M. Rosen in Annu. Rev. Mater. Sci. 2000. 30:475-521. Furthermore, the intensity of emission can be tailored according to the concentration used in the said QD-LECs, as outlined above.

The OLECs and/or QD-LECs according to the present invention include as outlined elsewhere within the present invention at least one ionic species. Preferably, the at least one ionic species is selected from an ionic transition metal complex (iTMC).

One typical iTMC material is reported for example by Rudmann et al., J. Am. Chem. Soc. 2002, 124, 4918-4921 and Rothe et al., Adv. Func. Mater. 2009, 19, 2038-2044. The concentrations of the iTMC in the emissive layer (EML) can be from 1 to 50 wt %, preferably from 5 to 30 wt %, particularly preferably from 10 to 30 wt %, and very particularly preferably from 10 to 20 wt % with respect of the emissive layer.

The said OLECs and/or QD-LECs preferably include a further ion conducting material and/or a neutral matrix material, which can have a concentration of 1 to 90 wt %, preferably 10 to 80 wt %, particularly preferably 20 to 70 wt %, and very particularly preferably 30 to 70 wt % with respect to the total amount of the layer.

In embodiments, the cells and/or cell treatment device including an QD-LEC and/or QD-OLED according to the present invention includes a QD, which is itself an ionic compound.

Suitable ionic QD is selected from QDs including at least one ionic ligand (or cap). The suitable ligand for this embodiment can be preferably selected according to the general formulae (102) and (103):

[K$^+$][A$^-$-B-D]     Formula (102)

[A$^+$][K$^-$-B-D]     Formula (103)

wherein D is an anchor group, which anchors on the QD surface, for example a thiol group; and B a simple bond or a spacer, preferably selected from alkyl, alkoxy group; and K$^{+/-}$ and A$^{-/+}$ represent cations and an anions as described above.

The quantum dot including at least one ionic ligand according to formula (102) or (103) can be synthesized by ligand exchange as reported for example by Denis Dorokhin, et al (Nanotechnology 2010, 21, 285703). The ligand can, e.g., has the following Formula (104).

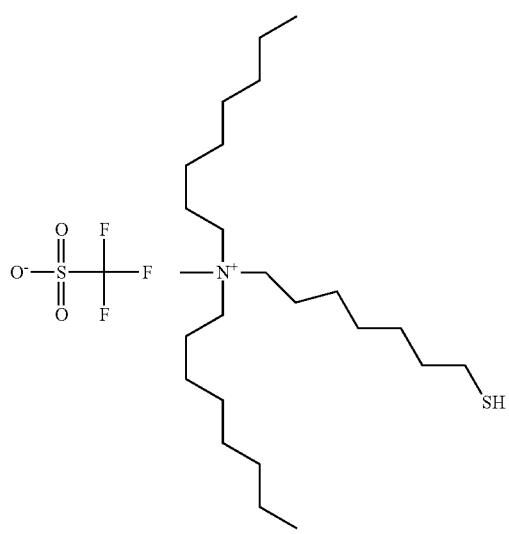

Formula (104)

Ligand exchange can be realized by mixing the toluene solution of trioctylphosphine oxide (TOPO)-coated core-shell CdSe/ZnS QDs with a toluene solution of ligand with Formula (104) under nitrogen flow and with the help of heating for example at 40° C. By controlling the reaction time, different degree of ligand exchange, between TOPO and anion in Formula (104), can be obtained. In a preferred embodiment, only partially exchange is desired, therefore, the reaction time is preferably short, for example shorter than 24 hrs.

Preference is given to QD-LECs and/or QD-OLEDs, characterized in that the emissive layer (EML) includes at least one ionic quantum dot and at least one small organic functional molecule selected from host materials, fluorescent emitters, phosphorescent emitters, hole transport materials (HTMs), hole injection materials (HIMs), electron transport materials (ETMs), and electron injection materials (EIMs). The small organic functional materials, which are electrically neutral, are the same as outlined elsewhere within the present invention.

Particular preference is given to said QD-LECs where the EML includes 2, and very particularly preferably 1 ionic quantum dot(s).

In yet another preferred embodiment the EML of the QD-LECs and/or QD-OLEDs includes one ionic quantum dot and one small organic functional material selected from host and/or phosphorescent emitters. The concentrations of the components in the EML can be for quantum dot from 1 to 20 wt %, for host from 50 to 98 wt %, and for phosphorescent emitter from 1 to 20 wt %.

In one further preferred embodiment the EML of the QD-LECs and/or QD-OLEDs includes one ionic quantum dot and one small organic functional material selected from host and/or fluorescent emitters. The concentrations of the components in the EML can be for quantum dot from 1 to 20 wt %, for host from 50 to 98 wt %, and for fluorescent emitter from 1 to 20 wt %.

The EML of the QD-LECs and/or QD-OLEDs may include further organic functional materials, which can be small molecule or polymer.

An ionic quantum dot used in embodiments may include at least one ionic ligand according to the Formulae (102) or (103).

The present invention further related to a mixture used in the OLEC, QD-LEC and/or QD-OLED of a cells and/or cell treatment device according to embodiments, which includes at least one quantum dot and/or at least one ionic compound and/or at least small organic functional material.

In a preferred embodiment including a QD-LEC and/or a QD-OLED, the said mixture includes at least one QD, at least one ionic compound, at least one host material and at least one emitter, which can be selected from phosphorescent emitter or fluorescent emitter.

In another preferred embodiment including a QD-LEC and/or a QD-OLED, the said mixture includes at least one ionic QD, at least one host material and at least one emitter, which can be selected from phosphorescent emitter or fluorescent emitter. In yet another preferred embodiment, the said mixture includes at least one QD, at least one host material and at least one ionic emitter, which can be selected from phosphorescent emitter or fluorescent emitter. Preferably, the said ionic emitter is selected from iTMCs.

In a further preferred embodiment including a QD-LEC and/or QD-OLED, the mixture includes at least ion conducting material, which can be selected from for example polyethylene oxides (PEO) for Li$^+$.

The mixture may further include other organic functional material, which can in form of small molecule or polymer or oligomer or dendrimer, and can be selected from host, emitter, HIM, HTM, ETM, EIM, and metal complexes.

In the mixture according to any embodiment, the QD may include at least one element selected from selected from Group II-VI, Group III-V, Group IV-VI and Group IV semiconductors, preferably ZnO, ZnS, ZnSe, ZnTe, CdS, CdSe, CdTe, HgS, HgSe, HgTe, MgS, MgSe, GeS, GeSe, GeTe, SnS, SnSe, SnTe, PbO, PbS, PbSe, PbTe, GaN, GaP, GaAs, GaSb, InN, InP, InAs, InSb, AlN, AlP, AlAs, AlSb, GaN, GaP, GaAs, GaSb, and an appropriate combination of two or more such semiconductors, and/or with core/shell, core multi-shell layered-structures thereof.

The mixture according to any embodiment may be characterized in that the concentration of the QD is chosen preferably from 0.5 to 30 wt %, particularly preferably from 1 to 20 wt %, and very particularly preferably from 5 to 15 wt %.

The mixture according to any embodiment may include at least further one emitter. In the mixture according to embodiments the emission spectrum of the quantum dot may overlap with the absorption of the further emitter. Thereby, a Förster energy transfer can be realized. In the mixture according to any embodiment, the further emitter can be selected from organic compounds or other quantum dots.

According to a further embodiment, the cells and/or cell tissue treatment device includes an OLEC, QD-LEC and/or QD-OLED as an electronic device including a mixture as described herein or a quantum dot as described herein. The electronic device may include at least one anode, one cathode and a functional layer in-between the anode and the cathode, wherein the functional layer includes the mixture or the quantum dot.

Another aspect of the invention relates to a formulation, preferably a solution, for use in the cells and/or cell treatment device, the formulation including a mixture or a quantum dots described herein and one or more organic solvents.

Examples of suitable and preferred organic solvents include, without limitation, dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetralin, decalin, indane and/or mixtures thereof.

The concentration of the mixture in the solution is preferably 0.1 to 10 wt %, particularly preferably 0.5 to 5 wt %. Optionally, the solution also includes one or more binders to adjust the rheological properties, as described in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., Journal of Paint Technology, 38, No 496, 296 (1966)". Solvent blends may also be used and can be identified as described in "Solvents, W. H. Ellis, Federation of Societies for Coatings Technology, 9-10, 1986". Such a procedure may lead to a blend of 'non' solvents that will dissolve the mixture, although it is desirable to have at least one true solvent in a blend.

Another preferred form of a formulation used in embodiments is an emulsion, and very preferably a mini-emulsion, which are specially formulated heterophase systems in which stable nanodroplets of one phase are dispersed in a second, continuous phase. Embodiments relate to a mini-emulsion, wherein the different components of the mixture are located either in the same phase or in the different phases. Preferred distributions are as follows:
1) majority or all of QDs and organic functional materials in nanodroplets (discontinuous phase), and majority or all of ionic compounds in the continuous phase;
2) majority or all of organic functional materials in nanodroplets (discontinuous phase), and majority or all of QD and ionic compounds in the continuous phase;

Both mini-emulsion, wherein the continuous phase is a polar phase, and inverse miniemulsion, wherein the continuous phase is a non-polar phase, could be used in the present invention. The preferred form is the mini-emulsion. To increase the kinetic stability of the emulsion, surfactant(s) could be added. The selection of solvents for two phase and surfactants, and the processing to make a stable mini-emulsion is well known to one skilled in the art, or are referred to various publications, for example, Landfester et al. (Annu. Rev. Mater. Res. 2006, 36, 231).

For use as thin layers in electronic or opto-electronic devices the mixture or a formulation of them of the present invention may be deposited by any suitable method. Liquid coating of devices such as light emitting device is more desirable than vacuum deposition techniques. Solution deposition methods are particularly preferred. Preferred deposition techniques include, without limitation, dip coating, spin coating, ink jet printing, letter-press printing, screen printing, doctor blade coating, roller printing, reverse-roller printing, offset lithography printing, flexographic printing, web printing, spray coating, brush coating or pad printing, slot-die coating. Ink-jet printing is particularly preferred as it allows high resolution displays to be prepared.

Selected solutions of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the mixture of the present invention should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents methoned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a mixture of embodiments by ink jet printing includes a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed including the solvent with the polymer, which reduces or prevents clogging of the jets and separation of the components during spraying. The solvent(s) may include those selected from the following list of examples: dodecylbenzene, 1-methyl-4-tert-butylbenzene, terpineol limonene, isodurene, terpinolene, cymene, diethylbenzene. The solvent may be a solvent mixture, that is a combination of two or more solvents, each solvent preferably having a boiling point>100° C., more preferably >140° C. Such solvent(s) also enhance film formation in the layer deposited and reduce defects in the layer.

The ink jet fluid (that is mixture of solvent, binder and the mixture) preferably has a viscosity at 20° C. of 1 to 100 mPa·s, particularly preferably 1 to 50 mPa·s and very particularly preferably 1 to 30 mPa·s.

The mixture or a formulation of embodiments according to the present invention can additionally include one or more further components like for example surface-active compounds, lubricating agents, wetting agents, dispersing agents, hydrophobing agents, adhesive agents, flow improvers, de-foaming agents, deaerators, diluents which may be reactive or non-reactive, auxiliaries, colorants, dyes or pigments, sensitizers, stabilizers, or inhibitors.

The cells and/or cell tissue treatment device of embodiments can have any shape, be rigid or flexible. The device requires energy supply in any form. The energy supply may be directly associated to the device or separated by, e.g., a cable. A battery, particularly a printable battery, may be attached to the device in order to provide a device which is comfortable for the subject to be treated forming a totally self-contained portable unit. Irradiation may, thus, occur at any time and at any place without disturbing the subject to be treated in its habits or daily life. Home use of devices according to the present invention is particularly preferable. The device may be self adhesive and detachable. It may conform a planar or non-planar portion of the body or be an implantable probe.

The device may include an interactive steering unit. The steering unit may allow a switch from continuous illumination to pulsed illumination. It also may allow the precise adaptation of irradiation intensities and/or wavelengths to be emitted. The steering unit may be directly associated to the device. It can also be separated via a permanent or temporary linkage. The device may be disposable and is suitable for uses in the hospital or outside the hospital.

In any case the cells and/or cell tissue treatment device according to the present invention is suitable as light weight device for portable use. However, stationary devices can also be prepared. The device is sufficiently portable to enable ambulatory treatment i.e. treatment in which the subject can move around freely. It can be subsequently removed in the human subject's own time, so that treatment could take place almost everywhere and anytime. This results in a better convenience and lower costs (from avoiding either an out-patient or inpatient stay in hospital).

In the case of PDT the treatment is often associated with pain. Ambulatory cells and/or cell tissue treatment devices according to the present invention can be used with lower light levels since exposure can occur for a longer period of time. This overcomes a problem of pain induced in some patients by the high irradiances from conventional sources used in hospitals. In addition lower irradiance is more effective in PDT due to reduction of the extent of photobleaching of the photopharmaceutical.

The cells and/or cell tissue treatment devices may be provided with a photochemical and/or a photopharmaceutical preparation, e.g. as a topical composition. This may be in the form of a gel, ointment or cream. Alternatively, or as well, the device may be provided with a thin film impregnated with the photopharmaceutical. Typically, the photopharmaceutical preparation is provided as a layer in contact with the light source. Provided that the photopharmaceutical preparation is transparent or sufficiently translucent for the frequency of stimulating light, the resulting device can be readily applied without a separate step of applying the photopharmaceutical to a patient. Creams which would scatter the light may nevertheless be used if they are absorbed before the light source is switched on. A photopharmaceutical layer may be covered by a peelable release medium, such as a silicone-backed sheet. The photopharmaceutical preparation may include an inactive compound which is metabolised in vivo to an active compound. Delivery of the photopharmaceutical can be assisted by iontophoresis.

The output of light from the organic light-emitting semiconductor may be pulsed and an electronic control circuit or microprocessor may be provided to control this pulsing and/or other aspects of device function such as duration of exposure(s) of the area to be treated and the intensity of emitted light. Pulsed devices may be provided with a preparation of a photochemical and/or a photopharmaceutical substance which is photobleachable or which is metabolised in vivo to a photobleachable chemical species.

The output of the cells and/or cell tissue treatment device may take the form of a train of pulses, preferably in which the duration of the pulses is substantially the same as the interval between successive pulses. The period of the pulse train may, for example, be in the range of 20 ms to 2000 s, depending on the photobleaching characteristics of said substance. Preferably, the attachment means includes an adhesive surface to enable the device to be attached to a patient.

Preferably, the cells and/or cell tissue treatment device is ambulatory and is provided with a photochemical and/or a photopharmaceutical preparation. Preferred features of the preparation and its delivery are as above. In particular, the photochemical and/or photopharmaceutical may be photobleachable or may be metabolized in vivo to a photobleachable chemical species.

The means for activating and deactivating the cells and/or cell tissue treatment device may control other aspects of device function such as duration of exposure(s) of the area to be treated and the intensity of emitted light. The control means may to advantage be operable to cover the source to emit a pulse train having any one or more of the preferred features of the pulse train produced by a device in accordance with the first aspect of the invention. Suitable cells and/or cell tissue treatment devices according to the present invention may be formed as or may be included in any element selected from sleeves, bandages, pads, plaster, implantable probes, nasogastric tubes, chest drains, stents, clothe like devices, blankets, sleeping bags, devices fitting one or more teeth in the mouth, and patches.

The cells and/or cell tissue treatment device may be used as a stent, for example a tube of 1.25 to 2.25 cm radius of say 10 to 12 cm length for use inside the oesophagus.

The cells and/or cell tissue treatment device may be a blanket or sleeping bag in order to treat, e.g., jaundice of infants. Currently infants suffering from jaundice are separated from their parents and illuminated in incubators blindfold. This represents an unpleasant situation for both the infant and the parents. In addition, the infant is not able to adjust his body temperature as easily as adults can do and overheating in the incubator is a critical issue. Flexible blankets and sleeping bag provide a way to treat the infant without these problems. The infant covered by the blanket or sleeping bag can be irradiated while laying in his parents' arms and overheating of the infant's body is not as critical as compared to traditional therapies. This is due to the fact that the devices according to the present invention require less power and produce, in turn, less heat.

In psoriatic patients plaques are often found in body folds. Conventional phototherapy represents a problem which is due to the fact that light emitted by a light source does not reach the plaque in the body folds. OLEDs theoretically offer the opportunity to design a light source with direct contact to the psoriatic skin in the body fold. As outlined above curved surfaces represent a technical difficulty when manufacturing OLEDs. The problem can, however, be solved with OLECs and/or QD-LECs. OLECs and/or QD-LECs can be designed to fit into body folds in order to treat psoriasis and other diseases and/or conditions found in body folds.

The cells and/or cell tissue treatment device itself may include a therapeutic agent which is released in a controlled way during the treatment.

Preferably the cells and/or cell tissue treatment device include a plastic ionic material as described above, which has a glass transition temperature $T_g$ or melting point in the range between 25 and 45° C. Thus, the device will getting softer when attached to the skin in order to get a better contact to the skin.

In a further preferred embodiment the cells and/or cell tissue treatment device according to the present invention is an ambulatory device.

The present invention also relates to a cells and/or cell tissue treatment device, characterized in that it includes an attachment means for attaching the device to a patient.

The device can be self adhesive or can be temporarily fixed at the side of action with an auxiliary material such as a glue strip. The said device is characterized in that it can be a plaster, bandage, blanket, sleeping bag, sleeve, implantable probe, nasogastric tube, chest drain, pad, stent, and patch. The form and shape of the device can be tailored according to the individual needs of the treatment and according to the constitution of the subject to be treated.

The present invention also relates to a device according to this invention, characterized in that the device includes a power supply unit or an interface for a external power supply. As outlined above the power supply can be a directly attached to the device. This allows the design of ultra-thin devices which, e.g., can be used under the clothes without disturbing the subject to be treated. The power supply can also be in a more separated unit which is connected to the device in any possible way in order to supply the power.

The cells and/or cell tissue treatment device according to the present invention is intended to illuminate parts of the subject. A device characterized in that the device is used in the treatment and/or prophylaxis therapeutic and/or cosmetic diseases and conditions in animals and humans.

The cells and/or cell tissue treatment device according to the present invention emits electromagnetic radiation to cause said treatment and/or prophylaxis of the area, wherein in some embodiments the LEC, QD-LEC and/or QD-OLED has an extent of at least 0.5 cm$^2$. The LEC, QD-LEC and/or QD-OLED can be continuous or discontinuous. The LEC, QD-LEC and/or QD-OLED and its illuminating area can adopt any shape that is suitable for the treatment. This can, in particular in therapeutic conditions, prevent side effects through the irradiation of parts of the subject whose treatment is not required.

In a further preferred embodiment the cells and/or cell tissue treatment device of the present invention has an extent between 0.5 cm$^2$ and 100000 cm$^2$, particularly preferably between 0.5 cm$^2$ and 50000 cm$^2$ The cells and/or cell tissue treatment according to the present invention can be used to treat medical and/or cosmetic conditions. Hereby any therapeutic strategy is included, ie. treatment of a subject with light can be performed with or without a combination with other treatment approaches.

Treatment can, for example, be carried out with one or more wavelengths in one or more cells and/or cell tissue treatment devices of the present invention. Furthermore, in addition to said OLEC, QD-LEC, and/or QD-OLED, further light sources using different technologies can be used for the treatment, such as LEDs, OLEDs, and lasers. In addition, the treatment with said cells and cell tissue treatment device can be combined with any known treatment strategy using drugs and cosmetics.

In other embodiments, the cells and/or cell tissue treatment device may be used in combination with a medical composition.

Hence, the invention also relates to a kit of parts for treatment of cells and/or cell tissue, including a device of any of the preceding claims and a topical composition or a topical chromophore composition.

In the kit of parts according to embodiments, the topical composition or the topical chromophore composition may be encapsulated or microencapsulated in a vehicle. Thereby, the composition may be transported to the cell or cells to be treated in a target-oriented way.

Further, the topical composition may include at least one element chosen from naturally occurring chlorophyll-containing compounds, carotenoid-containing compounds, phyocobilin compounds, indocyanine green, methylene blue, rose Bengal, Vitamin C, Vitamin E, Vitamin D, Vitamin A, Vitamin K, Vitamin F, Retin A (Tretinoin), Adapalene, Retinol, Hydroquinone, Kojic acid, a growth factor, echinacea, an antibiotic, an antifungal, an antiviral, a bleaching agent, an alpha hydroxy acid, a beta hydroxy acid, salicylic acid, antioxidant triad compound, a seaweed derivative, a salt water derivative, algae, an antioxidant, a phytoanthocyanin, a phytonutrient, plankton, a botanical product, a herbaceous product, a hormone, an enzyme, a mineral, a cofactor, an antiaging substance, insulin, minoxidil, lycopene, a natural or synthetic melanin, a metalloproteinase inhibitor, proline, hydroxyproline, an anesthetic, chlorophyll, bacteriochlorophyll, copper chlorophyllin, chloroplasts, carotenoids, phycobilin, rhodopsin, anthocyanin, inhibitors of ornithine decarboxylase, inhibitors of vascular endothelial growth factor (VEGF), inhibitors of phospholipase A2, inhibitors of S-adenosylmethionine, licorice, licochalone A, genestein, soy isoflavones, phtyoestrogens, derivative, analogs, homologs, and subcomponents thereof, and derivatives, subcomponents, immunological complexes and antibodies of said cells or cell tissue, and synthetic and natural analogs thereof, combinations thereof.

The topical chromophore composition may have at least one absorption maximum between 300 nm and 1300 nm and may include an active ingredient selected from the group consisting of chlorophyll, porphyrin, and combinations thereof. The active ingredient may have at least one metal-ligand bond, wherein the metal in the metal-ligand bond is selected from the group consisting of Fe, Mg, Cu, Al, reactive transition metals, metal chelates, and antibody complexes.

The cells and/or cell tissue treatment device or kit of parts of any embodiment may be used for treating at least one element chosen from plant cells, animal cells, human cells, mammalian cells, eucaryotic cells, procaryotic cells, hair cells, hair root cells, skin cells, mucosal cells, and stem cells. The device or a kit of parts of any embodiment may be used for cosmetic treatment; prophylactic treatment; therapeutic treatment; non-invasive treatment; activation, stimulation, deactivation, disinfection, depilation, phototherapy, photodynamic therapy, extracorporeal treatment, intracorporeal treatment of cells and/or cell tissue; peeling and/or lifting of cell tissue; and/or activation or inhibition of the differentiation of stem cells.

For example, reduction, elimination or stimulation of hair growth can be achieved. Such a treatment may include the photomodulation of hair follicles, hair bulb, hair bulge, stem cells, glandular and duct activity and the surrounding tissue to produce temporary or permanent stimulation of activity of surrounding tissue or supporting tissue in human or mammalian skin, of some or all of the hairs. The process typically produces little or no permanent injury or damage to nearby skin tissue. Primarily, only the hair and immediately surrounding tissue are affected.

In another embodiment, the cells and/or cell tissue treatment device of embodiments may be used for prevention of acne and acne scarring by treating sebaceous oil glands and the surrounding tissue with the topical composition or topical chromophore composition, e.g. Na Cu Chlorophyllin and carotenoids, as a photomodulation enhancing agent and then exposing the target tissue to light of about 450 nm from the cells and/or cell tissue treatment device, in order to inhibit the activity of the oil gland and eliminate acne bacteria. This effect can be supported by enhancing the penetration of the topical composition into the oil gland and surrounding tissue through the use of procedures including enzyme peeling, microderm abrasion, or ultrasound. For example, a naturally occurring native chromophore may be applied to the skin proximate to or directly to a sebaceous oil gland and/or fed to the tissue of a sebaceous oil gland. Then, the photomodulating enhancing agent is exposed to electromagnetic radiation from the cells and/or cell tissue treatment device including at least one dominant emissive wavelength suitable for reducing the number of acne bacteria.

In another example, the cells and/or cell tissue treatment device of embodiments may be used for producing preferential damage to hair exiting mammalian skin, e.g. for depilation. A topical agent is used which has an electromagnetic radiation absorption characteristic which enables the agent to absorb a first wavelength of electromagnetic radiation from the cells and/or cell tissue treatment device of embodiments. The topical agent is applied to the skin so that the agent penetrates the skin and attaches to or becomes physically incorporated into the hair shaft, the hair follicle, the hair bulb or the hair duct. The agent is exposed to the first wavelength of electromagnetic radiation and absorbs the first wavelength of electromagnetic radiation, thereby depilating the skin region treated. The agent may have an average diameter of about one micron. The agent may further be encapsulated in a microencapsulation vehicle, which may have an average diameter of about one micron. The skin region may in addition be treated with an external enzyme, ultrasound. The topical agent may include chlorophyll which may be encapsulated.

If phototherapy is combined with the treatment of chemical compounds such as a drugs and/or cosmetics, light can be used to initiate a (photo-) chemical reaction or activation of the chemical compounds, which is called photodynamic therapy (PDT). Phototherapy according to the present invention can also be used in conjunction with chemical compounds without initiating a photochemical reaction or activation. Synergistic effects for the effectiveness and safety of the treatment of a therapeutic disease can arise from sequential, parallel, and overlapping treatment with both light therapy and drugs and/or cosmetics. The drug(s) or cosmetic compound(s), e.g., can be administered first for a specific time period followed by the application of phototherapy using the cells and/or cell tissue treatment device according to the present invention. The time gap between both treatments may also vary, depending on the drug, its photoreactivity, individual circumstances of the subject, and the specific disease or condition. Both treatments may also overlap timely either partly or completely. The exact treatment strategy will depend on the individual circumstances and the severity of the disease or condition.

The combination therapy can have a synergistic effect and can reduce the side effects of traditional treatment strategies (e.g. the side effects of tetracyclines). This is, at least in part, due to the fact, that smaller doses of the drugs may be required when following the combined approach as outlined herein.

Treatment is any exposure of a subject to the radiation of said OLEC, QD-LEC and/or QD-OLED. The treatment may be performed by direct contact between the subject and the device including the OLEC, QD-LEC and/or QD-OLED or without direct contact between them. The treatment may be outside or inside the subject. Treatment outside the subject may be, for instance, treatment of the skin, wounds, eye, gingival, mucosa, tongue, hair, nail bed, and nails. Treatment inside the subject may be, for instance, blood vessels, heart, breast, lung, or any other organ of the subject. Particular devices are required for most applications inside the subject. One such example may be a stent including the cells and cell tissue treatment device according to the present invention. The subject may preferably be a human or an animal. The term cosmetic also includes aesthetic applications.

The wavelength of light that is emitted by the OLEC, QD-LEC, and/or QD-OLED) and/or devices can be precisely tailored by the selection of the appropriate components of the OLEC, QD-LEC and/or QD-OLED. This includes, as outlined above, the specific design of the quantum dots and the use of different emitters or colour filter and colour converter. Depending on the application of the OLEC, QD-LEC and/or QD-OLED each therapeutic or cosmetic treatment requires a more or less defined wavelength or spectrum of wavelengths to be emitted.

The OLEC, QD-LEC and/or QD-OLED preferably emits light and or irradiation in the range between 200 and 1000 nm, preferably between 300 and 1000 nm, particularly preferably between 300 and 950 nm, and very particularly preferably between 400 and 900 nm.

As outlined above one effect of phototherapy is the stimulation of metabolism in the mitochondria. After phototherapy, the cells show an increased metabolism, they communicate better and they survive stressful conditions in a better way.

The cells and/or cell treatment device can be used for cellular stimulation. Preferred wavelengths or ranges of wavelengths for cellular stimulation are in the range between 600 to 900 nm, particularly preferable between 620 and 880 nm, and very particularly preferably between 650 and 870 nm. Examples of particularly preferred wavelengths for cellular stimulation are 683.7, 667.5, 772.3, 750.7, 846, and 812.5 nm.

The present invention also relates to a method for treatment of cells and/or cell tissue, including exposing cells or cell tissue to light emitted from a cell and/or cell tissue treatment device of any embodiment described herein. As mentioned above, the cell and/or cell tissue treatment device includes at least one light source chosen from an organic light emitting electrochemical cell (OLEC), a light emitting electrochemical cell including at least one quantum dot (QD-LEC), and a organic light emitting device including at least one quantum dot (QD-OLED).

In some embodiments of the method according to the invention, the step of exposing cells or cell tissue to light includes emitting multichromatic and/or narrowband light and/or light in the yellow wavelength range and/or light in the infrared wavelength range.

For instance, the step of exposing cells or cell tissue to light includes emitting multichromatic light having a effective radiated power ratio of about 4:1 of yellow light to infrared light. In particular, the step of exposing cells or cell tissue to light may include emitting multichromatic light including yellow light of about 590 nm at an effective radiated power of about 4 mW/cm$^2$ and infrared light of about 850 nm at an effective radiated power of about 1 mW/cm$^2$.

In the method of embodiments light may be emitted from the at least one element chosen from OLEC, QD-LEC, QD-OLED at a wavelength from about 300 nm to about 1300 nm, and/or at a total energy fluence of less than 10 J/cm$^2$.

In some embodiments, the method is for treatment of collagen, fibroblast, and fibroblast-derived cell levels in mammalian tissue. This embodiment may include exposing said tissue to light from the cells and/or cell tissue treatment device having a dominant emissive wavelength of from about 300 nm to about 1600 nm for a period of time of from about 10 seconds to about 24 hours, wherein the energy fluence received by said tissue is less than about 10 J/cm$^2$.

In the method, the light may be emitted in a pulsed way, for instance at pulses having a duration of from about 0.1 femtoseconds to about 100 seconds. The interpulse delay being between said pulses being from about 0.1 to about 1000 milliseconds. For instance, wrinkle reduction can be performed using a pulsed cells and/or cell tissue treatment device by exposing skin tissue to the light with 250 millisecond pulses, an interpulse delay of 100 milliseconds, and 100 repetitions, resulting in a total energy fluence of 70.0 mJ/cm$^2$. The light source may have a dominant emissive wavelength at 574 nm.

The method of embodiments may include emitting light from the further light source chosen from a light emitting diode, a laser, a fluorescent light source a light emitting polymer, a xenon arc lamp, a metal halide lamp, a filamentous light source, an intense pulsed light source, a sulfur lamp, and combinations thereof, wherein the at least one further light source is adapted to emit light at a wavelength from about 400 nm to about 1600 nm. Further, the cells or cell tissue may be exposed to ultrasound. The intensity of infrared radiation received by the cells and/or cell tissue may be reduced. Moreover, the emitted light may be filtered for selecting a wavelength or a wavelength band. In addition, the cells or cell tissue can be cooled, e.g. before, during or after the treatment.

In one embodiment of the method, a topical composition or a topical chromophore composition may be applied to the cells or cell tissue before, during or after exposing the cells or the cell tissue to the light. Examples of the topical composition or topical chromophore composition are given above.

The method of embodiments may be used for cosmetic treatment; prophylactic treatment; therapeutic treatment; non-invasive treatment; activation, stimulation, deactivation, disinfection, depilation, phototherapy, photodynamic therapy, extracorporeal treatment, intracorporeal treatment of cells and/or cell tissue; peeling or lifting of cell tissue; and/or activation or inhibition of the differentiation of stem cells. The cells or the cells of the cell tissue may be at least one element chosen from plant cells, animal cells, human cells, mammalian cells, eucaryotic cells, procaryotic cells, hair cells, hair root cells, skin cells, mucosal cells, and stem cells.

In some embodiments of the method, the treatment is no treatment of the human or animal body by surgery or therapy and/or is not practiced on the human or animal body.

Any therapeutic disease and/or cosmetic condition approachable by phototherapy can be treated with the cells and/or cell treatment device according to the present invention and said devices. These diseases and/or conditions include, e.g., skin diseases, and skin-related conditions including skin-ageing, and cellulite, enlarged pores, oily skin, folliculitis, precancerous solar keratosis, skin lesion, aging, wrinkled and sun-damaged skin, crow's feet, skin ulcers (diabetic, pressure, venous stasis), acne rosacea lesions, cellulite; photomodulation of sebaceous oil glands and the surrounding tissues; reducing wrinkles, acne scars and acne bacteria, inflammation, pain, wounds, psychological and neurological related diseases and conditions, edema, Pagets disease, primary and metastatic tumors, connective tissue disease, manipulation of collagen, fibroblast, and fibroblast derived cell levels in mammalian tissue, illuminating retina, neoplastic, neovascular and hypertrophic diseases, inflammation and allergic reactions, perspiration, sweating and hyperhydrosis from eccrine (sweat) or apocrine glands, jaundice, vitiligo, ocular neovascular diseases, bulimia nervosa, herpes, seasonal affective disorders, mood, sleep disorders, skin cancer, crigler naijar, atopic dermatitis, diabetic skin ulcers, pressure ulcers, bladder infections, relief of muscular pains, pain, stiffness of joints, reduction of bacteria, gingivitis, whitening teeth, treatment of teeth and tissue in mouth, wound healing.

Cosmetic conditions are preferably selected from acne, skin rejuvenation and skin wrinkles, cellulite, and vitiligo. Many therapeutic treatments also have cosmetic component. Psoriasis, e.g., can be mild, mild-to-moderate, moderate, moderate-to-severe and severe. Any of these categories has a cosmetic component, which may be responsible for severe psychological problems of affected patients.

Preferably the cells and/or cell treatment device is used for the treatment and/or prophylaxis of humans and/or animals. Preferably the cells and/or cell treatment device according to the present invention is used for the treatment and/or prophylaxis of humans.

Further subjects suitable to be treated by the irradiation with cells and/or cell treatment device according to the present invention are plants, microbes, bacteria, fungi, and liquids. Microbes include, but are not limited to, prokaryotes such as bacteria and archaea and eukaryotes such as protists, animals, fungi and plants. Preferred liquids are beverages and particularly preferably water.

Skin as used herein is defined as the largest organ of the integumentary system including hair, scales, feathers and nails. The term skin also includes the tongue, mucosa and gingival.

As already mentioned, principally any therapeutic and cosmetic condition that is approachable by phototherapy is covered by the present invention. The distinction between the terms therapeutic and cosmetic depends, as outlined above, on individual circumstances, the severity of the condition and the assessment of the physician. As outlined in this invention many therapeutic conditions are associated with cosmetic effects, independent of the severity of the therapeutic disease.

The skin diseases and skin related conditions include, but are not limited to acneiform eruptions, autoinflammatory skin diseases or conditions, chronic blistering, conditions of the mucous membranes, conditions of the skin appendages, conditions of the subcutaneous fat, connective tissue diseases, abnormalities of dermal fibrous and elastic tissue, dermal and subcutaneous growths, dermatitis, atopic dermatitis, contact dermatitis, eczema, pustular dermatitis, seborrheic dermatitis and eczema, disturbances of pigmentation, drug eruptions, endocrine-related diseases and conditions, epidermal nevi diseases and conditions, neoplasms, cysts, erythemas, genodermatoses, infection-related diseases and conditions, bacterium-related diseases and conditions, mycobacterium-related diseases and conditions, mycosis-related diseases and conditions, parasitic infestations, stings, and bites, virus-related diseases and conditions, lichenoid eruptions, lymphoid-related diseases and conditions, melanocytic nevi and neoplasms, monocyte- and macrophage-related diseases and conditions, mucinoses, neurocutaneous, noninfectious immunodeficiency-related diseases and conditions, nutrition-related diseases and conditions, papulosquamous hyperkeratotic related diseases and conditions, pruritic related diseases and conditions, psoriasis (mild, mild to severe, and severe), reactive neutrophilic diseases and conditions, recalcitrant palmoplantar eruptions, diseases and conditions resulting from errors in metabolism, diseases and conditions resulting from physical factors, urticaria and angioedema, vascular-related diseases and conditions, and periodontitis or other diseases and conditions of the gingival.

Skin related diseases and conditions also include skin tumors, pre-malignant tumors, malignant tumors, cell carcinomas, secondary metastasis, radiodermatitis and keratosis.

The healing of wounds can also be assigned to skin diseases and skin related conditions. Wound healing can, hereby, occur at the outer surface of the subject to be treated, at its internal parts, at the skin, eye, nail or nail bed, any surface in the subject's mouth, and at the mucosa, gingival, epithelial surface of the vascular system or other part of the subjects body.

Preference is given to the treatment and/or prophylaxis and/or diagnosis of skin diseases and/or cosmetic skin conditions selected from acne, psoriasis, eczema, dermatitis, atopic dermatitis, atopic eczema, edema, vitiligo, skin ageing, skin, wrinkles, skin desensibilization, Bowens disease, tumors, pre-malignant tumors, malignant tumors, basal cell carcinomas, squamous cell carcinomas, secondary metastases, cutaneous T-cell lymphomas, solar keratosis, arsenical keratosis, radiodermatitis, skin redness, comedo, and cellulite.

The cells and/or cell treatment device according to the present invention can be used in cosmetics for skin care and skin repair, e.g. as light plaster. The wavelengths or range of wavelengths emitted by said LEC, QD-LEC and/or QD-OLED and/or devices is in the range between 400 and 800 nm, preferably between 450 and 750 nm, particularly preferably between 500 and 700 nm, and very particularly preferably between 580 and 640 nm.

Preferred skin diseases and skin-related conditions are selected from acne, psoriasis, eczema, edema, dermatitis, atopic dermatitis, vitiligo, Bowens disease, tumors, pre-malignant tumors, malignant tumors, basal cell carcinomas, squamous cell carcinomas, secondary metastases, cutaneous T-cell lymphomas, solar keratosis, arsenical keratosis, radiodermatitis, and cellulite.

Further preferred skin diseases and skin-related conditions are selected from psoriasis, polymorphous light eruption, solar urticaria, actinic reticuloid atopic eczema, vitiligo, pruritus, lichen planus, early cutaneous T-cell lymphoma, dermographism, and pityriasis lichenoides. Preferably theses diseases and conditions are treated with light having a wavelength or a range of wavelengths between 200 and 500 nm, particularly preferably between 250 and 400 nm, and very particularly preferably between 270 and 350 nm.

The cells and/or cell treatment device can be used for PUVA therapy. PUVA therapy is derived from the therapeutic application of psoralen (7H-furo[3,2-g]chromen-7-one) and derivatives thereof together with UV-A light. PUVA can be employed for the treatment of skin diseases characterized by hyperproliferative conditions. Psoralen is the parent compound in a family of natural products. It is structurally related to coumarines and can preferably be used for the treatment of psoriasis, eczema, vitiligo, mycosis fungoides, cuntaneous T-cell lymphoma, and other autoimmune diseases. With PUVA can also bet treated atopic eczema, lichen planus, urticaria pigmentosa, polymorphous light eruption, and alopecia greata.

Psoralen can be administered orally or topically to the skin. Preferred compounds are psoralen, 8-methoxypsoralen (8-MOP), 5-methoxypsoralen (5-MOP), and 4,5', 8-trimethylpsoralen (TMP). After oral administration of 8-MOP, patients become gradually reactive to UV-A and therefore to photochemotherapeutic treatment. The patients are maximally reactive 2 to 3 hours after ingestion of the drug, and during this period the irradiation is carried out. In the case of vitiligo khellin can be used instead of psoralen. The combined treatment with light and khellin is often called KUVA.

The cells and/or cell treatment device of the present invention can also be used for photopheresis. Photophoreresis is a process by which peripheral blood is exposed in an extracorporeal flow system to photoactivate 5-MOP and represents a treatment for disorders caused by aberrant T lymphocytes. It is a therapy for advanced cutaneous T-cell lymphoma, pemphigus vulgaris and progressive systemic sclerosis (scleroderma). It can be used to treat autoimmune disorders. Further diseases that can be treated include multiple sclerosis, organ transplant rejection, rheumatoid arthritis, and AIDS.

The present invention particularly refers to a cells and/or cell treatment device for the treatment of acneiform eruptions. The term acneiform eruption refers to a group of dermatoses including acne vulgaris, rosacea, folliculitis, and perioral dermatitis. Acneiform eruptions are, generally spoken, caused by changes in the pilosebaceous unit and are selected from acne aestivalis (Mallorca acne), acne conglobata, acne cosmetica, acne fulminans (acute febrile ulcerative acne), acne keloidalis (acne keloidalis nuchae, dermatitis papillaris capillitii, folliculitis keloidalis, folliculitis keloidis nuchae, nuchal keloid acne), acne mecanica, acne medicamentosa, acne miliaris necrotica (acne varioliformis), acne vulgaris, acne with facial edema (solid facial edema), acneiform eruptions, blepharophyma, erythrotelangiectatic rosacea (erthemaotelangiectatic rosacea), excoriated acne (acne excoriee des jeunes filles, Picker's acne), glandular rosacea, gnathophyma, gram-negative rosacea, granulomatous facial dermatitis, granulomatous perioral dermatitis, halogen acne, hidradenitis suppurativa (acne inversa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum), occupational acne, ophthalmic rosacea (ocular rosacea, ophthalmorosacea), otophyma, persistent edema of rosacea (chronic upper facial erythematous edema, Morbihan's disease, Rosaceous lymphedema), pomade acne, papulopustular rosacea, perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobata, rosacea fulminans, SAPHO syndrome, steroid rosacea, tropical acne.

Acne vulgaris (commonly called acne) is a common skin condition, caused by changes in pilosebaceous units, skin structures consisting of a hair follicle and its associated sebaceous gland, via androgen stimulation. It is characterized by noninflammatory follicular papules or comedones and by inflammatory papules, pustules, and nodules in its more severe forms. Acne vulgaris affects the areas of skin with the densest population of sebaceous follicles; these areas include the face, the upper part of the chest, and the back. Severe acne is inflammatory, but acne can also manifest in noninflammatory forms. Acne lesions are commonly referred to as pimples, blemishes, spots, zits, or simply acne.

Acne occurs most commonly during adolescence, affecting more than 89% of teenagers, and frequently continues into adulthood. In adolescence, acne is usually caused by an increase in male sex hormones, which people of both genders accrue during puberty. For most people, acne diminishes over time and tends to disappear—or at the very least decrease—after one reaches one's early twenties. There is, however, no way to predict how long it will take to disappear entirely, and some individuals will carry this condition well into their thirties, forties and beyond.

The face and upper neck are the most commonly affected, but the chest, back and shoulders may have acne as well. The upper arms can also have acne, but lesions found there are often keratosis pilaris. Typical acne lesions are comedones, inflammatory papules, pustules and nodules. Some of the large nodules are also called cysts and the term nodulocystic has been used to describe severe cases of inflammatory acne.

Aside from scarring, its main effects are psychological, such as reduced self-esteem and, in some cases, depression or suicide. Acne usually appears during adolescence, when people already tend to be most socially insecure. Early and aggressive treatment is therefore advocated by some to lessen the overall impact to individuals.

Light exposure can be used as treatment for acne. Used twice weekly, this has been shown to reduce the number of acne lesions by about 64% and is even more effective when applied daily. The mechanism appears to be that a porphyrin (Coproporphyrin III) produced within P. acnes generates free radicals when irradiated by 420 nm and shorter wavelengths of light. Particularly when applied over several days, these free radicals ultimately kill the bacteria. Since porphyrins are not otherwise present in skin, and no UV light is employed, it appears to be safe.

The treatment apparently works even better if used with a mixture of the violet/blue light and red visible light (e.g. 660 nm) resulting in a 76% reduction of lesions after three months of daily treatment for 80% of the patients; and overall clearance was similar or better than benzoyl peroxide. Unlike most of the other treatments few if any negative side effects are typically experienced, and the development of bacterial resistance to the treatment seems very unlikely. After treatment, clearance can be longer lived than is typical with topical or oral antibiotic treatments; several months is not uncommon. In addition, basic science and clinical work by dermatologists has produced evidence that intense blue/violet light (405 to 425 nm) can decrease the number of inflammatory acne lesion by 60 to 70% in four weeks of therapy, particularly when the P. acnes is pre-treated with delta-aminolevulinic acid (ALA), which increases the production of porphyrins.

The present invention therefore also relates to a combination of the cells and/or cell treatment device and active drugs or active ingredients for the treatment of therapeutic diseases and/or cosmetic conditions. In particular, the present invention relates to the combined use of the cells and/or cell treatment device and drugs used for the treatment of acne. The drugs can be selected from any drugs typically employed in order to treat acne, such as antibiotics (topical and/or oral), hormonal treatments, topical retinoids, topical bactericidals, sulfur. Suitable topical bactericidals are, for example, benzoyl peroxide, triclosan, and chlorhexidine gluconate. Suitable topical antibiotics are, for example, erythromycin, clindamycin, and tetracycline. Suitable oral antibiotics are, for example, erythromycin, tetracycline antibiotics (e.g. oxytetracycline, doxycycline, minocycline, or lymecycline), trimethoprim, and minocycline.

Suitable hormones are, e.g., selected from estrogen, progestogen, a combination of estrogen and progestogen, cyproterone, oestrogen, a combination of cyproterone and oestrogen, drospirenone, spironolactone, and cortisone. Suitable oral retinoids are, for example, vitamin A derivatives such as isotretinoin (e.g. Accutane, Amnesteem, Sotret, Claravis, Clarus). Suitable topical retinoids are, for example, tretinoin (e.g. Retin-A), adapalene (e.g. Differin), tazarotene (e.g. Tazorac), isotretinoin, and retinol. Further suitable drugs are, e.g. selected from anti-inflammatory drugs.

The cells and/or cell treatment device according to the present invention can also be used in combination with dermabrasion to treat or prevent acne. Dermabrasion is a cosmetic medicinal procedure in which the surface of the skin is removed by abrasion (sanding).

Hereby any therapeutic strategy is included. The drug, e.g., can be administered first for a specific time period followed by the application of phototherapy using the cells and/or cell treatment device according to the present invention. The time gap between both treatments may also vary, depending on the drug, its photoreactivity, individual circumstances of the subject, and the specific disease or condition. Both treatments may also overlap timely either partly or completely. The exact treatment strategy will depend on the individual circumstances and the severity of the disease or condition.

The combination therapy can have a synergistic effect and can reduce the side effects of traditional treatment strategies (e.g. the side effects of tetracyclines). This is due to the fact, that smaller doses of the drugs may be required when following the combined approach as outlined herein.

Comedones, also called blackhead, can also be treated by phototherapy employing the cells and/or cell treatment device according to the present invention. A comedon is a yellow or blackish bump or plug on the skin. Actually, it is a type of acne vulgaris. Comedones are caused by excess oils that have accumulated in the sebaceous gland's duct. The substance found in these bumps mostly consists of keratin and modified sebum, which darkens as it oxidizes. Clogged hair follicles, where blackheads often occur, reflect light irregularly to produce a comedon. For this reason, the blockage might not necessarily look black when extracted from the pore, but may have a more yellow-brown colour as a result of its melanin content.

In contrast, a so called whitehead, which is also called closed comedo, is a follicle that is filled with the same material, sebum, but has a microscopic opening to the skin surface. Since the air cannot reach the follicle, the material is not oxidized, and remains white.

The cells and/or cell treatment device according to the present invention used for the treatment of acne preferably includes at least one organic electroluminescent compound which emits light in the range between 350 and 900 nm, preferably between 380 and 850 nm, particularly preferably between 400 and 850 nm, and very particularly preferably between 400 and 800 nm.

Further particularly preferred light for the treatment of acne is blue light. Preferred blue light has emission wavelengths for the treatment of acne are 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429 and 430 nm. For example 414 and 415 nm are particularly suitable in order to kill P. acnes bacteria and to help cure existing blemishes and to prevent further outbreaks.

Studies on the application of phototherapy to treat acne revealed that a combination of different wavelengths or ranges of wavelengths are particularly suitable to treat acne efficiently. Particularly preferred is therefore a combination of red light and blue light to treat acne. The said red light is preferably selected from the range between 590 to 750 nm, particularly preferably between 600 and 720 nm, and very particularly preferably between 620 and 700 nm. Two further preferred wavelengths for the treatment of acne are 633 and 660 nm. The blue light can be selected from the wavelengths as described above.

In the case of comedo LEC, QD-LEC and/or QD-OLED including light emitting compound(s) emitting light with a wavelength of 500 nm or light in the range between 500 and 700 nm are particularly preferred.

Cellulite describes a condition that is claimed to occur in most women, where the skin of the lower limbs, abdomen, and pelvic region becomes dimpled. The causes of cellulite are poorly understood and may involve changes in metabolism and physiology such as gender specific dimorphic skin architecture, alteration of connective tissue structure, vascular changes and inflammatory processes. A couple of therapies are applied to prevent or to treat cellulite. Heat and the increase of blood flow are two common techniques. Therefore light therapy is considered to be beneficial to individuals suffering from cellulite. Devices according to the present invention are suitable for the treatment and/or prophylaxis of cellulite. PDT is also suitable for the treatment and/or prophylaxis of cellulite.

The wavelength for the treatment and/or prophylaxis of cellulite that is to be emitted by the cells and/or cell treatment device according to the present invention is in the range between 400 and 1000 nm, preferably in the range between 400 and 900 nm, particularly preferably between 450 and 900 nm, and very particularly preferably between 500 and 850 nm. The more general term skin ageing refers to both the formation of wrinkles and hyperpigmentation. The signs of ageing of the human skin resulting from the effects on the skin of intrinsic and extrinsic factors are defined by the appearance of wrinkles and fine lines, by the yellowing of the skin which develops a wizened appearance along with the appearance of pigmentation blemishes, by a change in the thickness of the skin, generally resulting in a thickening of the stratum corneum and of the epidermis and a thinning of the dermis, by disorganization of the elastin and collagen fibers which causes a loss of elasticity, of suppleness and of firmness, and by the appearance of telnagiectasia.

Some of these signs are more particularly associated with intrinsic or physiological ageing, that is so to say with "normal" ageing associated with age, whereas others are more specific to extrinsic ageing, that is so to say ageing caused by the environment in general; such ageing is more particularly photo-ageing due to exposure to the sun. Other factors causing ageing of the skin are atmospheric pollution, wounds, infections, traumatisms, anoxia, cigarette smoke, hormonal status, neuropeptides, electromagnetic fields, gravity, lifestyle (e.g. excessive consumption of alcohol), repetitive facial expressions, sleeping positions, and psychological stressors.

The changes in the skin which occur due to intrinsic ageing are the consequence of a genetically programmed sequence involving endogenous factors. This intrinsic ageing in particular causes slowing down of the regeneration of skin cells, which is reflected essentially in the appearance of clinical damage such as a reduction of the subcutaneous adipose tissue and the appearance of fine lines or small wrinkles, and in histopathological changes such as an increase in the number and thickness of the elastic fibers, a loss of vertical fibers from the elastic tissue membrane and the presence of large irregular fibroblasts in the cells of this elastic tissue.

In contrast, extrinsic ageing results in clinical damage such as thick wrinkles and the formation of flabby and weather-beaten skin, and in histopathological changes such as an excessive accumulation of elastic substance in the upper dermis and degeneration of the collagen fibers.

There are different biological and molecular mechanisms which are responsible for the ageing of the skin and the process is currently not fully understood. However, it was recognized that both intrinsic and extrinsic factors of ageing of the skin share common mechanisms [P. U. Giacomoni et al., Biogerontology 2004, 2, 219-229]. These factors trigger a process leading to the accumulation of damages in the skin resulting in skin ageing since the expression of cell adhesion molecules provokes recruitment and diapedesis of circulating immune cells, which digest the extracellular matrix (ECM) by secreting collagenases, myeloperoxidases and reactive oxygen species.

The activation of these lytic processes provokes random damage of these resident cells, which in turn secrete prostaglandins and leukotrienes. These signaling molecules induce the degranulation of resident mast cells which release the autacoid histamine and the cytokine TNFalpha thus activating endothelial cells lining adjacent capillaries which release P-selectin and the synthesis of cell adhesion molecules such as E-selectin and ICAM-1. This closes a self-maintained micro-inflammatory cycle, which results in the accumulation of ECM damage, i.e. skin ageing.

There is a strong cosmetic and therapeutic need for novel strategies for the treatment or prophylaxis of skin ageing. Various cosmetic and therapeutic compositions (including for skin care) intended inter alia to prevent or treat ageing of the skin are known. Retinoic acid and derivatives thereof have been described as anti-ageing agents in skin care, cosmetic, or dermatological compositions, in particular in U.S. Pat. No. 4,603,146. Hydroxy acids such as lactic acid, glycolic or alternatively citric acid are also known for this same application, these acids have been described in numerous patents and publications (e.g. EP-A-413528) and introduced into numerous skin care, cosmetic, or dermatological compositions on the market. Aromatic orthohydroxy acids such as salicylic acid have also been proposed (e.g. WO 93/10756 and WO 93/10755).

All of these compounds act against ageing of the skin by desquamation, that is to say removal of the dead cells at the surface of the stratum corneum. This desquamation is also referred to as a keratolytic property. However, these compounds also have side effects, consisting of stinging and redness, which the user finds unpleasant. Thus, there remains a need for anti-ageing methods which are at least as effective as the known compounds, but do not exhibit their drawbacks. Unlike the established strategies to treat or prevent skin ageing, modulating the selectin function is a novel concept intervening the micro-inflammation cascade at a very early stage and treating and preventing intrinsic and extrinsic skin ageing according to the present inventions represents a strategy without the drawbacks known from other strategies.

Phototherapy provides a new way to treat ageing of the skin. Thus, another subject of the invention is the use of the cells and/or cell treatment device according to the present invention for the treatment and/or prophylaxis of skin ageing. This means, that the present invention provides solutions, inter alia, for skin rejuvenation and to reduce or prevent the formation of wrinkles.

The wavelength for the treatment of skin ageing that is to be emitted by the cells and/or cell treatment device according to the present invention is in the range between 400 and 950 nm. Preferably the wavelength is in the range between 550 and 900 nm, and particularly preferably between 550 and 860 nm.

The cells and/or cell treatment device of the present invention may also emit light of different wavelengths or wavelength ranges which also applies for other embodiments of the present invention.

In another preferred embodiment of the present invention the cells and/or cell treatment device used for the treatment of skin ageing emits light in the range of 600 nm and 650 nm, particularly preferably in the range between 620 nm and 650 nm.

The cells and/or cell treatment device according to the present invention used for the treatment and/or prevention of skin ageing preferably includes at least one organic electroluminescent compound which emits light in the range between 350 and 950 nm, preferably between 380 and 900 nm, and particularly preferably between 400 and 900 nm.

Further particularly preferred light for the treatment and/or prophylaxis of skin ageing is blue light. Preferred blue light has emission wavelengths for the treatment and/or prophylaxis of skin ageing are 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, and 430 nm. For example 415 nm is particularly suitable.

Further particular preferred light for the treatment and/or prophylaxis of skin ageing has a wavelength between 400 and 900 nm.

Skin rejuvenation can also be achieved with light of the wavelength of 830 nm or slightly below or above that value. Therefore, cells and/or cell treatment device according to the present invention emitting light in the range between 700 nm and 1000 nm, preferably between 750 nm and 900 nm, particularly preferably between 750 nm and 860 nm, and very particularly preferably between 800 nm and 850 nm are also subject of the present invention.

Redness of the skin of a subject can be treated by a cells and/or cell treatment device according to the present invention. The wavelength for the treatment and/or prophylaxis of redness that is to be emitted by the devices according to the present invention is in the range between 460 and 660 nm. Preferably the wavelength is in the range between 500 and 620 nm, and particularly preferably between 540 and 580 nm. One particular preferred wavelength for this purpose is 560 nm. Dermatitis of a subject can be treated by a cells and/or cell treatment device according to the present invention. The wavelength for the treatment and/or prophylaxis of dermatitis that is to be emitted by the cells and/or cell treatment device according to the present invention is in the range between 470 and 670 nm. Preferably the wavelength is in the range between 490 and 650 nm, and particularly preferably between 530 and 610 nm. Two particular preferred wavelengths for this purpose are 550 nm and 590 nm.

Atopic eczema of a subject can be treated by a cells and/or cell treatment device according to the present invention. The wavelength for the treatment and/or prophylaxis of atopic eczema that is to be emitted by the cells and/or cell treatment device according to the present invention is in the range between 470 and 670 nm. Preferably the wavelength is in the range between 490 and 650 nm, and particularly preferably between 530 and 610 nm. One particular preferred wavelength for this purpose is 320 nm.

Psoriasis can be treated by a cells and/or cell treatment device according to the present invention. The wavelength for the treatment and/or prophylaxis of psoriasis that is to be emitted by the cells and/or cell treatment device according to the present invention is in the range between 240 and 500 nm. Preferably the wavelength is in the range between 290 and 400 nm, and particularly preferably between 300 and 330 nm. Two particular preferred wavelengths for this purpose are 311 and 320 nm.

Vitiligo can be treated by a cells and/or cell treatment device according to the present invention. The wavelength for the treatment and/or prophylaxis of vitiligo that is to be emitted by cells and/or cell treatment device according to the present invention is in the range between 240 and 500 nm. Preferably the wavelength is in the range between 290 and 400 nm, and particularly preferably between 300 and 330 nm. One particular preferred wavelength for this purpose is 311 nm.

Targeted phototherapy has enabled therapeutic dosing of ultraviolet light to specific dermatoses while minimizing exposure of healthy skin. Specifically, the 308 nm wavelength of light within the ultraviolet B range has been shown as particularly effective for many dermatoses, including vitiligo; psoriasis; and leukoderma such as that associated with scars, striae alba and post-$CO_2$ laser resurfacing.

The cells and/or cell treatment device of the present invention can also be used for the treatment of edema. Edema, formerly known as dropsy or hydropsy, is an abnormal accumulation of fluid beneath the skin or in one or more cavities of the body. Generally, the amount of interstitial fluid is determined by the balance of fluid homeostasis, and increased secretion of fluid into the interstitium or impaired removal of this fluid may cause edema. Five factors can contribute to the formation of edema: (1) It may be facilitated by increased hydrostatic pressure or by reduced oncotic pressure within blood vessels or (2) by increased blood vessel wall permeability as in inflammation or (4) by obstruction of fluid clearance via the lymphatic or (5) by changes in the water retaining properties of the tissues themselves. Raised hydrostatic pressure often reflects retention of water and sodium by the kidney.

The cells and/or cell treatment device according to the present invention used for the treatment of edema preferably emit light in the range between 760 and 940 nm, preferably between 780 and 920 nm, particularly preferably between 800 and 900 nm, and very particularly preferably between 820 and 880 nm. One further particularly preferred emission wavelength for the treatment of edema is 850 nm.

Another subject of the present invention relates to cells and/or cell treatment device according to the present invention for the treatment and/or prophylaxis of infections and inflammatory, neurological, and psychological diseases and/or conditions.

Many inflammatory diseases, disorder, and conditions can be treated with phototherapy. The cells and/or cell treatment device according to the present invention for the treatment and/or prophylaxis of inflammatory disorders is also subject of the present invention. Inflammatory diseases and conditions cover a wide range of indications. Many diseases or conditions which are seemingly unrelated to inflammation have inflammatory components that can be treated with the cells and/or cell treatment device according to the present invention. The skin diseases and conditions mentioned in the present invention all have inflammatory components, such as acne, psoriasis, atopic dermatitis, eczema. A non limiting selection of further inflammatory diseases and conditions that can be treated with cells and/or cell treatment device according to the invention is arthritis, inflammatory bowel disease, gingival inflammation, inflammation of the mucosa, inflammation of the nail bed, arteriosclerosis, and inflammation of the vascular system.

Preferred wavelengths for the treatment and/or prophylaxis of inflammation are in the range between 350 and 900 nm, particularly preferably between 380 and 900 nm, and very particularly preferably between 400 and 860 nm. Further preferred wavelengths for the treatment and/or prophylaxis of inflammation are 405, 420, and 850 nm.

Said cells and/or cell treatment device can be used for the treatment and/or prophylaxis of infections. Infections can be caused by bacteria and viruses. Light has several positive effects on infections. Light has, e.g., anti-inflammatory effects through the stimulation of the tissue as outlined elsewhere within the present invention.

Phototherapy with cells and/or cell treatment device according to the present invention is beneficial for the use to treat wounds. Wound healing is often associated with inflammation. Therefore the same wavelengths and ranges of wavelengths as outlined for the treatment and/or prophylaxis of inflammation can be applied. Treating wounds by phototherapy also prevents the formation of scares. Particularly preferred wavelengths for the treatment and/or prophylaxis of wounds and/or scares are in the range between 600 and 950 nm and very particularly preferably between 650 and 900 nm. Further preferred wavelengths for the treatment and/or prophylaxis of wounds and scares are 660, 720, and 880 nm.

Other infections that can efficiently be treated with cells and/or cell treatment device according to the present invention are caused by bacteria.

Further infections that can efficiently be treated with cells and/or cell treatment device according to the present invention are caused by viruses. A preferred embodiment of this invention is the use of the said cells and/or cell treatment device for the treatment and/or prophylaxis of viral infections particularly caused by cytomegalovirus (CMV), encephalo myocarditis virus (EMCV), poliovirus, influenca virus, parainfluenza respiratory influenza virus, respiratory syncytial virus, Japanese encephalitis virus, Dengue virus, hepatitis A virus (HAV), hepatitis B virus (HBV), hepatitis C virus (HCV), hepatitis D virus (HDV), hepatitis E virus (HEV), hepatitis F virus (HFV), hepatitis G virus (HGV) Epstein Barr Virus (EBV), human immunodeficiency virus type 1 (HIV-I), human immunodeficiency virus type 2 (HIV-2), varicella zoster virus, herpes simplex virus, in particular herpes simplex virus type 1 (HSV-I), herpes simplex virus type 2 (HSV-2), or human herpes virus 1, 2, 3, 4, 7, or 8, Kaposi's sarcoma-associated herpesvirus (KSHV), rotavirus, papilloma virus, and human papilloma virus (HPV), in particular HPV of the types: 1, 2, 3, 4, 5, 8, 9, 11, 12, 13, 14, 15, 16, 17, 18, 19-29, 31, 32, 34, 36-38, 46-50, 56, or 58.

In particular viral skin diseases and/or tumor disorders can be treated with cells and/or cell treatment device according to the present invention such as genital warts, benign tumors of the skin and/or mucosa caused by papilloma viruses, in particular verrucae plantares, verrucae vulgares, verrucae planae juveniles, epidermodysplasia verruciformis, Condylomata acuminate, Condylomata plana, bowenoid papulosis, papilloma on the larynx and oral mucosa, focal epithelial hyperplasia, herpes labialis, varicella and shingles.

In a particularly preferred embodiment of the present invention the cells and/or cell treatment device can be used for the treatment and/or prophylaxis of warts. Pulsed light therapy might be one way to treat warts with devices according to the present invention.

Embodiments of a cells and/or cell treatment device according to the present invention for the treatment and/or prophylaxis of neurological or psychological diseases and/or conditions is also subject of the present invention.

A preferred neurological disease according to the present invention is Morbus Parkinson (MB). When light reaches a certain level of intensity, it inhibits melatonin which in turn limits the production of dopamine. By limiting the melatonin is supposed to lead to a have better production and use of dopamine in the brain. Recent case studies of light therapy on MB patients involving bright light therapy have had positive results with marked improvement in bradykinesia and rigidity in most patients while being exposed for only ninety minutes.

Further preferred neurological and psychological diseases and/or conditions according to the present invention are mood and sleep related. Light is well known to be beneficial on the mood in many circumstances. Phototherapy can also be employed to treat depression, seasonal affective disorder (SAD), non seasonal depression, circadian rhythm sleep disorder (chronic circadian rhythm sleep disorder (CRSD), situational CRSD).

The US National Library of Medicine notes that some people experience a serious mood change when the seasons change. They may sleep too much, have little energy, and crave sweets and starchy foods. They may also feel depressed. Though symptoms can be severe, they usually clear up. The condition in the summer is often referred to as Reverse Seasonal Affective Disorder, and can also include heightened anxiety. It has been estimated that 1.5 to 9% of adults in the US experience SAD.

There are different treatments for classic (winter-based) seasonal affective disorder, including light therapy with bright lights, antidepressant medication, cognitive-behavioral therapy, ionized-air administration, and carefully timed supplementation of the hormone melatonin.

The wavelength for the treatment and/or prophylaxis of these neurological and psychological diseases and/or conditions that is to be emitted by the cells and/or cell treatment device is in the range between 350 and 600 nm. Preferably the wavelength is in the range between 400 and 550 nm, and particularly preferably between 440 and 500 nm. Two particular preferred wavelengths for this purpose are 460 and 480 nm.

The cells and/or cell treatment device according to the present invention may also be used for the treatment and/or prophylaxis of pain. Pain relief by phototherapy is well known. The following conditions produce pain that can be treated successfully with phototherapy: carpal tunnel syndrome, chronic wounds, epicondylitis, headache, migraine, plantar fasciitis, tendonditis and bursitis, neck pain, back pain, muscle pain, trigeminal neuralgia, and Whiplash-associated injuries.

Preferably, muscle pain is treated with cells and/or cell treatment device emitting red or infrared light.

Alopecia greata is a condition affecting humans, in which hair is lost from some or all areas of the body, usually from the scalp. Because it causes bald spots on the scalp, especially in the first stages, it is sometimes called spot baldness. In 1 to 2% of cases, the condition can spread to the entire scalp (alopecia totalis) or to the entire epidermis (alopecia universalis). Conditions resembling alopecia greata, and having a similar cause, occur also in other species.

Alopecia greata (autoimmune hair loss) can be treated by a devices according to the present invention. The wavelength for the treatment and/or prophylaxis of alopecia greata that is to be emitted by the cells and/or cell treatment device according to the present invention is in the range between 240 and 500 nm. Preferably the wavelength is in the range between 290 and 400 nm, and particularly preferably between 300 and 330 nm. One particular preferred wavelength for this purpose is 311 nm.

Embodiments of the cells and/or cell treatment device can also be used for the disinfection and/or sterilization and/or preservation of beverages and nutrition.

The use of light for the purpose of disinfection and/or sterilization and/or preservation is well known. The cells and/or cell treatment device according to the present invention can be used for this purpose. Hereby any kind of disinfection and/or sterilization and/or preservation is meant and includes without limitation the disinfection of wounds, nutrition, and solid and liquids objects, such cosmetic, medical devices, devices used for surgery and beverages.

Preference is given to use of the cells and/or cell treatment device for the disinfection and/or sterilization and/or preservation of beverages, preferably water, and particularly preferably drinking water. Contaminated water causes many infections worldwide and leads often to severe diseases or death of the individuals.

Water filter systems of commercial providers take advantage of ion exchange technology. The filter, however, tend to microbial contamination, which, in turn results in water which is contaminated with microbes. One solution is to add silver salt which may be from a toxicological point of view problematic. The cells and/or cell treatment device of the present invention provide a solution to this problem. They can be used to be incorporated into the water filter system in order to provide a safe, efficient, and low cost way to provide water with a low degree of microbial contamination. The cells and/or cell treatment device can irradiate both the water before or after filtering or the filter cartridge itself. Preferably the cells and/or cell treatment device irradiates both the filter cartridge and the already filtered water.

The procedure of disinfection and/or sterilization and/or preservation of water as outlined above can basically be applied to any other liquid, in particular beverage analogously.

Therefore, cells and/or cell treatment device according to the present invention can be used for the disinfection and/or preservation of beverages and nutrition for humans and animals. Wavelengths for disinfection and/or sterilization and/or preservation according to the present invention are in the range between 200 nm and 600 nm, preferably between 250 nm and 500 nm, and very particularly preferably between 280 nm and 450 nm.

In another embodiment the present invention relates to the said cells and/or cell treatment device for the application in photodynamic therapy (PDT).

Wavelengths required for PDT according to the present invention are in the range between 300 and 700 nm, preferably between 400 and 700 nm, and very particularly preferably between 500 and 700 nm. Four further preferred wavelengths are 595, 600, 630, and 660 nm.

Any therapy known as PDT can be treated with the cells and/or cell treatment device according to the present invention and devices including them. In particularly PDT as outlined within the present invention can be treated with cells and/or cell treatment device according to the present invention. The property of dyes with a polycyclic hydrocarbon type chemical structure to accumulate in greater amounts in tumor tissues than in normal tissues is well known. The dyes include acridines, xanthenes, psoralens, and porphyrins. The latter dyes, in particular, hematoporphyrin (Hp) and some of its chemical derivatives (e.g. Hp D, wherein Hp D is a mixture of Hp derivatives), have superior tumor-localizing properties, which are the basis of photo-therapeutic treatment of tumors with red light irradiation at predetermined times after systemic administration of the drug.

Drug used for PDT are preferably selected from aminolevulinic acid/methyl aminolevulinate, efaproxiral porphyrin derivatives (porfimer sodium, talaporfin, temoporfin, verteporfin).

In a further embodiment the present invention relates to the said cells and/or cell treatment device for the treatment and/or prophylaxis of jaundice and crigler naijar, preferably jaundice.

Jaundice, which is also known as icterus, is a yellowish discoloration of the skin, the conjunctival membranes over the sclerae (whites of the eyes), and other mucous membranes. The discoloration is caused by hyperbilirubinemia (increased levels of bilirubin in the blood). This hyperbilirubinemia subsequently causes increased levels of bilirubin in the extracellular fluids. Jaundice is classified in three groups, pre-hepatic (hemolytic) jaundice, hepatic (hepatocellular) jaundice, and post-hepatic (obstructive) jaundice.

Pre-hepatic jaundice is caused by anything which causes an increased rate of hemolysis, i.e. breakdown of red blood cells. In tropical countries, malaria can cause jaundice in this manner. Certain genetic diseases, such as sickle cell anemia, spherocytosis and glucose 6-phosphate dehydro-genase deficiency can lead to increased red cell lysis and therefore hemolytic jaundice. Commonly, diseases of the kidney, such as hemolytic uremic syndrome, can also lead to coloration. Defects in bilirubin metabolism also present as jaundice. Jaundice usually comes with high fevers. Rat fever (leptospirosis) can also cause jaundice.

Hepatic jaundice causes include acute hepatitis, hepatotoxicity and alcoholic liver disease, whereby cell necrosis reduces the liver's ability to metabolise and excrete bilirubin leading to a buildup in the blood. Less common causes include primary biliary cirrhosis, Gilbert's syndrome (a genetic disorder of bilirubin metabolism which can result in mild jaundice, which is found in about 5% of the population), Crigler-Najjar syndrome, metastatic carcinoma and Niemann-Pick disease, type C. Jaundice seen in the newborn, known as neonatal jaundice, is common, occurring in almost every newborn as hepatic machinery for the conjugation and excretion of bilirubin does not fully mature until approximately two weeks of age.

Post-hepatic jaundice, also called obstructive jaundice, is caused by an interruption to the drainage of bile in the biliary system. The most common causes are gallstones in the common bile duct, and pancreatic cancer in the head of the pancreas. Also, a group of parasites known as "liver flukes" can live in the common bile duct, causing obstructive jaundice. Other causes include strictures of the common bile duct, biliary atresia, ductal carcinoma, pancreatitis and pancreatic pseudocysts. A rare cause of obstructive jaundice is Mirizzi's syndrome.

Jaundice, in particular neonatal jaundice, can lead to severe medical consequences if not or not appropriately treated. Increased concentrations of bilirubin can result in a brain-damaging condition known as kernicterus, leading to significant lifelong disability; there are concerns that this condition has been rising in recent years due to inadequate detection and treatment of neonatal hyperbilirubinemia. Early treatment often consists of exposing the infant to intensive phototherapy in an more or less isolated incubator. The therapy often represents an emotionally or psychologically difficult situation for both the infant and the parents. The devices of the present invention can be employed in order to provide flexible and ambulatory devices such as blankets. Thus, the infant can be treated while laying in its parents' arms. Traditional therapies also easily lead to overheating of the infant, which can also be significantly reduced with the cells and/or cell treatment device of the present invention and devices including them.

Preferably the present invention relates to use of the cells and/or cell treatment device for the treatment of neonatal jaundice.

Jaundice of a subject can be treated by cells and/or cell treatment device according to the present invention. The wavelength for the treatment and/or prophylaxis of jaundice that is to be emitted by the cells and/or cell treatment device according to the present invention is in the range between 300 and 700 nm. Preferably the wavelength is in the range between 350 and 600 nm, and particularly preferably between 370 and 580 nm. Further preferred wavelengths are in the range between 400 and 550 nm. Particularly preferred wavelengths are in the range between 410 and 470 nm. Two particular preferred wavelengths for this purpose are 450 and 466 nm.

In another embodiment the present invention relates to the use of the cells and/or cell treatment device for the preparation of a device for the treatment and or/prophylaxis of therapeutic diseases and/or cosmetic conditions. The therapeutic diseases and conditions are the same as the ones described elsewhere in the present invention.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention.

Independent protection may be sought for these features in addition to or alternative to any invention presently claimed.

The teaching as disclosed here can be abstracted and combined with other examples disclosed.

Other features of the invention will become apparent in the course of the following description of exemplary embodiments and drawings, which are given for illustration of the invention and are not intended to be limiting thereof.

WORKING EXAMPLES

Example 1

Materials

PDY-132, a yellow emissive polymer available from Merck KGaA, Germany, is a PPV (poly(para-phenylene vinylene)) polymer emitting yellow light with a broad emission between 500 to 700 nm. PDY-132 is synthesized by Gilch polymerization.

Quantum dot (QD1), PL-QD-O-590 available from Plasmachem GmbH, Berlin, Germany, has an emission peak around 590 nm and a CdSe spheric core capped with epitaxial ZnS shell. QD1 have a surface hydrophobic layer comprising mostly trioctylphosphine oxide.

Quantum dot (QD2), having peak emission at 850 nm, also available from Plasmachem GmbH. QD2 have a surface hydrophobic layer comprising mostly trioctylphosphine oxide.

Triplet green emitter TEG1 is synthesized according to WO 2004/026886:

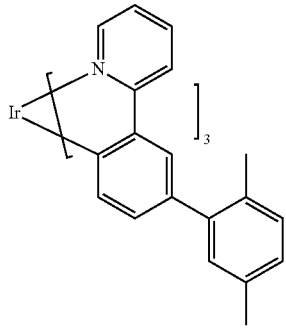

TMM1 is a triplet matrix material, and synthesized according to WO 2005/053055:

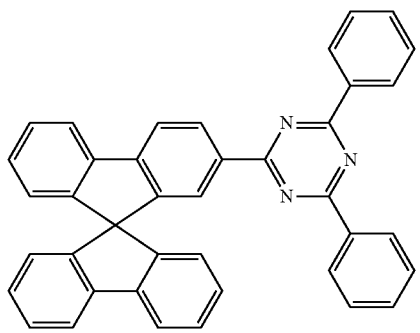 [SMILES: c1ccc(-c2nc(-c3ccccc3)nc(-c3ccc4c(c3)C3(c5ccccc5-c5ccccc53)c3ccccc3-4)n2)cc1]

TMM2 is wide-gap materials, used as triplet co-matrix material, and is synthesized according to WO 2009/124627:

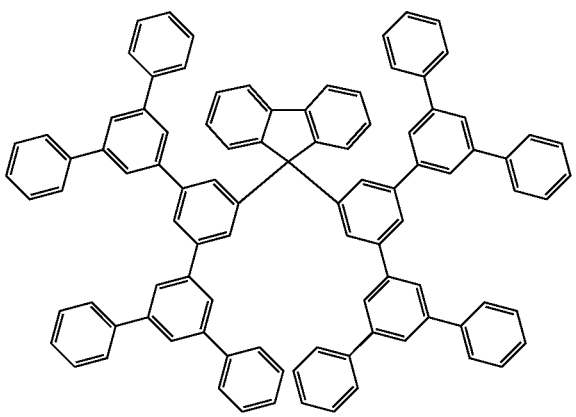 [SMILES: c1ccc(-c2cc(-c3ccccc3)cc(-c3cc(-c4cc(-c5ccccc5)cc(-c5ccccc5)c4)cc(C4(c5cc(-c6cc(-c7ccccc7)cc(-c7ccccc7)c6)cc(-c6cc(-c7ccccc7)cc(-c7ccccc7)c6)c5)c5ccccc5-c5ccccc54)c3)c2)cc1]

Poly(ethylene oxide) (PEO, $M_w$=5×10$^6$, Aldrich) is used as ion conductor; and Lithium trifluoromethane sulfonate (LiTrf, 99.995% metal basis; Aldrich) as ion source.

HIL-012, available from Merck KGaA, is a hole transport and electron blocking material, and will be used as interlayer (IL).

Figure 1A:
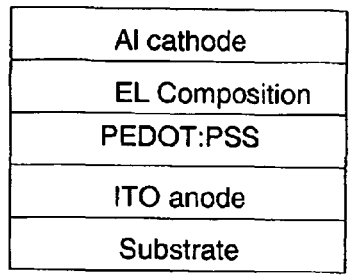
FIG. 1a: Device structure for an OLEC1
Figure 1B:
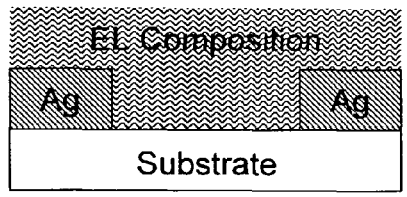
FIG. 1b: Device structure for an OLEC2

The flexible poly(ethylene naphthalate) (PEN) is used as substrate for OLEC and QD-OLECs. For OLECs with the sandwiched structure, as depicted in FIG. 1a and FIG. 1b, 150 nm ITO is sputtered on PEN using a mask. It will be referred hereafter to as Sub1. Sub1 has a dimension of 3×3 cm$^2$, and an OLEC pixel of 2×2 cm$^2$.

Example 2

Yellow OLEC1 using PDY-132

OLEC1 using PDY-132 in the emissive layer, in a sandwiched structure of ITO/PEDOT/Interlayer/EMLCathode is prepared as follows:
1. PDEOT (Baytron P A14083) is deposited with a thickness of 80 nm onto Sub1 by spin coating and then heated for 10 min. at 120° C.;
2. Deposition of 20 nm interlayer by spin coating from toluene solution of HIL-012 having a concentration of 0.5% wt/l in glovebox.
3. The emissive layer is deposited by spin-coating a solution in Cyclohexanone including PDY-132 yielding a layer with a thickness of 300 nm in the glove-box; the composition of EML is listed in table 1;
4. The device is heated at 120° C. for 30 min. to remove residual solvent;
5. An Al (150 nm) cathode is deposited by evaporation onto the emissive layer.

Figure 1C:
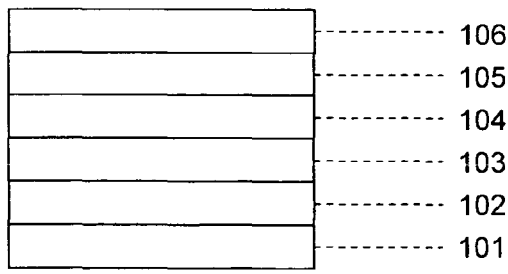
FIG. 1c: Device structure for a QD-LEC, with substrate (101), anode (102), buffer layer or HIL (103), interlayer (104), EML (105) and cathode (106).
Figure 2:
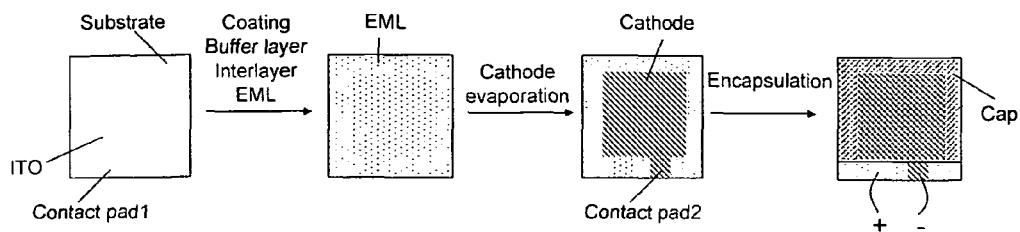
FIG. 2: Schema for the preparation of the QD-LEC on flexible substrate.
Figure 3:
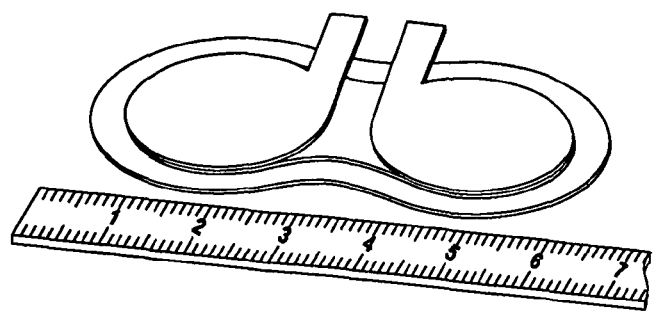
FIG. 3: Attachment of printed battery to plaster including a cell and/or cell treatment device including a QD-LEC.
Figure 4:
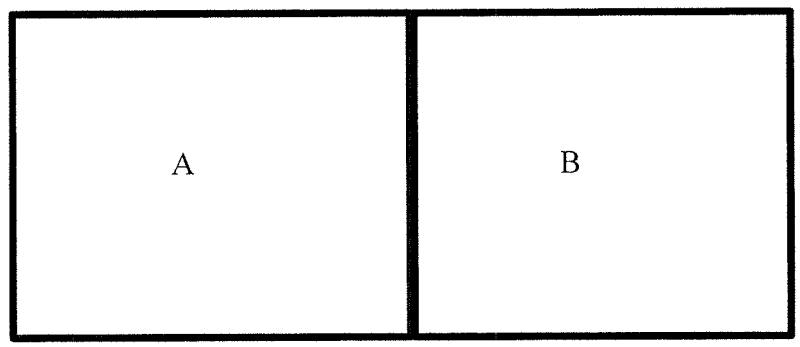
FIG. 4: Device including both at least one light source (A) and at least one further light source (B).
Figure 5:
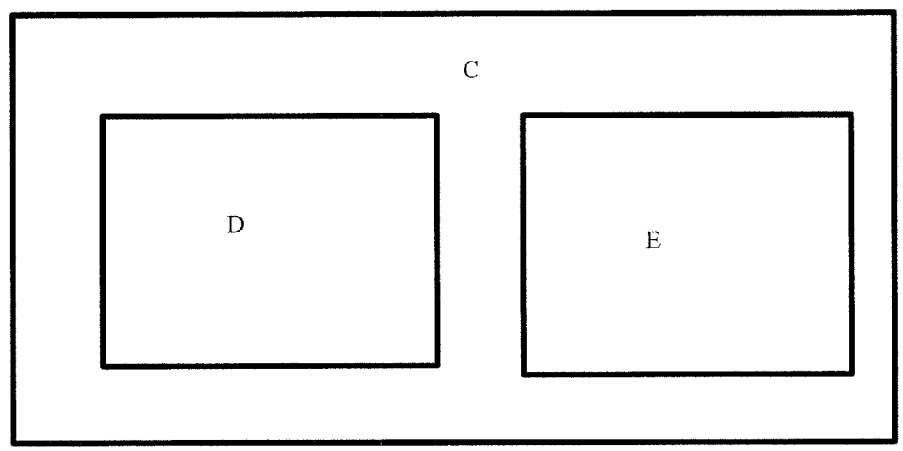
FIG. 5: Kit (C) including the device (D) and a topical composition (E).
Figure 6:
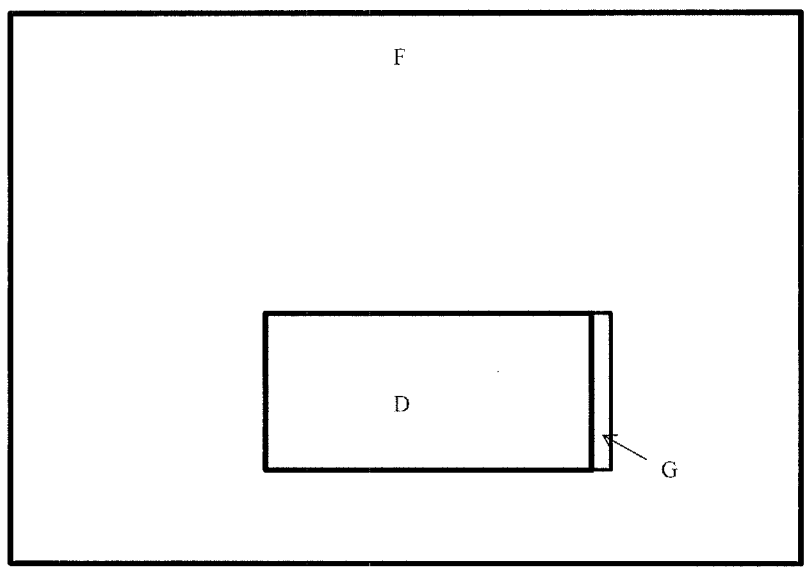
FIG. 6: Ambulatory device (F), for example a blanket, including the device (D) attached by way of attachment means (G), for example an adhesive surface.

The device is encapsulated using a UV-cured resin, UV Resin T-470/UR7114 (Nagase Chemtex Corporation), and a PEN cap, which is smaller than the substrate to leave the contact pads free, as schematically shown in FIG. 1. The UV-resin is applied at first on the edge of the pixel, and the cap is then located on top of them. Then the device is exposed to UV light for 30 seconds. All theses are done in glove-box.

Example 3

Yellow QD-OLEC1 using QD1

QD-OLEC1 including QD1 in the emissive layer, in a sandwiched structure of ITO/PEDOT/Interlayer/EML/Cathode is prepared using the same steps as OLEC1 except step 3, which is for QD-OLEC1:
3. The emissive layer is deposited by dip-coating a solution in Cyclohexanone including QD1 yielding a layer with a thickness of 300 nm in the glove-box; the composition of EML is listed in table 1;

The QD-OLEC1 is then encapsulated as OLEC1.

TABLE 1

EML compositon of OLEC1 and QD-OLEC1

| | Composition for EML [wt %] | Concentration [mg/ml] | EML thickness [nm] |
|---|---|---|---|
| OLEC1 | 45% PDY-132:45% PEO:10% LiTrf | 12 | 300 |
| QD-OLEC1 | 13.5% TMM1:13.5% TMM2:9% TEG1:36% PEO:8% LiTrf:20% QD1 | 24 | 300 |

Example 4

Combi Light Sources with Phosphor1

The Combi Light Sources, comprising yellow centered at 590 nm and IR centered at 850 nm IR devices are prepared by using OLEC1 and QD-OLEC1 and the down-conversion quantum dot QD2.

QD2 is dispersed in a silicone binder. And the Combi light sources are prepared by dip coating of QD2 dispersion onto the emitting surface of the devices OLEC1 and QD-OLEC1 of Example 2 & 3. The emission spectrum of Combi-Light Source (Source1 for OLEC1, and Source2 for QD-OLEC1) are recorded by spectrometer USB2000 (Ocean Optics). The thicknesses of the Phosphor1 are adjusted until the power ratio of yellow and IR is 4:1.

Example 5

Device for Therapeutic and/or Cosmetic Applications

The final devices for using in therapeutic and cosmetic applications can be realized, e.g., by attaching the Combi light sources to plasters. The external power source can be applied through the contact pads.

A battery is a preferred power source for the devices, particularly preferred is the printed thin film battery for light weight. The printed thin film battery can be acquired, e.g., from Enfucell Oy Ltd, Petikontie 16-18, 01720 Vantaa, Finland.

In some treatments, the device should be driven in pulse mode. Therefore a controller, particularly a pocket portable one, for pulse driving, can be used. This can be realised by using a commercially available flasher unit or blinker unit. Further such flasher unit can be integrated in the power unit, according to the principle of general trigger circuit, as for example shown in Fachkunde Elektrotechnik, Verlag Europa-Lehrmittel, Nourney, Vollmer GmbH & Co., 5657 Haan-Gruiten, 227.

Example 6

Wrinkle Reduction with Pulsed Treatment

As disclosed in Example 1 in WO 2003/086215 females are treated with a light source according to the present invention. However, instead of a LED light source having a dominant emission wavelength at 574 nm, QD-OLEC1 having a dominant emission wavelength at 590 nm is used. Furthermore, 10 females are treated, rather than 6. The average value of wrinkle reduction after 12 weeks is 72%.

Example 7

Acne Reduction with Multiple, Simultaneous Light Sources

As disclosed in Example 7 in WO 2003/086215 patients exhibiting acne and acne scarring are treated. The light source used here is the Combi Light Source of Example 4 according to the present invention. Each of the 6 patients exhibits a substantial decrease in visible acne and acne scarring as well as a reduction in the presence of acne bacteria.

The invention claimed is:

1. A cell and/or cell tissue treatment device, comprising at least one light source selected from the group consisting of an organic light emitting electrochemical cell (OLEC) and a light emitting electrochemical cell including at least one quantum dot (QD-LEC).

2. The device according to claim 1, characterized in that the at least one element chosen from OLEC, QD-LEC is adapted for activation, stimulation, deactivation, disinfection, depilation, phototherapy, extracorporeal treatment, and/or intracorporeal treatment of cells and/or cell tissue, and/or lifting of cell tissue.

3. The device according to claim 1, characterized in that the at least one element chosen from OLEC, QD-LEC is adapted to emit multichromatic and/or narrowband light and/or light in the yellow wavelength range and/or light in the infrared wavelength range; and/or wherein the cells and/or cell tissue treatment device is a continuous wave and/or pulsed device.

4. The device according to claim 3, characterized in that the at least one element chosen from OLEC, QD-LEC is adapted to emit a multichromatic light having an effective radiated power ratio of about 4:1 of yellow light to infrared light; and/or to emit a multichromatic light including yellow light of about 590 nm at an effective radiated power of about 4 mW/cm$^2$ and infrared light of about 850 nm at an effective radiated power of about 1 mW/cm$^2$.

5. The device according to claim 1, characterized in that the at least one element chosen from OLEC, QD-LEC is adapted to emit light at a wavelength from about 300 nm to about 1300 nm, and/or at a total energy fluence of less than 10 J/cm2, and/or at pulses having a duration of from about 0.1 femtoseconds to about 100 seconds, and/or the interpulse delay being between said pulses being from about 0.1 to about 1000 milliseconds.

6. The device according to claim 1 comprising at least one element chosen from an ultrasound source, filter means adapted for reducing the intensity of infrared radiation received by the cells and/or cell tissue, filter means for selecting a wavelength or a wavelength band, and cooling means.

7. The device according to claim 1, characterized in that the cells or cells of the cell tissue are at least one element chosen from plant cells, animal cells, human cells, mammalian cells, eucaryotic cells, procaryotic cells, hair cells, hair root cells, skin cells, mucosal cells, and stem cells.

8. A method of cosmetic treatment; prophylactic treatment;
therapeutic treatment; non-invasive treatment; activation, stimulation, deactivation, disinfection, depilation, phototherapy, photodynamic therapy, extracorporeal treatment, intracorporeal treatment of cells and/or cell tissue; peeling and/or lifting of cell tissue; and/or activation or inhibition of the differentiation of stem cells comprising utilizing the device according to claim 1.

9. The method according to claim 8, characterized in that the cells or cells of the cell tissue are at least one element chosen from plant cells, animal cells, human cells, mammalian cells, eucaryotic cells, procaryotic cells, hair cells, hair root cells, skin cells, mucosal cells, and stem cells.

10. The method according to claim 8, characterized in that the cosmetic treatment is directed to the treatment and/or prophylaxis of acne and wrinkles of the skin.

11. A method for treatment of cells and/or cell tissue, comprising exposing cells or cell tissue to light emitted from a device according to claim 1.

12. The method according to claim 11, characterized in that the step of exposing cells or cell tissue to light includes emitting multichromatic and/or narrowband light and/or light in the yellow wavelength range and/or light in the infrared wavelength range.

13. The method according to claim 11, characterized in that the step of exposing cells or cell tissue to light includes emitting multichromatic light having a effective radiated power ratio of about 4:1 of yellow light to infrared light; and/or wherein the step of exposing cells or cell tissue to light includes emitting multichromatic light including yellow light of about 590 nm at an effective radiated power of about 4 mW/cm$^2$ and infrared light of about 850 nm at an effective radiated power of about 1 mW/cm2.

14. The method according to claim 11, comprising applying a topical composition or a topical chromophore composition to the cells or cell tissue before, during or after exposing the cells or the cell tissue to the light.

15. The method according to claim 14, characterized in that the topical composition or the topical chromophore composition is encapsulated or microencapsulated in a vehicle; and/or
wherein the topical composition includes at least one element chosen from naturally occurring chlorophyll-containing compounds, carotenoid-containing compounds, phyocobilin compounds, indocyanine green, methylene blue, rose Bengal, Vitamin C, Vitamin E, Vitamin D, Vitamin A, Vitamin K, Vitamin F, Retin A (Tretinoin), Adapalene, Retinol, Hydroquinone, Kojic acid, a growth factor, echinacea, an antibiotic, an antifungal, an antiviral, a bleaching agent, an alpha hydroxy acid, a beta hydroxy acid, salicylic acid, antioxidant triad compound, a seaweed derivative, a salt water derivative, algae, an antioxidant, a phytoanthocyanin, a phytonutrient, plankton, a botanical product, a herbaceous product, a hormone, an enzyme, a mineral, a cofactor, an antiaging substance, insulin, minoxidil, lycopene, a natural or synthetic melanin, a metalloproteinase inhibitor, proline, hydroxyproline, an anesthetic, chlorophyll, bacteriochlorophyll, copper chlorophyllin, chloroplasts, carotenoids, phycobilin, rhodopsin, anthocyanin, inhibitors of omithine decarboxylase, inhibitors of vascular endothelial growth factor (VEGF), inhibitors of phospholipase A2, inhibitors of S-adenosylmethionine, licorice, licochalone A, genestein, soy isoflavones, phtyoestrogens, derivative, analogs, homologs, and subcomponents thereof, and derivatives, subcomponents, immunological complexes and antibodies of said cells or cell tissue, and synthetic and natural analogs thereof, combinations thereof; and/or
wherein the topical chromophore composition has at least one absorption maximum between 300 nm and 1300 nm and includes an active ingredient selected from the group consisting of chlorophyll, porphyrin, and combinations thereof, wherein the active ingredient has at least one metal-ligand bond, wherein the metal in the metal-ligand bond is selected from the group consisting of Fe, Mg, Cu, Al, reactive transition metals, metal chelates, and antibody complexes.

16. The method according to claim 11, characterized in that by exposing the cells or the cell tissue to the light at least one element chosen from cosmetic treatment; prophylactic treatment; therapeutic treatment; non-invasive treatment; activation, stimulation, deactivation, disinfection, depilation, phototherapy, photodynamic therapy, extracorporeal treatment, intracorporeal treatment of cells and/or cell tissue; peeling or lifting of cell tissue; and/or activation or inhibition of the differentiation of stem cells is performed.

17. The method according to claim 11, characterized in that the cells or the cells of the cell tissue are at least one element chosen from plant cells, animal cells, human cells, mammalian cells, eucaryotic cells, procaryotic cells, hair cells, hair root cells, skin cells, mucosal cells, and stem cells.

18. The method according to claim 11, characterized in that the treatment is no treatment of the human or animal body by surgery or therapy and/or is not practised on the human or animal body.

* * * * *